United States Patent
Daniel et al.

(10) Patent No.: US 11,142,614 B2
(45) Date of Patent: Oct. 12, 2021

(54) PROCESS FOR PRODUCING SURFACE-POSTCROSSLINKED WATER-ABSORBENT POLYMER PARTICLES

(71) Applicant: BASF SE, Ludwigshafen (DE)

(72) Inventors: Thomas Daniel, Waldsee (DE);
Norbert Herfert, Shanghai (CN);
Stephan Bauer, Hochheim (DE);
Katrin Baumann, Mannheim (DE);
Birgit Reinhard, Limburgerhof (DE);
Jürgen Freiberg, Lampertheim (DE);
Christophe Bauduin, Plankstadt (DE);
Katarzyna Dobrosielska-Oura, Ludwigshafen (DE); Michael A. Mitchell, Waxhaw, NC (US)

(73) Assignee: BASF SE, Ludwigshafen (DE)

( * ) Notice: Subject to any disclaimer, the term of this patent is extended or adjusted under 35 U.S.C. 154(b) by 250 days.

(21) Appl. No.: 16/217,740

(22) Filed: Dec. 12, 2018

(65) Prior Publication Data
US 2019/0135993 A1    May 9, 2019

Related U.S. Application Data

(63) Continuation of application No. 14/443,082, filed as application No. PCT/EP2013/073236 on Nov. 7, 2013, now Pat. No. 10,208,170.
(Continued)

(30) Foreign Application Priority Data

Aug. 26, 2013   (EP) .................................... 13181703

(51) Int. Cl.
*C08J 3/24* (2006.01)
*C08J 9/00* (2006.01)
(Continued)

(52) U.S. Cl.
CPC ............. *C08J 3/245* (2013.01); *A61L 15/225* (2013.01); *A61L 15/425* (2013.01); *A61L 15/60* (2013.01);
(Continued)

(58) Field of Classification Search
CPC ..... C08J 3/245; C08J 3/247; C08J 9/00; C08J 2207/12; C08J 2333/02; A61L 15/225;
(Continued)

(56) References Cited

U.S. PATENT DOCUMENTS 5,229,488 A    7/1993 Nagasuna et al.
5,269,980 A    12/1993 Levendis et al.
(Continued)

FOREIGN PATENT DOCUMENTS

DE    10107709 A1    8/2002
DE    102005062929 A1    7/2007
(Continued)

OTHER PUBLICATIONS

Buchholz, Fredric L., et al., *Modern Superabsorbent Polymer Technology*, "Commercial Processes for the Manufacture of Superabsorbent Polymers." New York: John Wiley & Sons, Inc., 1998, pp. 87-103.
(Continued)

*Primary Examiner* — Ling Siu Choi
*Assistant Examiner* — Ronald Grinsted
(74) *Attorney, Agent, or Firm* — Marshall, Gerstein & Borun LLP

(57) ABSTRACT

The present invention relates to a process for producing surface-postcrosslinked water-absorbent polymer particles by coating of water-absorbent polymer particles having a content of residual monomers in the range from 0.03 to 15%
(Continued)

by weight with at least one surface-postcrosslinker and thermal surface-postcrosslinking at temperatures in the range from 100 to 180° C.

12 Claims, 12 Drawing Sheets

Related U.S. Application Data

(60) Provisional application No. 61/728,839, filed on Nov. 21, 2012.

(51) Int. Cl.
| | |
|---|---|
| *A61L 15/22* | (2006.01) |
| *A61L 15/42* | (2006.01) |
| *A61L 15/60* | (2006.01) |
| *B01J 20/26* | (2006.01) |
| *B01J 20/28* | (2006.01) |
| *C08F 6/00* | (2006.01) |
| *C08F 220/06* | (2006.01) |
| *C08F 222/10* | (2006.01) |

(52) U.S. Cl.
CPC ....... *B01J 20/267* (2013.01); *B01J 20/28004* (2013.01); *B01J 20/28011* (2013.01); *B01J 20/28019* (2013.01); *C08F 6/008* (2013.01); *C08F 220/06* (2013.01); *C08J 3/247* (2013.01); *C08J 9/00* (2013.01); *C08F 222/1006* (2013.01); *C08J 2207/12* (2013.01); *C08J 2333/02* (2013.01)

(58) Field of Classification Search
CPC ...... A61L 15/425; A61L 15/60; B01J 20/267; B01J 20/28004; B01J 20/28011; B01J 20/28019; C08F 6/008; C08F 220/06; C08F 222/1006
USPC .......................................................... 524/53
See application file for complete search history.

(56) References Cited

U.S. PATENT DOCUMENTS

| | | | |
|---|---|---|---|
| 6,060,557 A | 5/2000 | Dahmen et al. | |
| 6,187,872 B1 | 2/2001 | Yanase et al. | |
| 6,562,879 B1 | 5/2003 | Hatsuda et al. | |
| 7,176,149 B2 | 2/2007 | Dutkiewicz et al. | |
| 2002/0120085 A1 | 8/2002 | Matsumoto et al. | |
| 2002/0161132 A1 | 10/2002 | Irie et al. | |
| 2007/0066167 A1* | 3/2007 | Wada | C08J 3/12 442/101 |
| 2008/0306209 A1 | 12/2008 | Stueven et al. | |
| 2009/0258994 A1 | 10/2009 | Stueven et al. | |
| 2010/0029866 A1 | 2/2010 | Losch et al. | |
| 2011/0125119 A1 | 5/2011 | Weismantel et al. | |
| 2011/0130275 A1 | 6/2011 | Weismantel et al. | |
| 2011/0130735 A1 | 6/2011 | Weismantel et al. | |
| 2011/0238026 A1 | 9/2011 | Zhang et al. | |
| 2012/0328861 A1 | 12/2012 | Hinayama et al. | |

FOREIGN PATENT DOCUMENTS

| | | |
|---|---|---|
| EP | 0 348 180 A2 | 12/1989 |
| EP | 1562747 A1 | 8/2005 |
| EP | 2524679 A1 | 11/2012 |
| EP | 3165564 A1 | 5/2017 |
| JP | 2009543915 A | 12/2009 |
| JP | 2011529753 A | 12/2011 |
| JP | 2011529754 A | 12/2011 |
| JP | 2011529755 A | 12/2011 |
| JP | 2013503927 A | 2/2013 |
| JP | 2013521962 A | 6/2013 |
| JP | 2013522403 A | 6/2013 |
| WO | WO-96/40427 A1 | 12/1996 |
| WO | WO-2006/094907 A1 | 9/2006 |
| WO | WO-2008/009580 A1 | 1/2008 |
| WO | WO-2008/052971 A1 | 5/2008 |
| WO | WO-2009/094506 A1 | 7/2009 |
| WO | WO-2010/015591 A1 | 2/2010 |
| WO | WO-2011/026876 A1 | 3/2011 |
| WO | WO-2011/086843 A1 | 7/2011 |
| WO | WO-2011/113728 A1 | 9/2011 |
| WO | WO-2011/117263 A1 | 9/2011 |
| WO | WO-2013/143943 A1 | 10/2013 |

OTHER PUBLICATIONS

International Search Report for International Application No. PCT/EP2013/073236, dated Jan. 28, 2014.

Buchholz, et al., Modern Superabsorbent Polymer Technology, Wiley-VCH, Inc., Dec. 31, 1998, pp. 71-103.

Frank, "Superabsorbents", Ullmann's Encyclopedia of Industrial Chemistry, 6th Edition, 2003, pp. 73-93.

European Search Report for EP Patent Application No. 18155569.9, dated Jul. 13, 2018.

"Harmonized Test Method Nonwovens and Related Industries," INDA and EDANA, 2012 Edition.

* cited by examiner

PROCESS FOR PRODUCING SURFACE-POSTCROSSLINKED WATER-ABSORBENT POLYMER PARTICLES

CROSS-REFERENCE TO RELATED APPLICATIONS

This is a divisional of U.S. application Ser. No. 14/443,082, filed May 15, 2015, which is the is the U.S. National Stage of PCT/EP2013/073236, filed Nov. 7, 2013, which claims the benefit of EP Patent Application No. 13181703.3, filed Aug. 26, 2013, and U.S. Provisional Patent Application No. 61/728,839, filed Nov. 21, 2012, incorporated herein by reference in its entirety.

DESCRIPTION

The present invention relates to a process for producing surface-postcrosslinked water-absorbent polymer particles by coating of water-absorbent polymer particles having a content of residual monomers in the range from 0.03 to 15% by weight with at least one surface-postcrosslinker and thermal surface-postcrosslinking at temperatures in the range from 100 to 180° C.

The preparation of water-absorbent polymer particles is described in the monograph "Modern Superabsorbent Polymer Technology", F. L. Buchholz and A. T. Graham, Wiley-VCH, 1998, on pages 71 to 103.

Being products which absorb aqueous solutions, water-absorbent polymer particles are used to produce diapers, tampons, sanitary napkins and other hygiene articles, but also as water-retaining agents in market gardening. Water-absorbent polymer particles are also referred to as "super-absorbent polymers" or "superabsorbents".

The preparation of water-absorbent polymer particles by polymerizing droplets of a monomer solution is described, for example, in EP 0 348 180 A1, WO 96/40427 A1, U.S. Pat. No. 5,269,980, WO 2008/009580 A1, WO 2008/052971 A1, WO2011/026876 A1, and WO 2011/117263 A1.

Polymerization of monomer solution droplets in a gas phase surrounding the droplets ("dropletization polymerization") affords round water-absorbent polymer particles of high mean sphericity (mSPHT). The mean sphericity is a measure of the roundness of the polymer particles and can be determined, for example, with the Camsizer® image analysis system (Retsch Technology GmbH; Haan; Germany).

It was an object of the present invention to provide water-absorbent polymer particles having improved properties, i.e. water-absorbent polymer particles having a high centrifuge retention capacity (CRC) and a high absorption under a load of 49.2 g/cm² (AUHL).

It was another object of the present invention to provide water-absorbent polymer particles that possess a high centrifuge retention capacity and which impart good liquid distribution when used in hygiene articles.

Yet another object of the present invention is to provide water-absorbent polymer particles that allow usage reduction in hygiene articles while maintaining excellent dryness.

The object is achieved by a process for producing water-absorbent polymer, comprising the steps forming water-absorbent polymer particles by polymerizing a monomer solution, coating of water-absorbent polymer particles with at least one surface-postcrosslinker and thermal surface-postcrosslinking of the coated water-absorbent polymer particles, wherein the content of residual monomers in the water-absorbent polymer particles prior to the coating with the sur-face-postcrosslinker is in the range from 0.03 to 15% by weight, and the temperature during the thermal surface-postcrosslinking is in the range from 100 to 180° C.

The present invention further provides a process for producing water-absorbent polymer, comprising the steps forming water-absorbent polymer particles by polymerizing a monomer solution, coating of water-absorbent polymer particles with at least one surface-postcrosslinker and thermal surface-postcrosslinking of the coated water-absorbent polymer particles, wherein the content of residual monomers in the water-absorbent polymer particles prior to the coating with the surface-postcrosslinker is in the range from 0.1 to 10% by weight, the surface-postcrosslinker is an alkylene carbonate, and the temperature during the thermal surface-postcrosslinking is in the range from 100 to 180° C.

The present invention is based on the finding that the level of residual monomers in the water-absorbent polymer particles prior to the thermal surface-postcrosslinking, the temperature of the thermal surface-postcrosslinking, and the surface-postcrosslinker itself have an important impact on the properties of the formed surface-postcrosslinked water-absorbent polymer particles.

The result of the specific conditions according to the process of the present invention are water-absorbent polymer particles having a high centrifuge retention capacity (CRC) and a high absorption under a load of 49.2 g/cm² (AUHL). That is a surprising result. It is known that the centrifuge retention capacity (CRC) significantly decreases during thermal surface-postcrosslinking as proven by Ullmann's Encyclopedia of Industrial Chemistry, 6$^{th}$ Ed., Vol. 35, page 84, FIG. 7. Further surprising is that the less reactive alkylene carbonate reacts under the inventive conditions at unusual low temperatures. Other cyclic surface-postcrosslinkers, for example 2-oxazolidinone, show a very similar behaviour. According to the monograph "Modern Superabsorbent Polymer Technology", F. L. Buchholz and A. T. Graham, Wiley-VCH, 1998, page 98, the recommended reaction temperatures for alkylene carbonates are in the range from 180 to 215° C.

The combination of having a high centrifuge retention capacity (CRC) and a high absorption under a load of 49.2 g/cm² (AUHL) results in water-absorbent polymer particles having a high total liquid uptake in the wicking absorption test.

The specific conditions result further in water-absorbent polymer particles having a reduced pressure dependency of the characteristic swelling time in the VAUL test at high centrifuge retention capacities (CRC).

The present invention further provides surface-postcrosslinked water-absorbent polymer particles having a centrifuge retention capacity (CRC) from 35 to 75 g/g, an absorption under high load (AUHL) from 20 to 50 g/g, a level of extractable constituents of less than 10% by weight, and a porosity from 20 to 40%.

The present invention further provides surface-postcrosslinked water-absorbent polymer particles having a total liquid uptake of $$Y > -500 \times \ln(X) + 1880$$

wherein Y [g] is the total liquid uptake and X [g/g] is the centrifuge retention capacity, wherein the centrifuge retention capacity is at least 25 g/g and the liquid uptake is at least 30 g.

The present invention further provides surface-postcrosslinked water-absorbent polymer particles having a change of characteristic swelling time of less than 0.6 and a centrifuge retention capacity of at least 35 g/g, wherein the change of characteristic swelling time is $$Z<(\tau_{0.5}-\tau_{0.1})/\tau_{0.5}$$

wherein Z is the change of characteristic swelling time, $\tau_{0.1}$ is the characteristic swelling time under a pressure of 0.1 psi (6.9 g/cm$^2$) and $\tau_{0.5}$ is the characteristic swelling time under a pressure of 0.5 psi (35.0 g/cm$^2$).

The present invention further provides fluid-absorbent articles which comprise the inventive water-absorbent polymer particles.

DETAILED DESCRIPTION OF THE INVENTION

Figure 1:
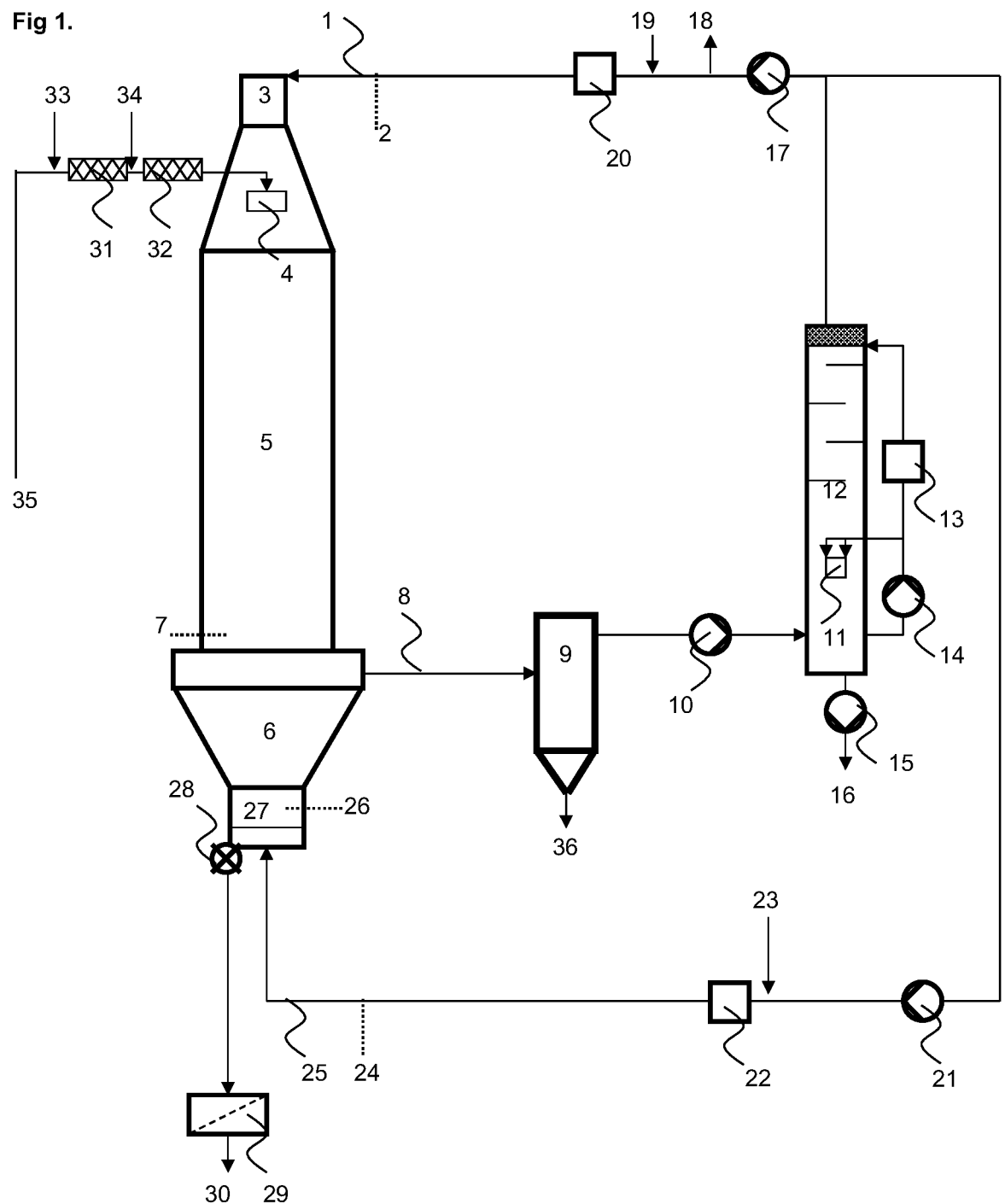
FIG. 1 illustrates a process scheme without an external fluidized bed.
Figure 2:
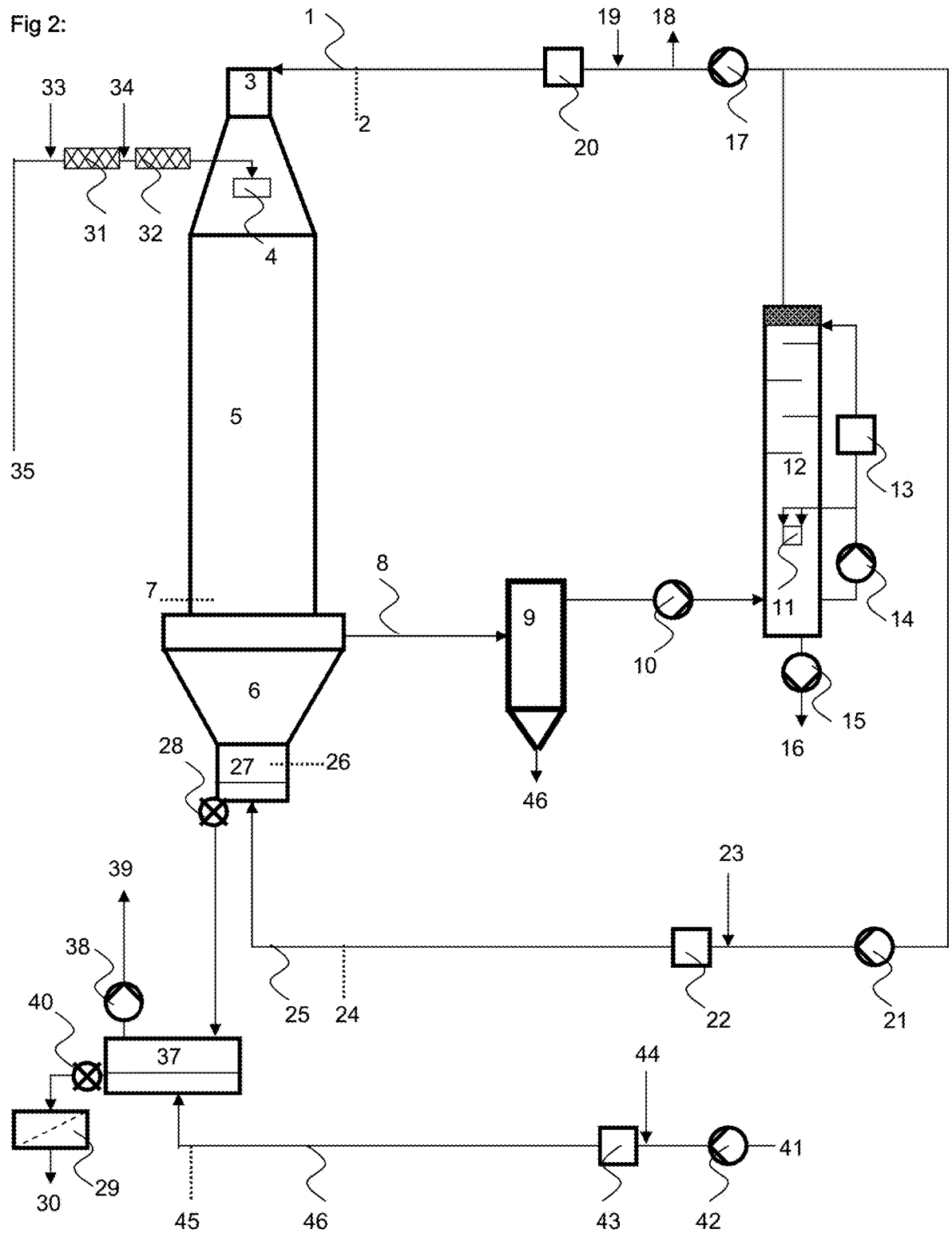
FIG. 2 illustrates a process scheme with an external fluidized bed.

The water-absorbent polymer particles are prepared by a process, comprising the steps forming water-absorbent polymer particles by polymerizing a monomer solution, comprising
a) at least one ethylenically unsaturated monomer which bears acid groups and may be at least partly neutralized,
b) optionally one or more crosslinker,
c) at least one initiator,
d) optionally one or more ethylenically unsaturated monomers copolymerizable with the monomers mentioned under a),
e) optionally one or more water-soluble polymers, and
f) water,
coating of water-absorbent polymer particles with at least one surface-postcrosslinker and thermal surface-postcrosslinking of the coated water-absorbent polymer particles, wherein the content of residual monomers in the water-absorbent polymer particles prior to the coating with the surface-postcrosslinker is in the range from 0.03 to 15% by weight, the surface-postcrosslinker is an alkylene carbonate, and the temperature during the thermal surface-postcrosslinking is in the range from 100 to 180° C.

The water-absorbent polymer particles are typically insoluble but swellable in water.

The monomers a) are preferably water-soluble, i.e. the solubility in water at 23° C. is typically at least 1 g/100 g of water, preferably at least 5 g/100 g of water, more preferably at least 25 g/100 g of water, most preferably at least 35 g/100 g of water.

Suitable monomers a) are, for example, ethylenically unsaturated carboxylic acids such as acrylic acid, methacrylic acid, maleic acid, and itaconic acid. Particularly preferred monomers are acrylic acid and methacrylic acid. Very particular preference is given to acrylic acid.

Further suitable monomers a) are, for example, ethylenically unsaturated sulfonic acids such as vinylsulfonic acid, styrenesulfonic acid and 2-acrylamido-2-methylpropanesulfonic acid (AMPS).

Impurities may have a strong impact on the polymerization. Preference is given to especially purified monomers a). Useful purification methods are disclosed in WO 2002/055469 A1, WO 2003/078378 A1 and WO 2004/035514 A1. A suitable monomer a) is according to WO 2004/035514 A1 purified acrylic acid having 99.8460% by weight of acrylic acid, 0.0950% by weight of acetic acid, 0.0332% by weight of water, 0.0203 by weight of propionic acid, 0.0001% by weight of furfurals, 0.0001% by weight of maleic anhydride, 0.0003% by weight of diacrylic acid and 0.0050% by weight of hydroquinone monomethyl ether.

Polymerized diacrylic acid is a source for residual monomers due to thermal decomposition. If the temperatures during the process are low, the concentration of diacrylic acid is no more critical and acrylic acids having higher concentrations of diacrylic acid, i.e. 500 to 10,000 ppm, can be used for the inventive process.

The content of acrylic acid and/or salts thereof in the total amount of monomers a) is preferably at least 50 mol %, more preferably at least 90 mol %, most preferably at least 95 mol %.

The acid groups of the monomers a) are typically partly neutralized in the range of 0 to 100 mol %, preferably to an extent of from 25 to 85 mol %, preferentially to an extent of from 50 to 80 mol %, more preferably from 60 to 75 mol %, for which the customary neutralizing agents can be used, preferably alkali metal hydroxides, alkali metal oxides, alkali metal carbonates or alkali metal hydrogen carbonates, and mixtures thereof. Instead of alkali metal salts, it is also possible to use ammonia or organic amines, for example, triethanolamine. It is also possible to use oxides, carbonates, hydrogencarbonates and hydroxides of magnesium, calcium, strontium, zinc or aluminum as powders, slurries or solutions and mixtures of any of the above neutralization agents. Example for a mixture is a solution of sodiumaluminate. Sodium and potassium are particularly preferred as alkali metals, but very particular preference is given to sodium hydroxide, sodium carbonate or sodium hydrogen carbonate, and mixtures thereof. Typically, the neutralization is achieved by mixing in the neutralizing agent as an aqueous solution, as a melt or preferably also as a solid. For example, sodium hydroxide with water content significantly below 50% by weight may be present as a waxy material having a melting point above 23° C. In this case, metered addition as piece material or melt at elevated temperature is possible.

Optionally, it is possible to add to the monomer solution, or to starting materials thereof, one or more chelating agents for masking metal ions, for example iron, for the purpose of stabilization. Suitable chelating agents are, for example, alkali metal citrates, citric acid, alkali metal tartrates, alkali metal lactates and glycolates, pentasodium triphosphate, ethylenediamine tetraacetate, nitrilotriacetic acid, and all chelating agents known under the Trilon® name, for example Trilon® C (pentasodium diethylenetriaminepentaacetate), Trilon® D (trisodium (hydroxyethyl)-ethylenediaminetriacetate), and Trilon® M (methylglycinediacetic acid).

The monomers a) comprise typically polymerization inhibitors, preferably hydroquinone monoethers, as inhibitor for storage.

The monomer solution comprises preferably up to 250 ppm by weight, more preferably not more than 130 ppm by weight, most preferably not more than 70 ppm by weight, preferably not less than 10 ppm by weight, more preferably not less than 30 ppm by weight and especially about 50 ppm by weight of hydroquinone monoether, based in each case on acrylic acid, with acrylic acid salts being counted as acrylic acid. For example, the monomer solution can be prepared using acrylic acid having appropriate hydroquinone monoether content. The hydroquinone monoethers may, however, also be removed from the monomer solution by absorption, for example on activated carbon.

Preferred hydroquinone monoethers are hydroquinone monomethyl ether (MEHQ) and/or alpha-tocopherol (vitamin E).

Suitable crosslinkers b) are compounds having at least two groups suitable for crosslinking. Such groups are, for example, ethylenically unsaturated groups which can be polymerized by a free-radical mechanism into the polymer chain and functional groups which can form covalent bonds with the acid groups of monomer a). In addition, polyvalent metal ions which can form coordinate bond with at least two acid groups of monomer a) are also suitable crosslinkers b).

The crosslinkers b) are preferably compounds having at least two free-radically polymerizable groups which can be polymerized by a free-radical mechanism into the polymer network. Suitable crosslinkers b) are, for example, ethylene glycol dimethacrylate, diethylene glycol diacrylate, polyethylene glycol diacrylate, allyl methacrylate, trimethylolpropane triacrylate, triallylamine, tetraallylammonium chloride, tetraallyloxyethane, as described in EP 0 530 438 A1, di- and tri-acrylates, as described in EP 0 547 847 A1, EP 0 559 476 A1, EP 0 632 068 A1, WO 93/21237 A1, WO 2003/104299 A1, WO 2003/104300 A1, WO 2003/104301 A1 and in DE 103 31 450 A1, mixed acrylates which, as well as acrylate groups, comprise further ethylenically unsaturated groups, as described in DE 103 314 56 A1 and DE 103 55 401 A1, or crosslinker mixtures, as described, for example, in DE 195 43 368 A1, DE 196 46 484 A1, WO 90/15830 A1 and WO 2002/32962 A2.

Suitable crosslinkers b) are in particular pentaerythritol triallyl ether, tetraallyloxyethane, polyethyleneglycole diallylethers (based on polyethylene glycole having a molecular weight between 400 and 20000 g/mol), N,N'-methylenebisacrylamide, 15-tuply ethoxylated trimethylolpropane, polyethylene glycol diacrylate, trimethylolpropane triacrylate and triallylamine.

Very particularly preferred crosslinkers b) are the polyethoxylated and/or -propoxylated glycerols which have been esterified with acrylic acid or methacrylic acid to give di- or triacrylates, as described for example in WO 2003/104301 A1. Di- and/or triacrylates of 3- to 18-tuply ethoxylated glycerol are particularly advantageous. Very particular preference is given to di- or triacrylates of 1- to 5-tuply ethoxylated and/or propoxylated glycerol. Most preferred are the triacrylates of 3- to 5-tuply ethoxylated and/or propoxylated glycerol and especially the triacrylate of 3-tuply ethoxylated glycerol.

The amount of crosslinker b) is preferably from 0.0001 to 0.6% by weight, more preferably from 0.001 to 0.2% by weight, most preferably from 0.01 to 0.06% by weight, based in each case on monomer a). On increasing the amount of crosslinker b) the centrifuge retention capacity (CRC) decreases and the absorption under a pressure of 21.0 g/cm$^2$ (AUL) passes through a maximum.

The surface-postcrosslinked polymer particles of the present invention surprisingly require very little or even no cross-linker during the polymerization step. So, in one particularly preferred embodiment of the present invention no crosslinker b) is used.

The initiators c) used may be all compounds which disintegrate into free radicals under the polymerization conditions, for example peroxides, hydroperoxides, hydrogen peroxide, persulfates, azo compounds and redox initiators. Preference is given to the use of water-soluble initiators. In some cases, it is advantageous to use mixtures of various initiators, for example mixtures of hydrogen peroxide and sodium or potassium peroxodisulfate. Mixtures of hydrogen peroxide and sodium peroxodisulfate can be used in any proportion.

Particularly preferred initiators c) are azo initiators such as 2,2'-azobis[2-(2-imidazolin-2-yl)propane] dihydrochloride and 2,2'-azobis[2-(5-methyl-2-imidazolin-2-yl)propane] dihydrochloride, 2,2'-azobis(2-amidinopropane) dihydrochloride, 4,4'-azobis(4-cyanopentanoic acid), 4,4'-azobis (4-cyanopentanoic acid) sodium salt, 2,2'-azobis[2-methyl-N-(2-hydroxyethyl)propionamide], and photoinitiators such as 2-hydroxy-2-methylpropiophenone and 1-[4-(2-hydroxyethoxy)phenyl]-2-hydroxy-2-methyl-1-propan-1-one, redox initiators such as sodium persulfate/hydroxymethylsulfinic acid, ammonium peroxodisulfate/hydroxymethylsulfinic acid, hydrogen peroxide/hydroxymethylsulfinic acid, sodium persulfate/ascorbic acid, ammonium peroxodisulfate/ascorbic acid and hydrogen peroxide/ascorbic acid, photoinitiators such as 1-[4-(2-hydroxyethoxy)phenyl]-2-hydroxy-2-methyl-1-propan-1-one, and mixtures thereof. The reducing component used is, however, preferably a mixture of the sodium salt of 2-hydroxy-2-sulfinatoacetic acid, the disodium salt of 2-hydroxy-2-sulfonatoacetic acid and sodium bisulfite. Such mixtures are obtainable as Bruggolite® FF6 and Bruggolite® FF7 (Brüggemann Chemicals; Heilbronn; Germany). Of course it is also possible within the scope of the present invention to use the purified salts or acids of 2-hydroxy-2-sulfinatoacetic acid and 2-hydroxy-2-sulfonatoacetic acid—the latter being available as sodium salt under the trade name Blancolen® (Brüggemann Chemicals; Heilbronn; Germany).

The initiators are used in customary amounts, for example in amounts of from 0.001 to 5% by weight, preferably from 0.01 to 2% by weight, most preferably from 0.05 to 0.5% by weight, based on the monomers a).

Examples of ethylenically unsaturated monomers d) which are copolymerizable with the monomers a) are acrylamide, methacrylamide, hydroxyethyl acrylate, hydroxyethyl methacrylate, dimethylaminoethyl acrylate, dimethylaminoethyl methacrylate, dimethylaminopropyl acrylate and diethylaminopropyl methacrylate.

Useful water-soluble polymers e) include polyvinyl alcohol, modified polyvinyl alcohol comprising acidic side groups for example Poval® K (Kuraray Europe GmbH; Frankfurt; Germany), polyvinylpyrrolidone, starch, starch derivatives, modified cellulose such as methylcellulose, carboxymethylcellulose or hydroxyethylcellulose, gelatin, polyglycols or polyacrylic acids, polyesters and polyamides, polylactic acid, polyglycolic acid, co-polylactic-polyglycolic acid, polyvinylamine, polyallylamine, water soluble copolymers of acrylic acid and maleic acid available as Sokalan® (BASF SE; Ludwigshafen; Germany), preferably starch, starch derivatives and modified cellulose.

For optimal action, the preferred polymerization inhibitors require dissolved oxygen. Therefore, the monomer solution can be freed of dissolved oxygen before the polymerization by inertization, i.e. flowing through with an inert gas, preferably nitrogen. It is also possible to reduce the concentration of dissolved oxygen by adding a reducing agent. The oxygen content of the monomer solution is preferably lowered before the polymerization to less than 1 ppm by weight, more preferably to less than 0.5 ppm by weight.

The water content of the monomer solution is preferably less than 65% by weight, preferentially less than 62% by weight, more preferably less than 60% by weight, most preferably less than 58% by weight.

The monomer solution has, at 20° C., a dynamic viscosity of preferably from 0.002 to 0.02 Pa·s, more preferably from 0.004 to 0.015 Pas, most preferably from 0.005 to 0.01 Pa-s. The mean droplet diameter in the droplet generation rises with rising dynamic viscosity.

The monomer solution has, at 20° C., a density of preferably from 1 to 1.3 g/cm$^3$, more preferably from 1.05 to 1.25 g/cm$^3$, most preferably from 1.1 to 1.2 g/cm$^3$.

The monomer solution has, at 20° C., a surface tension of from 0.02 to 0.06 N/m, more preferably from 0.03 to 0.05 N/m, most preferably from 0.035 to 0.045 N/m. The mean droplet diameter in the droplet generation rises with rising surface tension.

Polymerization

The monomer solution is polymerized. Suitable reactors are, for example, kneading reactors or belt reactors. In the kneader, the polymer gel formed in the polymerization of an aqueous monomer solution or suspension is comminuted continuously by, for example, contrarotatory stirrer shafts, as described in WO 2001/038402 A1. Polymerization on the belt is described, for example, in DE 38 25 366 A1 and U.S. Pat. No. 6,241,928. Polymerization in a belt reactor forms a polymer gel which has to be comminuted in a further process step, for example in an extruder or kneader.

To improve the drying properties, the comminuted polymer gel obtained by means of a kneader can additionally be extruded.

In a preferred embodiment of the present invention the water-absorbent polymer particles are produced by polymerizing droplets of the monomer in a surrounding heated gas phase, for example using a system described in WO 2008/040715 A2, WO 2008/052971 A1, WO 2008/069639 A1 and WO 2008/086976 A1.

The droplets are preferably generated by means of a droplet plate. A droplet plate is a plate having a multitude of bores, the liquid entering the bores from the top. The droplet plate or the liquid can be oscillated, which generates a chain of ideally monodisperse droplets at each bore on the underside of the droplet plate. In a preferred embodiment, the droplet plate is not agitated.

Within the scope of the present invention it is also possible to use two or more droplet plates with different bore diameters so that a range of desired particle sizes can be produced. It is preferable that each droplet plate carries only one bore diameter, however mixed bore diameters in one plate are also possible.

The number and size of the bores are selected according to the desired capacity and droplet size. The droplet diameter is typically 1.9 times the diameter of the bore. What is important here is that the liquid to be dropletized does not pass through the bore too rapidly and the pressure drop over the bore is not too great. Otherwise, the liquid is not dropletized, but rather the liquid jet is broken up (sprayed) owing to the high kinetic energy. The Reynolds number based on the throughput per bore and the bore diameter is preferably less than 2000, preferentially less than 1600, more preferably less than 1400 and most preferably less than 1200.

The underside of the droplet plate has at least in part a contact angle preferably of at least 60°, more preferably at least 75° and most preferably at least 90° with regard to water.

The contact angle is a measure of the wetting behavior of a liquid, in particular water, with regard to a surface, and can be determined using conventional methods, for example in accordance with ASTM D 5725. A low contact angle denotes good wetting, and a high contact angle denotes poor wetting.

It is also possible for the droplet plate to consist of a material having a lower contact angle with regard to water, for example a steel having the German construction material code number of 1.4571, and be coated with a material having a larger contact angle with regard to water.

Useful coatings include for example fluorous polymers, such as perfluoroalkoxyethylene, polytetrafluoroethylene, ethylene-chlorotrifluoroethylene copolymers, ethylene-tetrafluoroethylene copolymers and fluorinated polyethylene.

The coatings can be applied to the substrate as a dispersion, in which case the solvent is subsequently evaporated off and the coating is heat treated. For polytetrafluoroethylene this is described for example in U.S. Pat. No. 3,243,321.

Further coating processes are to be found under the headword "Thin Films" in the electronic version of "Ullmann's Encyclopedia of Industrial Chemistry" (Updated Sixth Edition, 2000 Electronic Release).

The coatings can further be incorporated in a nickel layer in the course of a chemical nickelization.

It is the poor wettability of the droplet plate that leads to the production of monodisperse droplets of narrow droplet size distribution.

The droplet plate has preferably at least 5, more preferably at least 25, most preferably at least 50 and preferably up to 750, more preferably up to 500 bores, most preferably up to 250. The number of bores is determined mainly by geometrical and manufacturing constraints and can be adjusted to practical use conditions even outside the above given range. The diameter of the bores is adjusted to the desired droplet size.

The separation of the bores is usually from 5 to 50 mm, preferably from 6 to 40 mm, more preferably from 7 to 35 mm, most preferably from 8 to 30 mm. Smaller separations of the bores may cause agglomeration of the polymerizing droplets.

The diameter of the bores is preferably from 50 to 500 μm, more preferably from 100 to 300 μm, most preferably from 150 to 250 μm.

For optimizing the average particle diameter, droplet plates with different bore diameters can be used. The variation can be done by different bores on one plate or by using different plates, where each plate has a different bore diameter. The average particle size distribution can be monomodal, bimodal or multimodal. Most preferably it is monomodal or bimodal.

The temperature of the monomer solution as it passes through the bore is preferably from 5 to 80° C., more preferably from 10 to 70° C., most preferably from 30 to 60° C.

A gas flows through the reaction chamber. The carrier gas is conducted through the reaction chamber in cocurrent to the free-falling droplets of the monomer solution, i.e. from the top downward. After one pass, the gas is preferably recycled at least partly, preferably to an extent of at least 50%, more preferably to an extent of at least 75%, into the reaction chamber as cycle gas. Typically, a portion of the carrier gas is discharged after each pass, preferably up to 10%, more preferably up to 3% and most preferably up to 1%.

The carrier gas may be composed of air. The oxygen content of the carrier gas is preferably from 0.1 to 15% by volume, more preferably from 1 to 10% by volume, most preferably from 2 to 7% by weight. In the scope of the present invention it is also possible to use a carrier gas which is free of oxygen.

As well as oxygen, the carrier gas preferably comprises nitrogen. The nitrogen content of the gas is preferably at least 80% by volume, more preferably at least 90% by volume, most preferably at least 95% by volume. Other possible carrier gases may be selected from carbon dioxide, argon, xenon, krypton, neon, helium, sulfurhexafluoride. Any mixture of carrier gases may be used. The carrier gas may also become loaded with water and/or acrylic acid vapors.

The gas velocity is preferably adjusted such that the flow in the reaction zone is directed, for example no convection currents opposed to the general flow direction are present, and is preferably from 0.1 to 2.5 m/s, more preferably from 0.3 to 1.5 m/s, even more preferably from 0.5 to 1.2 m/s, most preferably from 0.7 to 0.9 m/s.

The gas entrance temperature, i.e. the temperature with which the gas enters the reaction zone, is preferably from 160 to 200° C., more preferably from 165 to 195° C., even more preferably from 170 to 190° C., most preferably from 175 to 185° C.

The steam content of the gas that enters the reaction zone is preferably from 0.01 to 0.15 kg per kg dry gas, more preferably from 0.02 to 0.12 kg per kg dry gas, most preferably from 0.03 to 0.10 kg per kg dry gas.

The gas entrance temperature is controlled in such a way that the gas exit temperature, i.e. the temperature with which the gas leaves the reaction zone, is less than 150° C., preferably from 90 to 140° C., more preferably from 100 to 130° C., even more preferably from 105 to 125° C., most preferably from 110 to 120° C.

The steam content of the gas that leaves the reaction zone is preferably from 0.02 to 0.30 kg per kg dry gas, more from 0.04 to 0.28 kg per kg dry gas, most from 0.05 to 0.25 kg per kg dry gas.

The water-absorbent polymer particles can be divided into three categories: water-absorbent polymer particles of Type 1 are particles with one cavity, water-absorbent polymer particles of Type 2 are particles with more than one cavity, and water-absorbent polymer particles of Type 3 are solid particles with no visible cavity. Type 1 particles are represented by hollow-spheres, Type 2 particles are represented by spherical closed cell sponges, and Type 3 particles are represented by solid spheres. Type 2 or Type 3 particles or mixtures thereof with little or no Type 1 particles are preferred.

The morphology of the water-absorbent polymer particles can be controlled by the reaction conditions during polymerization. Water-absorbent polymer particles having a high amount of particles with one cavity (Type 1) can be prepared by using low gas velocities and high gas exit temperatures. Water-absorbent polymer particles having a high amount of particles with more than one cavity (Type 2) can be prepared by using high gas velocities and low gas exit temperatures.

Water-absorbent polymer particles having no cavity (Type 3) and water-absorbent polymer particles having more than one cavity (Type 2) show an improved mechanical stability compared with water-absorbent polymer particles having only one cavity (Type 1).

As a particular advantage round shaped particles have no edges that can easily be broken by processing stress in diaper production and during swelling in aqueous liquid there are no breakpoints on the surface that could lead to loss of mechanical strength.

The reaction can be carried out under elevated pressure or under reduced pressure, preferably from 1 to 100 mbar below ambient pressure, more preferably from 1.5 to 50 mbar below ambient pressure, most preferably from 2 to 10 mbar below ambient pressure.

The reaction off-gas, i.e. the gas leaving the reaction chamber, may be cooled in a heat exchanger. This condenses water and unconverted monomer a). The reaction off-gas can then be reheated at least partly and recycled into the reaction chamber as cycle gas. A portion of the reaction off-gas can be discharged and replaced by fresh gas, in which case water and unconverted monomers a) present in the reaction off-gas can be removed and recycled.

Particular preference is given to a thermally integrated system, i.e. a portion of the waste heat in the cooling of the off-gas is used to heat the cycle gas.

The reactors can be trace-heated. In this case, the trace heating is adjusted such that the wall temperature is at least 5° C. above the internal reactor temperature and condensation on the reactor walls is reliably prevented.

Thermal Posttreatment

The water-absorbent polymer particles obtained by dropletization may be thermal posttreated for adjusting the content of residual monomers to the desired value.

The residual monomers can be removed better at relatively high temperatures and relatively long residence times. What is important here is that the water-absorbent polymer particles are not too dry. In the case of excessively dry particles, the residual monomers decrease only insignificantly. Too high a water content increases the caking tendency of the water-absorbent polymer particles.

The thermal posttreatment can be done in a fluidized bed. In a preferred embodiment of the present invention an internal fluidized bed is used. An internal fluidized bed means that the product of the dropletization polymerization is accumulated in a fluidized bed below the reaction zone.

In the fluidized state, the kinetic energy of the polymer particles is greater than the cohesion or adhesion potential between the polymer particles.

The fluidized state can be achieved by a fluidized bed. In this bed, there is upward flow toward the water-absorbing polymer particles, so that the particles form a fluidized bed. The height of the fluidized bed is adjusted by gas rate and gas velocity, i.e. via the pressure drop of the fluidized bed (kinetic energy of the gas).

The velocity of the gas stream in the fluidized bed is preferably from 0.3 to 2.5 m/s, more preferably from 0.4 to 2.0 m/s, most preferably from 0.5 to 1.5 m/s.

The pressure drop over the bottom of the internal fluidized bed is preferably from 1 to 100 mbar, more preferably from 3 to 50 mbar, most preferably from 5 to 25 mbar.

The moisture content of the water-absorbent polymer particles at the end of the thermal posttreatment is preferably from 1 to 20% by weight, more preferably from 2 to 15% by weight, even more preferably from 3 to 12% by weight, most preferably 5 to 8% by weight.

The temperature of the water-absorbent polymer particles during the thermal posttreatment is from 20 to 120° C., preferably from 40 to 100° C., more preferably from 50 to 95° C., even more preferably from 55 to 90° C., most preferably from 60 to 80° C.

The average residence time in the internal fluidized bed is from 10 to 300 minutes, preferably from 60 to 270 minutes, more preferably from 40 to 250 minutes, most preferably from 120 to 240 minutes.

The condition of the fluidized bed can be adjusted for reducing the amount of residual monomers of the water-absorbent polymers leaving the fluidized bed. The amount of residual monomers can be reduced to levels below 0.1% by weight by a thermal posttreatment using additional steam.

The steam content of the gas is preferably from 0.005 to 0.25 kg per kg of dry gas, more preferably from 0.01 to 0.2 kg per kg of dry gas, most preferably from 0.02 to 0.15 kg per kg of dry gas. By using additional steam the condition of the fluidized bed can be adjusted that the amount of residual monomers of the water-absorbent polymers leaving the fluidized bed is from 0.03 to 15% by weight, preferably from 0.05 to 12% by weight, more preferably from 0.1 to 10% by weight, even more preferably from 0.15 to 7.5% by weight most preferably from 0.2 to 5% by weight, even most preferably from 0.25 to 2.5% by weight.

The level of residual monomers in the water-absorbent polymer has in important impact on the properties of the later formed surface-postcrosslinked water-absorbent polymer particles. That means that very low levels of residual monomers must be avoided.

In one preferred embodiment of the present invention the thermal posttreatment is completely or at least partially done in an external fluidized bed. The operating conditions of the external fluidized bed are within the scope for the internal fluidized bed as described above.

In another preferred embodiment of the present invention the thermal posttreatment is done in an external mixer with moving mixing tools, preferably horizontal mixers, such as screw mixers, disk mixers, screw belt mixers and paddle mixers. Suitable mixers are, for example, Becker shovel mixers (Gebr. Lödige Maschinenbau GmbH; Paderborn; Germany), Nara paddle mixers (NARA Machinery Europe; Frechen; Germany), Pflugschar® plowshare mixers (Gebr. Lödige Maschinenbau GmbH; Paderborn; Germany), Vrieco-Nauta Continuous Mixers (Hosokawa Micron BV; Doetinchem; the Netherlands), Processall Mixmill Mixers (Processall Incorporated; Cincinnati; U.S.A.) and Ruberg continuous flow mixers (Gebrüder Ruberg GmbH & Co KG, Nieheim, Germany). Ruberg continuous flow mixers, Becker shovel mixers and Pflugschar® plowshare mixers are preferred.

The thermal posttreatment can be done in a discontinuous external mixer or a continuous external mixer.

The amount of gas to be used in the discontinuous external mixer is preferably from 0.01 to 5 $Nm^3/h$, more preferably from 0.05 to 2 $Nm^3/h$, most preferably from 0.1 to 0.5 $Nm^3/h$, based in each case on kg water-absorbent polymer particles.

The amount of gas to be used in the continuous external mixer is preferably from 0.01 to 5 $Nm^3/h$, more preferably from 0.05 to 2 $Nm^3/h$, most preferably from 0.1 to 0.5 $Nm^3/h$, based in each case on kg/h throughput of water-absorbent polymer particles.

The other constituents of the gas are preferably nitrogen, carbon dioxide, argon, xenon, krypton, neon, helium, air or air/nitrogen mixtures, more preferably nitrogen or air/nitrogen mixtures comprising less than 10% by volume of oxygen. Oxygen may cause discoloration.

The morphology of the water-absorbent polymer particles can also be controlled by the reaction conditions during thermal posttreatment. Water-absorbent polymer particles having a high amount of particles with one cavity (Type 1) can be prepared by using high product temperatures and short residence times. Water-absorbent polymer particles having a high amount of particles with more than one cavity (Type 2) can be prepared by using low product temperatures and long residence times.

Surface-Postcrosslinking

In the present invention the polymer particles are surface-postcrosslinked for further improvement of the properties.

Surface-postcrosslinkers are compounds which comprise groups which can form at least two covalent bonds with the carboxylate groups of the polymer particles. Suitable compounds are, for example, polyfunctional amines, polyfunctional amidoamines, polyfunctional epoxides, as described in EP 0 083 022 A2, EP 0 543 303 A1 and EP 0 937 736 A2, di- or polyfunctional alcohols as described in DE 33 14 019 A1, DE 35 23 617 A1 and EP 0 450 922 A2, or β-hydroxyalkylamides, as described in DE 102 04 938 A1 and U.S. Pat. No. 6,239,230. Also ethyleneoxide, aziridine, glycidol, oxetane and its derivatives may be used.

Polyvinylamine, polyamidoamines and polyvinylalcohole are examples of multifunctional polymeric surface-postcrosslinkers.

In addition, DE 40 20 780 C1 describes alkylene carbonates, DE 198 07 502 A1 describes 1,3-oxazolidin-2-one and its derivatives such as 2-hydroxyethyl-1,3-oxazolidin-2-one, DE 198 07 992 C1 describes bis- and poly-1,3-oxazolidin-2-ones, EP 0 999 238 A1 describes bis- and poly-1,3-oxazolidines, DE 198 54 573 A1 describes 2-oxotetrahydro-1,3-oxazine and its derivatives, DE 198 54 574 A1 describes N-acyl-1,3-oxazolidin-2-ones, DE 102 04 937 A1 describes cyclic ureas, DE 103 34 584 A1 describes bicyclic amide acetals, EP 1199 327 A2 describes oxetanes and cyclic ureas, and WO 2003/31482 A1 describes morpholine-2,3-dione and its derivatives, as suitable surface-postcrosslinkers.

In addition, it is also possible to use surface-postcrosslinkers which comprise additional polymerizable ethylenically unsaturated groups, as described in DE 37 13 601 A1.

In a preferred embodiment of the present invention the at least one surface-postcrosslinker is selected from alkylene carbonates, 1,3-oxazolidin-2-ones, bis- and poly-1,3-oxazolidin-2-ones, bis- and poly-1,3-oxazolidines, 2-oxotetrahydro-1,3-oxazines, N-acyl-1,3-oxazolidin-2-ones, cyclic ureas, bicyclic amide acetals, oxetanes, and morpholine-2,3-diones. Suitable surface-postcrosslinkers are ethylene carbonate, 3-methyl-1,3-oxazolidin-2-one, 3-methyl-3-oxethanmethanol, 1,3-oxazolidin-2-one, 3-(2-hydroxyethyl)-1,3-oxazolidin-2-one, 1,3-dioxan-2-one or a mixture thereof.

It is also possible to use any suitable mixture of surface-postcrosslinkers. It is particularly favorable to use mixtures of 1,3-dioxolan-2-on (ethylene carbonate) and 1,3-oxazolidin-2-ones. Such mixtures are obtainable by mixing and partly reacting of 1,3-dioxolan-2-on (ethylene carbonate) with the corresponding 2-amino-alcohol (e.g. 2-aminoethanol) and may comprise ethylene glycol from the reaction.

In a more preferred embodiment of the present invention at least one alkylene carbonate is used as surface-postcrosslinker. Suitable alkylene carbonates are 1,3-dioxolan-2-on (ethylene carbonate), 4-methyl-1,3-dioxolan-2-on (propylene carbonate), 4,5-dimethyl-1,3-dioxolan-2-on, 4,4-dimethyl-1,3-dioxolan-2-on, 4-ethyl-1,3-dioxolan-2-on, 4-hydroxymethyl-1,3-dioxolan-2-on (glycerine carbonate), 1,3-dioxane-2-on (trimethylene carbonate), 4-methyl-1,3-dioxane-2-on, 4,6-dimethyl-1,3-dioxane-2-on and 1,3-dioxepan-2-on, preferably 1,3-dioxolan-2-on (ethylene carbonate) and 1,3-dioxane-2-on (trimethylene carbonate), most preferably 1,3-dioxolan-2-on (ethylene carbonate).

The amount of surface-postcrosslinker is preferably from 0.1 to 10% by weight, more preferably from 0.5 to 7.5% by weight, most preferably from 1 to 5% by weight, based in each case on the polymer.

The content of residual monomers in the water-absorbent polymer particles prior to the coating with the surface-postcrosslinker is in the range from 0.03 to 15% by weight, preferably from 0.05 to 12% by weight, more preferably from 0.1 to 10% by weight, even more preferably from 0.15 to 7.5% by weight, most preferably from 0.2 to 5% by weight, even most preferably from 0.25 to 2.5% by weight.

The moisture content of the water-absorbent polymer particles prior to the thermal surface-postcrosslinking is preferably from 1 to 20% by weight, more preferably from 2 to 15% by weight, most preferably from 3 to 10% by weight.

In a preferred embodiment of the present invention, polyvalent cations are applied to the particle surface in addition to the surface-postcrosslinkers before, during or after the thermal surface-postcrosslinking.

The polyvalent cations usable in the process according to the invention are, for example, divalent cations such as the cations of zinc, magnesium, calcium, iron and strontium, trivalent cations such as the cations of aluminum, iron, chromium, rare earths and manganese, tetravalent cations such as the cations of titanium and zirconium, and mixtures thereof. Possible counterions are chloride, bromide, sulfate, hydrogensulfate, methanesulfate, carbonate, hydrogencarbonate, nitrate, hydroxide, phosphate, hydrogenphosphate, dihydrogenphosphate, glycophosphate and carboxylate, such as acetate, glycolate, tartrate, formiate, propionate, 3-hydroxypropionate, lactamide and lactate, and mixtures thereof. Aluminum sulfate, aluminum acetate, and aluminum lactate are preferred. Aluminum lactate is more preferred. Using the inventive process in combination with the use of aluminum lactate, water-absorbent polymer particles having an extremely high total liquid uptake at lower centrifuge retention capacities (CRC) can be prepared.

Apart from metal salts, it is also possible to use polyamines and/or polymeric amines as polyvalent cations. A single metal salt can be used as well as any mixture of the metal salts and/or the polyamines above.

Preferred polyvalent cations and corresponding anions are disclosed in WO 2012/045705 A1 and are expressly incorporated herein by reference. Preferred polyvinylamines are disclosed in WO 2004/024816 A1 and are expressly incorporated herein by reference.

The amount of polyvalent cation used is, for example, from 0.001 to 1.5% by weight, preferably from 0.005 to 1% by weight, more preferably from 0.02 to 0.8% by weight, based in each case on the polymer.

The addition of the polyvalent metal cation can take place prior, after, or cocurrently with the surface-postcrosslinking. Depending on the formulation and operating conditions employed it is possible to obtain a homogeneous surface coating and distribution of the polyvalent cation or an inhomogenous typically spotty coating. Both types of coatings and any mixes between them are useful within the scope of the present invention.

The surface-postcrosslinking is typically performed in such a way that a solution of the surface-postcrosslinker is sprayed onto the hydrogel or the dry polymer particles. After the spraying, the polymer particles coated with the surface-postcrosslinker are dried thermally and cooled.

The spraying of a solution of the surface-postcrosslinker is preferably performed in mixers with moving mixing tools, such as screw mixers, disk mixers and paddle mixers. Suitable mixers are, for example, vertical Schugi Flexomix® mixers (Hosokawa Micron BV; Doetinchem; the Netherlands), Turbolizers® mixers (Hosokawa Micron BV; Doetinchem; the Netherlands), horizontal Pflugschar® plowshare mixers (Gebr. Lödige Maschinenbau GmbH; Paderborn; Germany), Vrieco-Nauta Continuous Mixers (Hosokawa Micron BV; Doetinchem; the Netherlands), Processall Mixmill Mixers (Processall Incorporated; Cincinnati; US) and Ruberg continuous flow mixers (Gebrüder Ruberg GmbH & Co KG, Nieheim, Germany). Ruberg continuous flow mixers and horizontal Pflugschar® plowshare mixers are preferred. The surface-postcrosslinker solution can also be sprayed into a fluidized bed.

The solution of the surface-postcrosslinker can also be sprayed on the water-absorbent polymer particles during the thermal posttreatment. In such case the surface-postcrosslinker can be added as one portion or in several portions along the axis of thermal posttreatment mixer. In one embodiment it is preferred to add the surface-postcrosslinker at the end of the thermal post-treatment step. As a particular advantage of adding the solution of the surface-postcrosslinker during the thermal posttreatment step it may be possible to eliminate or reduce the technical effort for a separate surface-postcrosslinker addition mixer.

The surface-postcrosslinkers are typically used as an aqueous solution. The addition of nonaqueous solvent can be used to improve surface wetting and to adjust the penetration depth of the surface-postcrosslinker into the polymer particles.

The thermal surface-postcrosslinking is preferably carried out in contact dryers, more preferably paddle dryers, most preferably disk dryers. Suitable driers are, for example, Hosokawa Bepex® horizontal paddle driers (Hosokawa Micron GmbH; Leingarten; Germany), Hosokawa Bepex® disk driers (Hosokawa Micron GmbH; Leingarten; Germany), Holo-Flite® dryers (Metso Minerals Industries Inc.; Danville; U.S.A.) and Nara paddle driers (NARA Machinery Europe; Frechen; Germany). Moreover, it is also possible to use fluidized bed dryers. In the latter case the reaction times may be shorter compared to other embodiments.

When a horizontal dryer is used then it is often advantageous to set the dryer up with an inclined angle of a few degrees vs. the earth surface in order to impart proper product flow through the dryer. The angle can be fixed or may be adjustable and is typically between 0 to 10 degrees, preferably 1 to 6 degrees, most preferably 2 to 4 degrees.

In one embodiment of the present invention a contact dryer is used that has two different heating zones in one apparatus. For example Nara paddle driers are available with just one heated zone or alternatively with two heated zones. The advantage of using a two or more heated zone dryer is that different phases of the thermal post-treatment and/or of the post-surface-crosslinking can be combined.

In one preferred embodiment of the present invention a contact dryer with a hot first heating zone is used which is followed by a temperature holding zone in the same dryer. This set up allows a quick rise of the product temperature and evaporation of surplus liquid in the first heating zone, whereas the rest of the dryer is just holding the product temperature stable to complete the reaction.

In another preferred embodiment of the present invention a contact dryer with a warm first heating zone is used which is then followed by a hot heating zone. In the first warm zone the thermal post-treatment is affected or completed whereas the surface-postcrosslinking takes place in the subsequential hot zone.

In a typical embodiment a paddle heater with just one temperature zone is employed.

A person skilled in the art will depending on the desired finished product properties and the available base polymer qualities from the polymerization step choose any one of these set ups. The thermal surface-postcrosslinking can be effected in the mixer itself, by heating the jacket, blowing in warm air or steam. Equally suitable is a downstream dryer, for example a shelf dryer, a rotary tube oven or a heatable screw. It is particularly advantageous to mix and dry in a fluidized bed dryer.

Preferred thermal surface-postcrosslinking temperatures are in the range from 100 to 180° C., preferably from 120 to 170° C., more preferably from 130 to 165° C., most preferably from 140 to 160° C. The preferred residence time at this temperature in the reaction mixer or dryer is preferably at least 5 minutes, more preferably at least 20 minutes, most preferably at least 40 minutes, and typically at most 120 minutes.

It is preferable to cool the polymer particles after thermal surface-postcrosslinking. The cooling is preferably carried out in contact coolers, more preferably paddle coolers, most preferably disk coolers. Suitable coolers are, for example, Hosokawa Bepex® horizontal paddle coolers (Hosokawa Micron GmbH; Leingarten; Germany), Hosokawa Bepex® disk coolers (Hosokawa Micron GmbH; Leingarten; Germany), Holo-Flite® coolers (Metso Minerals Industries Inc.; Danville; U.S.A.) and Nara paddle coolers (NARA Machinery Europe; Frechen; Germany). Moreover, it is also possible to use fluidized bed coolers.

In the cooler the polymer particles are cooled to temperatures in the range from 20 to 150° C., preferably from 40 to 120° C., more preferably from 60 to 100° C., most preferably from 70 to 90° C. Cooling using warm water is preferred, especially when contact coolers are used.

Coating

To improve the properties, the water-absorbent polymer particles can be coated and/or optionally moistened. The internal fluidized bed, the external fluidized bed and/or the external mixer used for the thermal posttreatment and/or a separate coater (mixer) can be used for coating of the water-absorbent polymer particles. Further, the cooler and/or a separate coater (mixer) can be used for coating/moistening of the surface-postcrosslinked water-absorbent polymer particles. Suitable coatings for controlling the acquisition behavior and improving the permeability (SFC or GBP) are, for example, inorganic inert substances, such as water-insoluble metal salts, organic polymers, cationic polymers, anionic polymers and polyvalent metal cations. Suitable coatings for improving the color stability are, for example reducing agents, chelating agents and anti-oxidants. Suitable coatings for dust binding are, for example, polyols. Suitable coatings against the undesired caking tendency of the polymer particles are, for example, fumed silica, such as Aerosil® 200, and surfactants, such as Span® 20 and Plantacare® 818 UP. Preferred coatings are aluminium dihydroxy monoacetate, aluminium sulfate, aluminium lactate, aluminium 3-hydroxypropionate, zirconium acetate, citric acid or its water soluble salts, di- and monophosphoric acid or their water soluble salts, Blancolen®, Brüggolite® FF7, Cublen®, Span® 20 and Plantacare® 818 UP.

If salts of the above acids are used instead of the free acids then the preferred salts are alkali-metal, earth alkali metal, aluminum, zirconium, titanium, zinc and ammonium salts.

Under the trade name Cublen® (Zschimmer & Schwarz Mohsdorf GmbH & Co KG; Burgstädt; Germany) the following acids and/or their alkali metal salts (preferably Na and K-salts) are available and may be used within the scope of the present invention for example to impart color-stability to the finished product:

1-Hydroxyethane-1,1-diphosphonic acid, Amino-tris (methylene phosphonic acid), Ethylenediamine-tetra(methylene phosphonic acid), Diethylenetriamine-penta(methylene phosphonic acid), Hexamethylene diamine-tetra (methylenephosphonic acid), Hydroxyethyl-amino-di (methylene phosphonic acid), 2-Phosphonobutane-1,2,4-tricarboxylic acid, Bis(hexamethylenetriamine penta (methylene phosphonic acid).

Most preferably 1-Hydroxyethane-1,1-diphosphonic acid or its salts with sodium, potassium, or ammonium are employed. Any mixture of the above Cublenes® can be used.

Alternatively, any of the chelating agents described before for use in the polymerization can be coated onto the finished product.

Suitable inorganic inert substances are silicates such as montmorillonite, kaolinite and talc, zeolites, activated carbons, polysilicic acids, magnesium carbonate, calcium carbonate, calcium phosphate, aluminum phosphate, barium sulfate, aluminum oxide, titanium dioxide and iron(II) oxide. Preference is given to using polysilicic acids, which are divided between precipitated silicas and fumed silicas according to their mode of preparation. The two variants are commercially available under the names Silica FK, Sipernat®, Wessalon® (precipitated silicas) and Aerosil® (fumed silicas) respectively. The inorganic inert substances may be used as dispersion in an aqueous or water-miscible dispersant or in substance.

When the water-absorbent polymer particles are coated with inorganic inert substances, the amount of inorganic inert substances used, based on the water-absorbent polymer particles, is preferably from 0.05 to 5% by weight, more preferably from 0.1 to 1.5% by weight, most preferably from 0.3 to 1% by weight.

Suitable organic polymers are polyalkyl methacrylates or thermoplastics such as polyvinyl chloride, waxes based on polyethylene, polypropylene, polyamides or polytetrafluoro-ethylene. Other examples are styrene-isoprene-styrene block-copolymers or styrene-butadiene-styrene block-copolymers. Another example are silanole-group bearing polyvinylalcoholes available under the trade name Poval® R (Kuraray Europe GmbH; Frankfurt; Germany).

Suitable cationic polymers are polyalkylenepolyamines, cationic derivatives of polyacrylamides, polyethyleneimines and polyquaternary amines.

Polyquaternary amines are, for example, condensation products of hexamethylenediamine, dimethylamine and epichlorohydrin, condensation products of dimethylamine and epichlorohydrin, copolymers of hydroxyethylcellulose and diallyldimethylammonium chloride, copolymers of acrylamide and α-methacryloyloxyethyltrimethylammonium chloride, condensation products of hydroxyethylcellulose, epichlorohydrin and trimethylamine, homopolymers of diallyldimethylammonium chloride and addition products of epichlorohydrin to amidoamines. In addition, polyquaternary amines can be obtained by reacting dimethyl sulfate with polymers such as polyethyleneimines, copolymers of vinylpyrrolidone and dimethylaminoethyl methacrylate or copolymers of ethyl methacrylate and diethylaminoethyl methacrylate. The polyquaternary amines are available within a wide molecular weight range.

However, it is also possible to generate the cationic polymers on the particle surface, either through reagents which can form a network with themselves, such as addition products of epichlorohydrin to polyamidoamines, or through the application of cationic polymers which can react with an added crosslinker, such as polyamines or polyimines in combination with polyepoxides, polyfunctional esters, polyfunctional acids or polyfunctional (meth)acrylates.

It is possible to use all polyfunctional amines having primary or secondary amino groups, such as polyethyleneimine, polyallylamine and polylysine. The liquid sprayed by the process according to the invention preferably comprises at least one polyamine, for example polyvinylamine or a partially hydrolyzed polyvinylformamide.

The cationic polymers may be used as a solution in an aqueous or water-miscible solvent as dispersion in an aqueous or water-miscible dispersant or in substance.

When the water-absorbent polymer particles are coated with a cationic polymer, the use amount of cationic polymer based on the water-absorbent polymer particles is usually not less than 0.001% by weight, typically not less than 0.01% by weight, preferably from 0.1 to 15% by weight, more preferably from 0.5 to 10% by weight, most preferably from 1 to 5% by weight.

Suitable anionic polymers are polyacrylates (in acidic form or partially neutralized as salt), copolymers of acrylic acid and maleic acid available under the trade name Sokalan® (BASF SE; Ludwigshafen; Germany), and polyvinylalcohols with built in ionic charges available under the trade name Poval® K (Kuraray Europe GmbH; Frankfurt; Germany).

Suitable polyvalent metal cations are $Mg^{2+}$, $Ca^{2+}$, $Al^{3+}$, $Sc^{3+}$, $Ti^{4+}$, $Mn^{2+}$, $Fe^{2+/3+}$, $Co^{2+}$, $Ni^{2+}$, $Cu^{+/2+}$, $Zn^{2+}$, $Y^{3+}$, $Zr^{4+}$, $Ag^+$, $La^{3+}$, $Ce^{4+}$, $Hf^{4+}$ and $Au^{+/3+}$; preferred metal cations are $Mg^{2+}$, $Ca^{2+}$, $Al^{3+}$, $Ti^{4+}$, $Zr^{4+}$ and $La^{3+}$; particularly preferred metal cations are $Al^{3+}$, $Ti^{4+}$ and $Zr^{4+}$. The metal cations may be used either alone or in a mixture with one another. Suitable metal salts of the metal cations mentioned are all of those which have a sufficient solubility in the solvent to be used. Particularly suitable metal salts have weakly complexing anions, such as chloride, hydroxide, carbonate, acetate, formiate, propionate, nitrate, sulfate and methanesulfate. The metal salts are preferably used as a solution or as a stable aqueous colloidal dispersion. The solvents used for the metal salts may be water, alcohols, ethylenecarbonate, propylenecarbonate, dimethylformamide, dimethyl sulfoxide and mixtures thereof. Particular preference is given to water and water/alcohol mixtures, such as water/methanol, water/isopropanol, water/1,3-propanediole, water/1,2-propandiole/1,4-butanediole or water/propylene glycol.

When the water-absorbent polymer particles are coated with a polyvalent metal cation, the amount of polyvalent metal cation used, based on the water-absorbent polymer particles, is preferably from 0.05 to 5% by weight, more preferably from 0.1 to 1.5% by weight, most preferably from 0.3 to 1% by weight.

Suitable reducing agents are, for example, sodium sulfite, sodium hydrogensulfite (sodium bisulfite), sodium dithionite, sulfinic acids and salts thereof, ascorbic acid, sodium hypophosphite, sodium phosphite, and phosphinic acids and salts thereof. Preference is given, however, to salts of hypophosphorous acid, for example sodium hypophosphite, salts of sulfinic acids, for example the disodium salt of 2-hydroxy-2-sulfinatoacetic acid, and addition products of aldehydes, for example the disodium salt of 2-hydroxy-2-sulfonatoacetic acid. The reducing agent used can be, however, a mixture of the sodium salt of 2-hydroxy-2-sulfinatoacetic acid, the disodium salt of 2-hydroxy-2-sulfonatoacetic acid and sodium bisulfite. Such mixtures are obtainable as Brüggolite® FF6 and Bruggolite® FF7 (Brüggemann Chemicals; Heilbronn; Germany). Also useful is the purified 2-hydroxy-2-sulfonatoacetic acid and its sodium salts, available under the trade name Blancolen® from the same company.

The reducing agents are typically used in the form of a solution in a suitable solvent, preferably water. The reducing agent may be used as a pure substance or any mixture of the above reducing agents may be used.

When the water-absorbent polymer particles are coated with a reducing agent, the amount of reducing agent used, based on the water-absorbent polymer particles, is preferably from 0.01 to 5% by weight, more preferably from 0.05 to 2% by weight, most preferably from 0.1 to 1% by weight.

Suitable polyols are polyethylene glycols having a molecular weight of from 400 to 20000 g/mol, polyglycerol, 3- to 100-tuply ethoxylated polyols, such as trimethylolpropane, glycerol, sorbitol, mannitol, inositol, pentaerythritol and neopentyl glycol. Particularly suitable polyols are 7- to 20-tuply ethoxylated glycerol or trimethylolpropane, for example Polyol TP 70® (Perstorp AB, Perstorp, Sweden). The latter have the advantage in particular that they lower the surface tension of an aqueous extract of the water-absorbent polymer particles only insignificantly. The polyols are preferably used as a solution in aqueous or water-miscible solvents.

The polyol can be added before, during, or after surface-crosslinking. Preferably it is added after surface-cross linking. Any mixture of the above listed polyols may be used.

When the water-absorbent polymer particles are coated with a polyol, the use amount of polyol, based on the water-absorbent polymer particles, is preferably from 0.005 to 2% by weight, more preferably from 0.01 to 1% by weight, most preferably from 0.05 to 0.5% by weight.

The coating is preferably performed in mixers with moving mixing tools, such as screw mixers, disk mixers, paddle mixers and drum coater. Suitable mixers are, for example, horizontal Pflugschar® plowshare mixers (Gebr. Lödige Maschinenbau GmbH; Paderborn; Germany), Vrieco-Nauta Continuous Mixers (Hosokawa Micron BV; Doetinchem; the Netherlands), Processall Mixmill Mixers (Processall Incorporated; Cincinnati; US) and Ruberg continuous flow mixers (Gebrüder Ruberg GmbH & Co KG, Nieheim, Germany). Moreover, it is also possible to use a fluidized bed for mixing.

Agglomeration

The water-absorbent polymer particles can further selectively be agglomerated. The agglomeration can take place after the polymerization, the thermal postreatment, the thermal surface-postcrosslinking or the coating.

Useful agglomeration assistants include water and water-miscible organic solvents, such as alcohols, tetrahydrofuran and acetone; water-soluble polymers can be used in addition.

For agglomeration a solution comprising the agglomeration assistant is sprayed onto the water-absorbing polymeric particles. The spraying with the solution can, for example, be carried out in mixers having moving mixing implements, such as screw mixers, paddle mixers, disk mixers, plowshare mixers and shovel mixers. Useful mixers include for example Lödige® mixers, Bepex® mixers, Nauta® mixers, Processall® mixers and Schugi® mixers. Vertical mixers are preferred. Fluidized bed apparatuses are particularly preferred.

Combination of Thermal Posttreatment, Surface-Postcrosslinking and Optionally Coating In a preferred embodiment of the present invention the steps of thermal posttreatment and thermal surface-postcrosslinking are combined in one process step. Such combination allows the use of low cost equipment and moreover the process can be run at low temperatures, that is cost-efficient and avoids discoloration and loss of performance properties of the finished product by thermal degradation.

The mixer may be selected from any of the equipment options cited in the thermal posttreatment section. Ruberg continuous flow mixers, Becker shovel mixers and Pflugschar® plowshare mixers are preferred.

In this particular preferred embodiment the surface-postcrosslinking solution is sprayed onto the water-absorbent polymer particles under agitation.

Following the thermal posttreatment/surface-postcrosslinking the water-absorbent polymer particles are dried to the desired moisture level and for this step any dryer cited in the surface-postcrosslinking section may be selected. However, as only drying needs to be accomplished in this particular preferred embodiment it is possible to use simple and low cost heated contact dryers like a heated screw dryer, for example a Holo-Flite® dryer (Metso Minerals Industries Inc.; Danville; U.S.A.). Alternatively a fluidized bed may be used. In cases where the product needs to be dried with a predetermined and narrow residence time it is possible to use torus disc dryers or paddle dryers, for example a Nara paddle dryer (NARA Machinery Europe; Frechen; Germany).

In a preferred embodiment of the present invention, polyvalent cations cited in the surface-postcrosslinking section are applied to the particle surface before, during or after addition of the surface-postcrosslinker by using different addition points along the axis of a horizontal mixer.

In a very particular preferred embodiment of the present invention the steps of thermal posttreatment, surface-postcrosslinking, and coating are combined in one process step. Suitable coatings are cationic polymers, surfactants, and inorganic inert substances that are cited in the coating section. The coating agent can be applied to the particle surface before, during or after addition of the surface-postcrosslinker also by using different addition points along the axis of a horizontal mixer.

The polyvalent cations and/or the cationic polymers can act as additional scavengers for residual surface-postcrosslinkers. In a preferred embodiment of the present invention the surface-postcrosslinkers are added prior to the polyvalent cations and/or the cationic polymers to allow the surface-postcrosslinker to react first.

The surfactants and/or the inorganic inert substances can be used to avoid sticking or caking during this process step under humid atmospheric conditions. Preferred surfactants are non-ionic and amphoteric surfactants. Preferred inorganic inert substances are precipitated silicas and fumed silicas in form of powder or dispersion.

The amount of total liquid used for preparing the solutions/dispersions is typically from 0.01% to 25% by weight, preferably from 0.5% to 12% by weight, more preferably from 2% to 7% by weight, most preferably from 3% to 6% by weight, in respect to the weight amount of water-absorbent polymer particles to be processed.

Preferred embodiments are depicted in FIGS. 1 to 12.

FIG. 1: Process scheme (without external fluidized bed)
FIG. 2: Process scheme (with external fluidized bed)
FIG. 3: Arrangement of the T_outlet measurement
FIG. 4: Arrangement of the dropletizer units
FIG. 5: Dropletizer unit (longitudinal cut)
FIG. 6: Dropletizer unit (cross sectional view)
FIG. 7: Bottom of the internal fluidized bed (top view)
FIG. 8: openings in the bottom of the internal fluidized bed
FIG. 9: Rake stirrer for the intern fluidized bed (top view)
FIG. 10: Rake stirrer for the intern fluidized bed (cross sectional view)
FIG. 11: Process scheme (surface-postcrosslinking)
FIG. 12: Process scheme (surface-postcrosslinking and coating)
FIG. 13: Contact dryer for surface-postcrosslnking The reference numerals have the following meanings:
1 Drying gas inlet pipe
2 Drying gas amount measurement
3 Gas distributor
4 Dropletizer units
5 Cocurrent spray dryer, cylindrical part
6 Cone
7 T_outlet measurement
8 Tower offgas pipe
9 Baghouse filter
10 Ventilator
11 Quench nozzles
12 Condenser column, counter current cooling
13 Heat exchanger
14 Pump
15 Pump
16 Water outlet
17 Ventilator
18 Offgas outlet
19 Nitrogen inlet
20 Heat exchanger
21 Ventilator
22 Heat exchanger
23 Steam injection via nozzles
24 Water loading measurement
25 Conditioned internal fluidized bed gas
26 Internal fluidized bed product temperature measurement
27 Internal fluidized bed
28 Rotary valve
29 Sieve
30 End product
31 Static mixer
32 Static mixer
33 Initiator feed
34 Initiator feed
35 Monomer feed
36 Fine particle fraction outlet to rework
37 External fluidized bed
38 Ventilator
39 External fluidized bed offgas outlet to baghouse filter
40 Rotary valve
41 Filtered air inlet
42 Ventilator 43 Heat exchanger
44 Steam injection via nozzle
45 Water loading measurement
46 Conditioned external fluidized bed gas
47 T_-outlet measurement (average temperature out of 3 measurements around tower circumference)
48 Dropletizer unit
49 Monomer premixed with initiator feed
50 Spray dryer tower wall
51 Dropletizer unit outer pipe
52 Dropletizer unit inner pipe
53 Dropletizer cassette
54 Teflon block
55 Valve
56 Monomer premixed with initiator feed inlet pipe connector
57 Droplet plate
58 Counter plate
59 Flow channels for temperature control water
60 Dead volume free flow channel for monomer solution
61 Dropletizer cassette stainless steel block
62 Bottom of the internal fluidized bed with four segments
63 Split openings of the segments
64 Rake stirrer
65 Prongs of the rake stirrer
66 Mixer
67 Optional coating feed
68 Postcrosslinker feed
69 Thermal dryer (surface-postcrosslinking)
70 Cooler
71 Optional coating/water feed
72 Coater
73 Coating/water feed
74 Base polymer feed
75 Discharge zone
76 Weir opening
77 weir plate
78 Weir height 100%
79 Weir height 50%
80 Shaft
81 Discharge cone
82 Inclination angle α
83 Temperature sensors ($T_1$ to $T_6$)
84 Paddle (shaft offset 90°)

The drying gas is fed via a gas distributor (3) at the top of the spray dryer as shown in FIG. 1. The drying gas is partly recycled (drying gas loop) via a baghouse filter (9) and a condenser column (12). The pressure inside the spray dryer is below ambient pressure.

Figure 3:
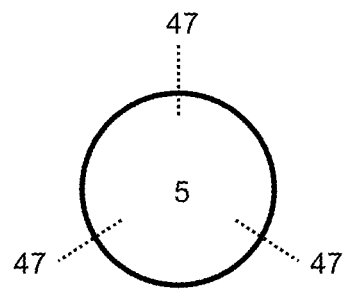
FIG. 3 illustrates an arrangement of the T_outlet measurement.

The spray dryer outlet temperature is preferably measured at three points around the circumference at the end of the cylindrical part as shown in FIG. 3. The single measurements (47) are used to calculate the average cylindrical spray dryer outlet temperature.

The product accumulated in the internal fluidized bed (27). Conditioned internal fluidized bed gas is fed to the internal fluidized bed (27) via line (25). The relative humidity of the internal fluidized bed gas is preferably controlled by adding steam via line (23).

The spray dryer offgas is filtered in baghouse filter (9) and sent to a condenser column (12) for quenching/cooling. After the baghouse filter (9) a recuperation heat exchanger system for preheating the gas after the condenser column (12) can be used. The baghouse filter (9) may be trace-heated on a temperature of preferably from 80 to 180° C., more preferably from 90 to 150° C., most preferably from 100 to 140° C. Excess water is pumped out of the condenser column (12) by controlling the (constant) filling level inside the condenser column (12). The water inside the condenser column (12) is cooled by a heat exchanger (13) and pumped counter-current to the gas via quench nozzles (11) so that the temperature inside the condenser column (12) is preferably from 20 to 100° C., more preferably from 25 to 80° C., most preferably from 30 to 60° C. The water inside the condenser column (12) is set to an alkaline pH by dosing a neutralizing agent to wash out vapors of monomer a). Aqueous solution from the condenser column (12) can be sent back for preparation of the monomer solution.

The condenser column offgas is split to the drying gas inlet pipe (1) and the conditioned internal fluidized bed gas (25). The gas temperatures are controlled via heat exchangers (20) and (22). The hot drying gas is fed to the cocurrent spray dryer via gas distributor (3). The gas distributor (3) consists preferably of a set of plates providing a pressure drop of preferably 1 to 100 mbar, more preferably 2 to 30 mbar, most preferably 4 to 20 mbar, depending on the drying gas amount. Turbulences and/or a centrifugal velocity can also be introduced into the drying gas if desired by using gas nozzles or baffle plates.

Conditioned internal fluidized bed gas is fed to the internal fluidized bed (27) via line (25). The relative humidity of the external fluidized bed gas is preferably controlled by adding steam via line (23). To prevent any condensation the steam is added together with the internal fluidized bed into the heat exchanger (22). The product holdup in the internal fluidized bed (27) can be controlled via rotational speed of the rotary valve (28).

The product is discharged from the internal fluidized bed (27) via rotary valve (28). The product holdup in the internal fluidized bed (27) can be controlled via rotational speed of the rotary valve (28). The sieve (29) is used for sieving off overs/lumps.

The monomer solution is preferably prepared by mixing first monomer a) with a neutralization agent and optionally secondly with crosslinker b). The temperature during neutralization is controlled to preferably from 5 to 60° C., more preferably from 8 to 40° C., most preferably from 10 to 30° C., by using a heat exchanger and pumping in a loop. A filter unit is preferably used in the loop after the pump. The initiators are metered into the monomer solution upstream of the dropletizer by means of static mixers (31) and (32) via lines (33) and (34) as shown in FIG. 1. Preferably a peroxide solution having a temperature of preferably from 5 to 60° C., more preferably from 10 to 50° C., most preferably from 15 to 40° C., is added via line (33) and preferably an azo initiator solution having a temperature of preferably from 2 to 30° C., more preferably from 3 to 15° C., most preferably from 4 to 8° C., is added via line (34). Each initiator is preferably pumped in a loop and dosed via control valves to each dropletizer unit. A second filter unit is preferably used after the static mixer (32). The mean residence time of the monomer solution admixed with the full initiator package in the piping before the droplet plates (57) is preferably less than 60 s, more preferably less than 30 s, most preferably less than 10 s.

Figure 4:
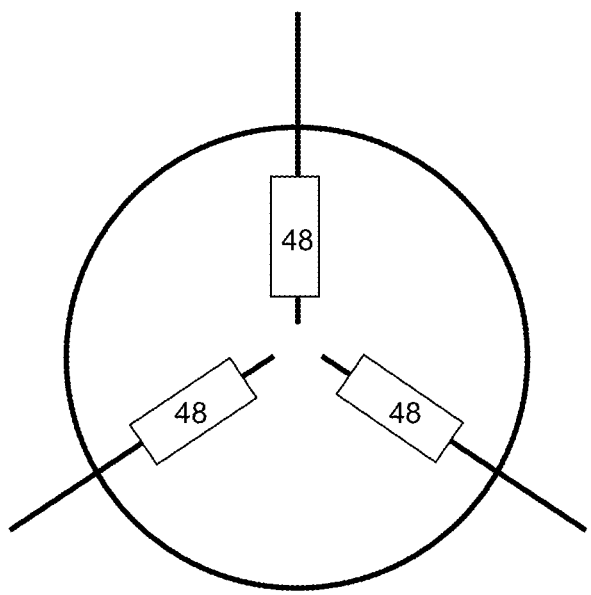
FIG. 4 illustrates an arrangement of a dropletizer unit.

For dosing the monomer solution into the top of the spray dryer preferably three dropletizer units are used as shown in FIG. 4. However, any number of dropletizers can be used that is required to optimize the throughput of the process and the quality of the product. Hence, in the present invention at least one dropletizer is employed, and as many dropletizers as geometrically allowed may be used.

Figure 5:
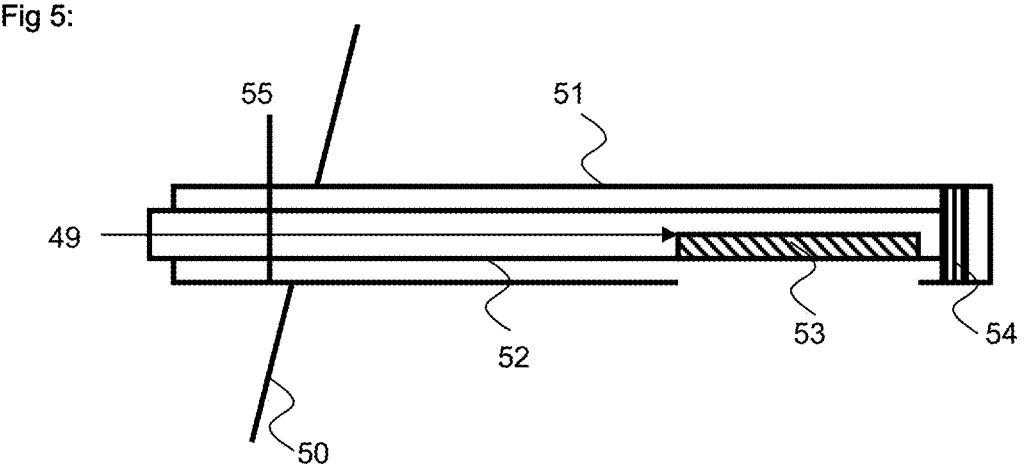
FIG. 5 is a longitudinal cut of a dropletizer unit.

A dropletizer unit consists of an outer pipe (51) having an opening for the dropletizer cassette (53) as shown in FIG. 5. The dropletizer cassette (53) is connected with an inner pipe (52). The inner pipe (53) having a PTFE block (54) at the end as sealing can be pushed in and out of the outer pipe (51) during operation of the process for maintenance purposes.

Figure 6:
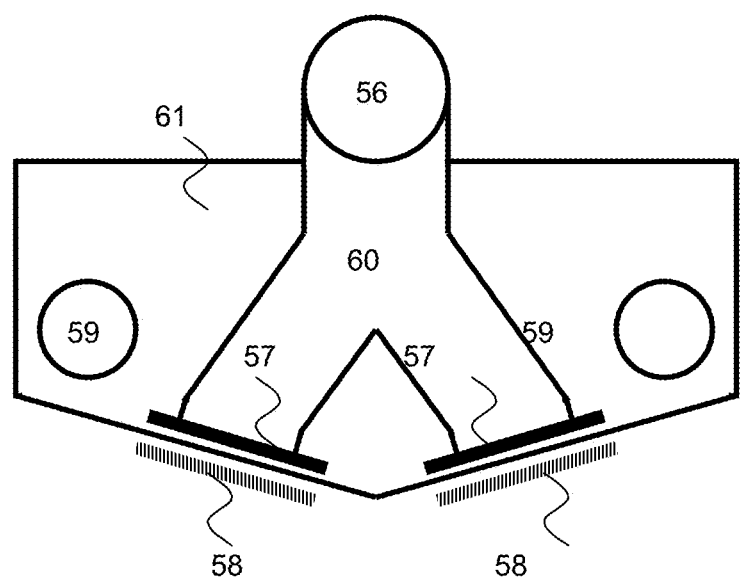
FIG. 6 is a cross-sectional view of a dropletizer unit.

The temperature of the dropletizer cassette (61) is controlled to preferably 5 to 80° C., more preferably 10 to 70° C., most preferably 30 to 60° C., by water in flow channels (59) as shown in FIG. 6.

The dropletizer cassette has preferably from 10 to 1500, more preferably from 50 to 1000, most preferably from 100 to 500, bores having a diameter of preferably from 50 to 500 µm, more preferably from 100 to 300 µm, most preferably from 150 to 250 µm. The bores can be of circular, rectangular, triangular or any other shape. Circular bores are preferred. The ratio of bore length to bore diameter is preferably from 0.5 to 10, more preferably from 0.8 to 5, most preferably from 1 to 3. The droplet plate (57) can have a greater thickness than the bore length when using an inlet bore channel. The droplet plate (57) is preferably long and narrow as disclosed in WO 2008/086976 A1. Multiple rows of bores per droplet plate can be used, preferably from 1 to 20 rows, more preferably from 2 to 5 rows.

The dropletizer cassette (61) consists of a flow channel (60) having essential no stagnant volume for homogeneous distribution of the premixed monomer and initiator solutions and two droplet plates (57). The droplet plates (57) have an angled configuration with an angle of preferably from 1 to 90°, more preferably from 3 to 45°, most preferably from 5 to 20°. Each droplet plate (57) is preferably made of a heat and/or chemically resistant material, such as stainless steel, polyether ether ketone, polycarbonate, polyarylsulfone, such as polysulfone, or polyphenylsulfone, or fluorous polymers, such as perfluoroalkoxyethylene, polytetrafluoroethylene, polyvinylidenfluorid, ethylene-chlorotrifluoroethylene copolymers, ethylene-tetrafluoroethylene copolymers and fluorinated polyethylene. Coated droplet plates as disclosed in WO 2007/031441 A1 can also be used. The choice of material for the droplet plate is not limited except that droplet formation must work and it is preferable to use materials which do not catalyze the start of polymerization on its surface.

The throughput of monomer including initiator solutions per dropletizer unit is preferably from 150 to 2500 kg/h, more preferably from 200 to 1000 kg/h, most preferably from 300 to 600 kg/h. The throughput per bore is preferably from 0.1 to 10 kg/h, more preferably from 0.5 to 5 kg/h, most preferably from 0.7 to 2 kg/h.

The start-up of the cocurrent spray dryer (5) can be done in the following sequence:
starting the condenser column (12),
starting the ventilators (10) and (17),
starting the heat exchanger (20),
heating up the drying gas loop up to 95° C.,
starting the nitrogen feed via the nitrogen inlet (19),
waiting until the residual oxygen is below 4% by weight,
heating up the drying gas loop,
at a temperature of 105° C. starting the water feed (not shown) and
at target temperature stopping the water feed and starting the monomer feed via dropletizer unit (4)

The shut-down of the cocurrent spray dryer (5) can be done in the following sequence:
stopping the monomer feed and starting the water feed (not shown),
shut-down of the heat exchanger (20),
cooling the drying gas loop via heat exchanger (13),
at a temperature of 105° C. stopping the water feed,
at a temperature of 60° C. stopping the nitrogen feed via the nitrogen inlet (19) and
feeding air into the drying gas loop (not shown)

To prevent damages the cocurrent spray dryer (5) must be heated up and cooled down very carefully. Any quick temperature change must be avoided.

Figure 7:
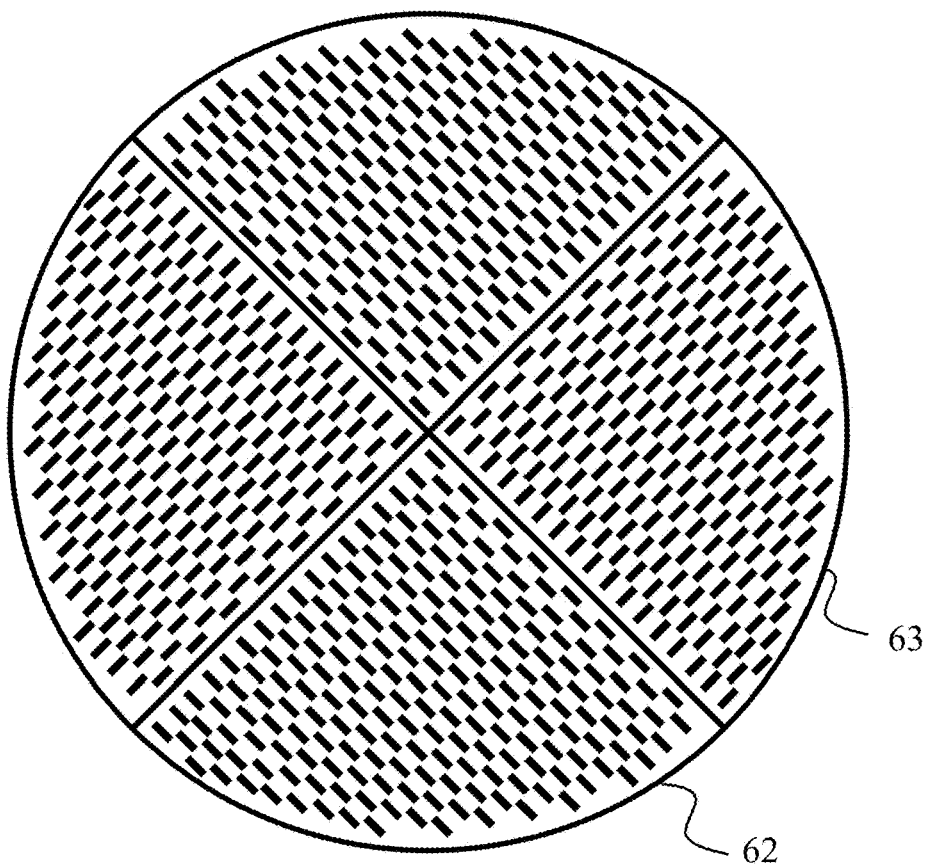
FIG. 7 is a top view of the bottom of the internal fluidized bed.
Figure 8:
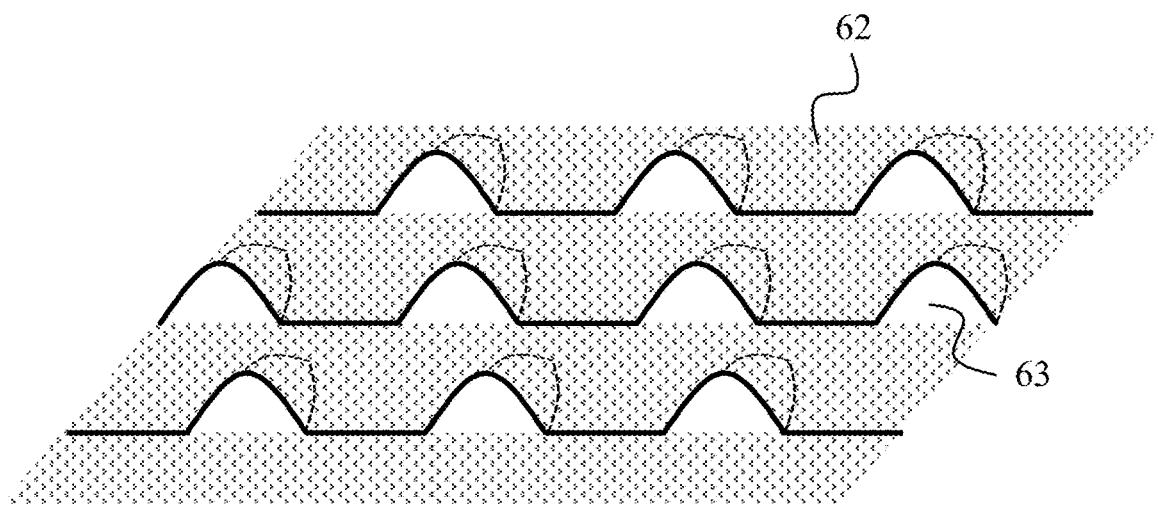
FIG. 8 illustrates the openings in the bottom of the internal fluidized bed.

The openings in the bottom of the internal fluidized bed may be arranged in a way that the water-absorbent polymer particles flow in a cycle as shown in FIG. 7. The bottom shown in FIG. 7 comprises of four segments (62). The openings (63) in the segments (62) are in the shape of slits that guides the passing gas stream into the direction of the next segment (62). FIG. 8 shows an enlarged view of the openings (63).

The opening may have the shape of holes or slits. The diameter of the holes is preferred from 0.1 to 10 mm, more preferred from 0.2 to 5 mm, most preferred from 0.5 to 2 mm. The slits have a length of preferred from 1 to 100 mm, more preferred from 2 to 20 mm, most preferred from 5 to 10 mm, and a width of preferred from 0.5 to 20 mm, more preferred from 1 to 10 mm, most preferred from 2 to 5 mm.

Figure 9:
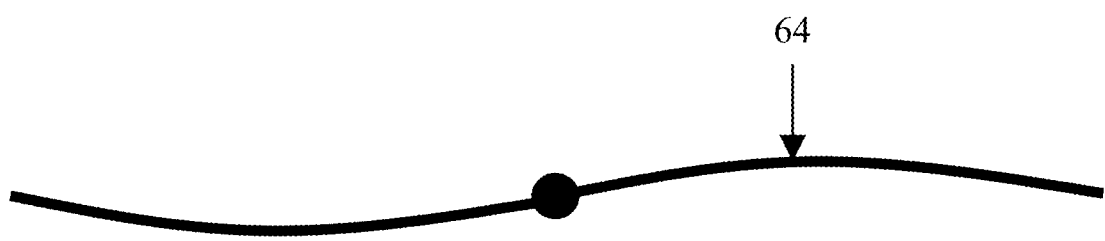
FIG. 9 is the top view of a rake stirrer for the internal fluidized bed.
Figure 10:
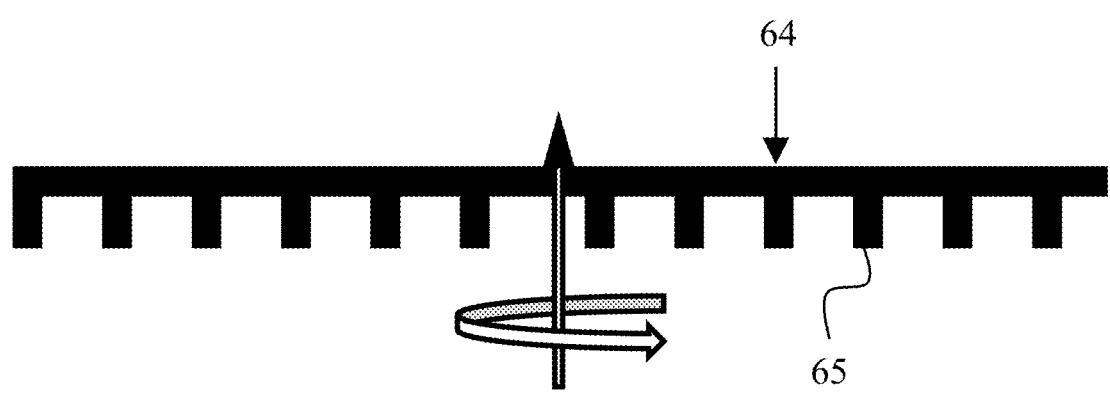
FIG. 10 is the cross-sectional view of a rake stirrer for the internal fluidized bed.
Figure 11:
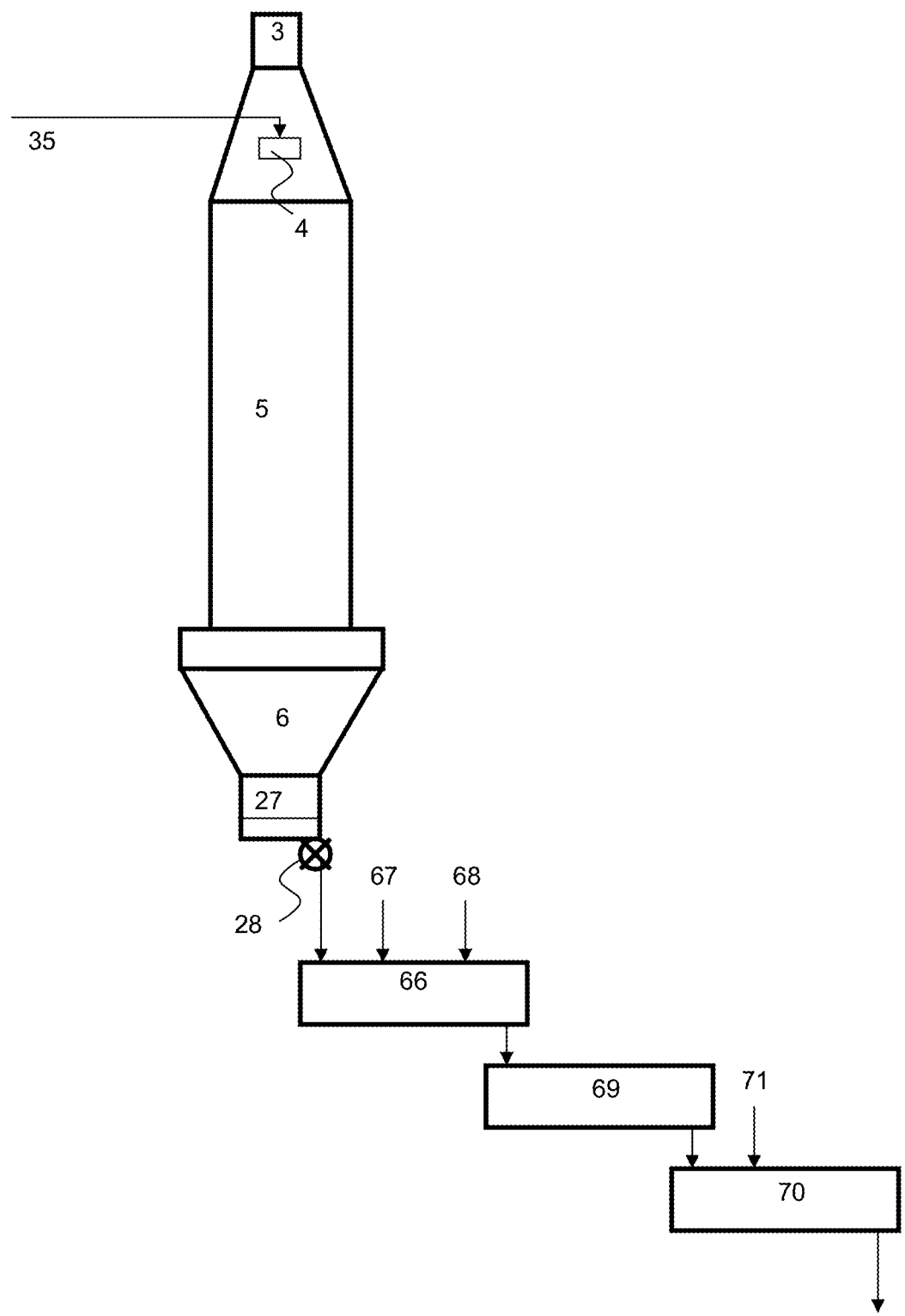
FIG. 11 illustrates a process scheme for surface-postcrosslinking.
Figure 12:
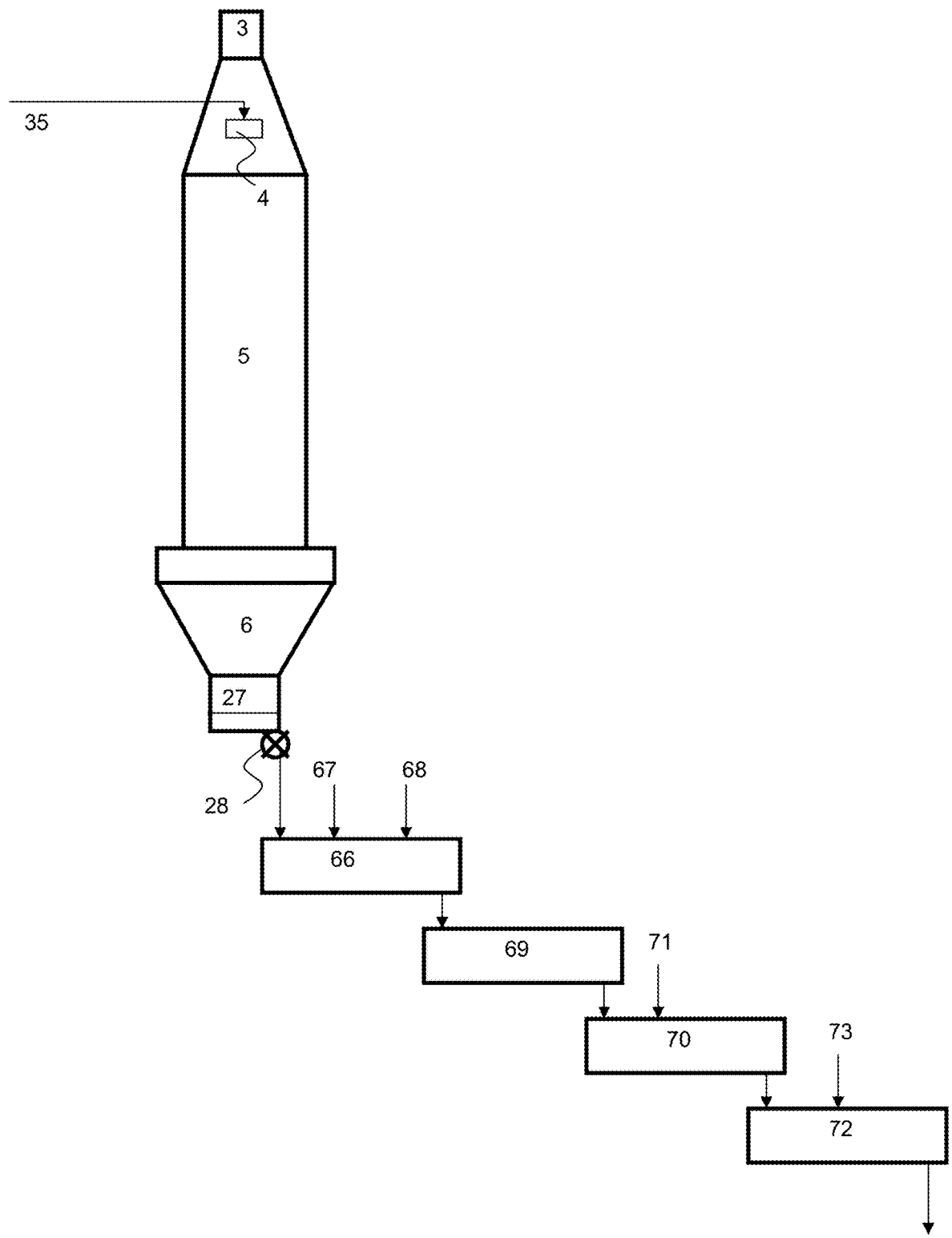
FIG. 12 illustrates a process scheme for surface-postcrosslinking and coating.

FIG. 9 and FIG. 10 show a rake stirrer (64) that may be used in the internal fluidized bed. The prongs (65) of the rake have a staggered arrangement. The speed of rake stirrer is preferably from 0.5 to 20 rpm, more preferably from 1 to 10 rpm most preferably from 2 to 5 rpm.

For start-up the internal fluidized bed may be filled with a layer of water-absorbent polymer particles, preferably 5 to 50 cm, more preferably from 10 to 40 cm, most preferably from 15 to 30 cm.

Water-Absorbent Polymer Particles

The present invention provides water-absorbent polymer particles obtainable by the process according to the invention.

The present invention further provides surface-postcrosslinked water-absorbent polymer particles having a centrifuge retention capacity from 35 to 75 g/g, an absorption under high load from 20 to 50 g/g, a level of extractable constituents of less than 10% by weight, and a porosity from 20 to 40%.

It is particular advantageous that the surface-postcrosslinked water-absorbent polymer particles obtainable by the process according to the invention exhibit a very high centrifuge retention capacity (CRC) and a high absorption under high load (AUHL), and that the sum of these parameters (=CRC+AUHL) is at least 60 g/g, preferably at least 65 g/g, most preferably at least 70 g/g, and not more than 120 g/g, preferably less than 100 g/g, more preferably less than 90 g/g, and most preferably less than 80 g/g. The surface-postcrosslinked water-absorbent polymer particles obtainable by the process according to the invention further preferably exhibit an absorption under high load (AUHL) of at least 15 g/g, preferably at least 18 g/g, more preferably at least 21 g/g, most preferably at least 25 g/g, and not more than 50 g/g.

As the centrifuge retention capacity (CRC) is the maximum water retention capacity of the surface-postcrosslinked water-absorbent polymer particles it is of interest to maximize this parameter. However the absorption under high load (AUHL) is important to allow the fiber-matrix in a hygiene article to open up pores during swelling to allow further liquid to pass easily through the article structure to enable rapid uptake of this liquid. Hence there is a need to maximize both parameters.

The inventive water-absorbent polymer particles have a centrifuge retention capacity (CRC) from 35 to 75 g/g, preferably from 37 to 65 g/g, more preferably from 39 to 60 g/g, most preferably from 40 to 55 g/g.

The inventive water-absorbent polymer particles have an absorbency under a load of 49.2 g/cm$^2$ (AUHL) from 20 to 50 g/g, preferably from 22 to 45 g/g, more preferably from 24 to 40 g/g, most preferably from 25 to 35 g/g.

The inventive water-absorbent polymer particles have a level of extractable constituents of less than 10% by weight, preferably less than 8% by weight, more preferably less than 6% by weight, most preferably less than 5% by weight.

The inventive water-absorbent polymer particles have a porosity from 20 to 40%, preferably from 22 to 38%, more preferably from 24 to 36%, most preferably from 25 to 35%.

Preferred water-absorbent polymer particles are polymer particles having a centrifuge retention capacity (CRC) from 37 to 65 g/g, an absorption under high load (AUHL) from 22 to 45 g/g, a level of extractable constituents of less than 8% by weight and a porosity from 22 to 45%.

More preferred water-absorbent polymer particles are polymer particles having a centrifuge retention capacity (CRC) from 39 to 60 g/g, an absorption under high load (AUHL) from 24 to 40 g/g, a level of extractable constituents of less than 6% by weight and a porosity from 24 to 40%.

Most preferred water-absorbent polymer particles are polymer particles having a centrifuge retention capacity (CRC) from 40 to 55 g/g, an absorption under high load (AUHL) from 25 to 35 g/g, a level of extractable constituents of less than 5% by weight and a porosity from 25 to 35%.

The present invention further provides surface-postcrosslinked water-absorbent polymer particles having a total liquid uptake of $$Y > -500 \times \ln(X) + 1880,$$

preferably $Y > -495 \times \ln(X) + 1875,$ more preferably $Y > -490 \times \ln(X) + 1870,$ most preferably $Y > -485 \times \ln(X) + 1865,$ wherein Y [g] is the total liquid uptake and X [g/g] is the centrifuge retention capacity (CRC), wherein the centrifuge retention capacity (CRC) is at least 25 g/g, preferably at least 30 g/g, more preferably at least 35 g/g, most preferably at least 40 g/g, and the liquid uptake is at least 30 g, preferably at least 35 g/g, more preferably at least 40 g/g, most preferably at least 45 g/g.

The present invention further provides surface-postcrosslinked water-absorbent polymer particles having a change of characteristic swelling time of less than 0.6, preferably less than 0.5, more preferably less than 0.45, most preferably less than 0.4, and a centrifuge retention capacity (CRC) of at least 35 g/g, preferably at least 37 g/g, more preferably at least 38.5 g/g, most preferably at least 40 g/g, wherein the change of characteristic swelling time is $$Z < (\tau_{0.5} - \tau_{0.1})/\tau_{0.5}$$

wherein Z is the change of characteristic swelling time, $\tau_{0.1}$ is the characteristic swelling time under a pressure of 0.1 psi (6.9 g/cm$^2$) and $\tau_{0.5}$ is the characteristic swelling time under a pressure of 0.5 psi (35.0 g/cm$^2$).

The inventive water-absorbent polymer particles have a mean sphericity from 0.80 to 0.95, preferably from 0.82 to 0.93, more preferably from 0.84 to 0.91, most preferably from 0.85 to 0.90. The sphericity (SPHT) is defined as $$SPHT = \frac{4\pi A}{U^2},$$

where A is the cross-sectional area and U is the cross-sectional circumference of the polymer particles. The mean sphericity is the volume-average sphericity.

The mean sphericity can be determined, for example, with the Camsizer® image analysis system (Retsch Technology GmbH; Haan; Germany):

For the measurement, the product is introduced through a funnel and conveyed to the falling shaft with a metering channel. While the particles fall past a light wall, they are recorded selectively by a camera. The images recorded are evaluated by the software in accordance with the parameters selected.

To characterize the roundness, the parameters designated as sphericity in the program are employed. The parameters reported are the mean volume-weighted sphericities, the volume of the particles being determined via the equivalent diameter xc$_{min}$. To determine the equivalent diameter xc$_{min}$, the longest chord diameter for a total of 32 different spatial directions is measured in each case. The equivalent diameter xc$_{min}$ is the shortest of these 32 chord diameters. To record the particles, the so-called CCD-zoom camera (CAM-Z) is used. To control the metering channel, a surface coverage fraction in the detection window of the camera (transmission) of 0.5% is predefined.

Water-absorbent polymer particles with relatively low sphericity are obtained by reverse suspension polymerization when the polymer beads are agglomerated during or after the polymerization.

The water-absorbent polymer particles prepared by customary solution polymerization (gel polymerization) are ground and classified after drying to obtain irregular polymer particles. The mean sphericity of these polymer particles is between approx. 0.72 and approx. 0.78.

The inventive water-absorbent polymer particles have a content of hydrophobic solvent of preferably less than 0.005% by weight, more preferably less than 0.002% by weight and most preferably less than 0.001% by weight. The content of hydrophobic solvent can be determined by gas chromatography, for example by means of the headspace technique. A hydrophobic solvent within the scope of the present invention is either immiscible in water or only sparingly miscible. Typical examples of hydrophobic solvents are pentane, hexane, cyclohexane, toluene.

Water-absorbent polymer particles which have been obtained by reverse suspension polymerization still comprise typically approx. 0.01% by weight of the hydrophobic solvent used as the reaction medium.

The inventive water-absorbent polymer particles have a dispersant content of typically less than 1% by weight, preferably less than 0.5% by weight, more preferably less than 0.1% by weight and most preferably less than 0.05% by weight.

Water-absorbent polymer particles which have been obtained by reverse suspension polymerization still comprise typically at least 1% by weight of the dispersant, i.e. ethylcellulose, used to stabilize the suspension.

The inventive water-absorbent polymer particles have a bulk density preferably from 0.6 to 1 g/cm$^3$, more preferably from 0.65 to 0.9 g/cm$^3$, most preferably from 0.68 to 0.8 g/cm$^3$.

The average particle diameter (APD) of the inventive water-absorbent particles is preferably from 200 to 550 µm, more preferably from 250 to 500 µm, most preferably from 350 to 450 µm.

The particle diameter distribution (PDD) of the inventive water-absorbent particles is preferably less than 0.7, more preferably less than 0.65, more preferably less than 0.6.

The inventive water-absorbent polymer particles can be mixed with other water-absorbent polymer particles prepared by other processes, i.e. solution polymerization.

Fluid-Absorbent Articles

The present invention further provides fluid-absorbent articles. The fluid-absorbent articles comprise of
(A) an upper liquid-pervious layer
(B) a lower liquid-impervious layer
(C) a fluid-absorbent core between (A) and (B) comprising
  from 5 to 90% by weight fibrous material and from 10 to 95% by weight water-absorbent polymer particles of the present invention;
  preferably from 20 to 80% by weight fibrous material and from 20 to 80% by weight water-absorbent polymer particles of the present invention;
  more preferably from 30 to 75% by weight fibrous material and from 25 to 70% by weight water-absorbent polymer particles of the present invention;
  most preferably from 40 to 70% by weight fibrous material and from 30 to 60% by weight water-absorbent polymer particles of the present invention;
(D) an optional acquisition-distribution layer between (A) and (C), comprising
  from 80 to 100% by weight fibrous material and from 0 to 20% by weight water-absorbent polymer particles of the present invention;
  preferably from 85 to 99.9% by weight fibrous material and from 0.01 to 15% by weight water-absorbent polymer particles of the present invention;
  more preferably from 90 to 99.5% by weight fibrous material and from 0.5 to 10% by weight water-absorbent polymer particles of the present invention;
  most preferably from 95 to 99% by weight fibrous material and from 1 to 5% by weight water-absorbent polymer particles of the present invention;
(E) an optional tissue layer disposed immediately above and/or below (C); and
(F) other optional components.

Fluid-absorbent articles are understood to mean, for example, incontinence pads and incontinence briefs for adults or diapers for babies. Suitable fluid-absorbent articles including fluid-absorbent compositions comprising fibrous materials and optionally water-absorbent polymer particles to form fibrous webs or matrices for the substrates, layers, sheets and/or the fluid-absorbent core.

The acquisition-distribution layer acts as transport and distribution layer of the discharged body fluids and is typically optimized to affect efficient liquid distribution with the underlying fluid-absorbent core. Hence, for quick temporary liquid retention it provides the necessary void space while its area coverage of the underlying fluid-absorbent core must affect the necessary liquid distribution and is adopted to the ability of the fluid-absorbent core to quickly dewater the acquisition-distribution layer.

For fluid-absorbent articles that possess a very good dewatering that has excellent wicking capability it is advantageous to use acquisition-distribution layers. For fluid-absorbent articles that possess a fluid-absorbent core comprising very permeable water-absorbent polymer particles a small and thin acquisition-distribution layer can be used.

Suitable fluid-absorbent articles are composed of several layers whose individual elements must show preferably definite functional parameter such as dryness for the upper liquid-pervious layer, vapor permeability without wetting through for the lower liquid-impervious layer, a flexible, vapor permeable and thin fluid-absorbent core, showing fast absorption rates and being able to retain highest quantities of body fluids, and an acquisition-distribution layer between the upper layer and the core. These individual elements are combined such that the resultant fluid-absorbent article meets overall criteria such as flexibility, water vapor breathability, dryness, wearing comfort and protection on the one side, and concerning liquid retention, rewet and prevention of wet through on the other side. The specific combination of these layers provides a fluid-absorbent article delivering both high protection levels as well as high comfort to the consumer.

The products as obtained by the present invention are also very suitable to be incorporated into low-fluff, low-fiber, fluff-less, or fiber-less hygiene article designs. Such designs and methods to make them are for example described in the following publications and literature cited therein and are expressly incorporated into the present invention: EP 2 301 499 A1, EP 2 314 264 A1, EP 2 387 981 A1, EP 2 486 901 A1, EP 2 524 679 A1, EP 2 524 679 A1, EP 2 524 680 A1, EP 2 565 031 A1, U.S. Pat. No. 6,972,011, US 2011/0162989, US 2011/0270204, WO 2010/004894 A1, WO 2010/004895 A1, WO 2010/076857 A1, WO 2010/082373 A1, WO 2010/118409 A1, WO 2010/133529 A2, WO 2010/143635 A1, WO 2011/084981 A1, WO 2011/086841 A1, WO 2011/086842 A1, WO 2011/086843 A1, WO 2011/086844 A1, WO 2011/117997 A1, WO 2011/136087 A1, WO 2012/048879 A1, WO 2012/052173 A1 und WO 2012/052172 A1.

The present invention further provides fluid-absorbent articles, comprising water-absorbent polymer particles of the present invention and less than 15% by weight fibrous material and/or adhesives in the absorbent core.

The water-absorbent polymer particles and the fluid-absorbent articles are tested by means of the test methods described below.

Methods:

The measurements should, unless stated otherwise, be carried out at an ambient temperature of 23±2° C. and a relative atmospheric humidity of 50±10%. The water-absorbent polymers are mixed thoroughly before the measurement.

Vortex 50.0±1.0 ml of 0.9% NaCl solution are added into a 100 ml beaker. A cylindrical stirrer bar (30×6 mm) is added and the saline solution is stirred on a stir plate at 60 rpm. 2.000±0.010 g of water-absorbent polymer particles are added to the beaker as quickly as possible, starting a stop watch as addition begins. The stopwatch is stopped when the surface of the mixture becomes 'still' that means the surface has no turbulence, and while the mixture may still turn, the entire surface of particles turns as a unit. The displayed time of the stopwatch is recorded as Vortex time.

Residual Monomers

The level of residual monomers in the water-absorbent polymer particles is determined by the EDANA recommended test method No. WSP 210.3-(11) "Residual Monomers".

Particle Size Distribution

The particle size distribution of the water-absorbent polymer particles is determined with the Camziser® image analysis system (Retsch Technology GmbH; Haan; Germany).

For determination of the average particle diameter and the particle diameter distribution the proportions of the particle fractions by volume are plotted in cumulated form and the average particle diameter is determined graphically.

The average particle diameter (APD) here is the value of the mesh size which gives rise to a cumulative 50% by weight.

The particle diameter distribution (PDD) is calculated as follows:

$$PDD = \frac{x_2 - x_1}{APD},$$

wherein $x_1$ is the value of the mesh size which gives rise to a cumulative 90% by weight and $x_2$ is the value of the mesh size which gives rise to a cumulative 10% by weight.

Mean Sphericity

The mean sphericity is determined with the Camziser® image analysis system (Retsch Technology GmbH; Haan; Germany) using the particle diameter fraction from 100 to 1,000 μm.

Moisture Content

The moisture content of the water-absorbent polymer particles is determined by the EDANA recommended test method No. WSP 230.3 (11) "Mass Loss Upon Heating".

Centrifuge Retention Capacity (CRC)

The centrifuge retention capacity of the water-absorbent polymer particles is determined by the EDANA recommended test method No. WSP 241.3 (11) "Free Swell Capacity in Saline, After Centrifugation", wherein for higher values of the centrifuge retention capacity larger tea bags have to be used.

Absorbency Under No Load (AUNL)

The absorbency under no load of the water-absorbent polymer particles is determined analogously to the EDANA recommended test method No. WSP 242.3 (11) "Gravimetric Determination of Absorption Under Pressure", except using a weight of 0.0 g/cm$^2$ instead of a weight of 21.0 g/cm$^2$.

Absorbency Under Load (AUL)

The absorbency under load of the water-absorbent polymer particles is determined by the EDANA recommended test method No. WSP 242.3 (11) "Gravimetric Determination of Absorption Under Pressure"

Absorbency Under High Load (AUHL)

The absorbency under high load of the water-absorbent polymer particles is determined analogously to the EDANA recommended test method No. WSP 242.3 (11) "Gravimetric Determination of Absorption Under Pressure", except using a weight of 49.2 g/cm$^2$ instead of a weight of 21.0 g/cm$^2$.

Porosity

The porosity of the water-absorbent polymer particles is calculated as follows:

$$Porosity = \frac{AUNL - CRC}{AUNL}$$

Bulk Density/Flow Rate

The bulk density (BD) and the flow rate (FR) of the water-absorbent polymer particles is determined by the EDANA recommended test method No. WSP 250.3 (11) "Gravimetric Determination of flow rate, Gravimetric Determination of Density".

Extractables

The level of extractable constituents in the water-absorbent polymer particles is determined by the EDANA recommended test method No. WSP 470.2-05 "Extractables".

Saline Flow Conductivity (SFC)

The saline flow conductivity is, as described in EP 0 640 330 A1, determined as the gel layer permeability of a swollen gel layer of fluid-absorbent polymer particles, although the apparatus described on page 19 and in FIG. 8 in the aforementioned patent application was modified to the effect that the glass frit (40) is no longer used, the plunger (39) consists of the same polymer material as the cylinder (37) and now comprises 21 bores having a diameter of 9.65 mm each distributed uniformly over the entire contact surface. The procedure and the evaluation of the measurement remains unchanged from EP 0 640 330 A1. The flow rate is recorded automatically.

The saline flow conductivity (SFC) is calculated as follows:

$$SFC[cm^3s/g] = (Fg(t=0) \times L0)/(d \times A \times WP),$$

where Fg(t=0) is the flow rate of NaCl solution in g/s, which is obtained by means of a linear regression analysis of the Fg(t) data of the flow determinations by extrapolation to t=0, L0 is the thickness of the gel layer in cm, d is the density of the NaCl solution in g/cm$^3$, A is the surface area of the gel layer in cm$^2$ and WP is the hydrostatic pressure over the gel layer in dyn/cm$^2$.

Free Swell Rate (FSR)

1.00 g (=W1) of the dry fluid-absorbent polymer particles is weighed into a 25 ml glass beaker and is uniformly distributed on the base of the glass beaker. 20 ml of a 0.9% by weight sodium chloride solution are then dispensed into a second glass beaker, the content of this beaker is rapidly added to the first beaker and a stopwatch is started. As soon as the last drop of salt solution is absorbed, confirmed by the disappearance of the reflection on the liquid surface, the stopwatch is stopped. The exact amount of liquid poured from the second beaker and absorbed by the polymer in the first beaker is accurately determined by weighing back the second beaker (=W2). The time needed for the absorption, which was measured with the stopwatch, is denoted t. The disappearance of the last drop of liquid on the surface is defined as time t.

The free swell rate (FSR) is calculated as follows:

$$FSR[g/gs] = W2/(W1 \times t)$$

When the moisture content of the hydrogel-forming polymer is more than 3% by weight, however, the weight W1 must be corrected for this moisture content.

Volumetric Absorbency Under Load (VAUL)

The volumetric absorbency under a load is used in order to measure the swelling kinetics, i.e. the characteristic swelling time, of water-absorbent polymer particles under different applied pressures. The height of swelling is recorded as a function of time.

Figure 14:
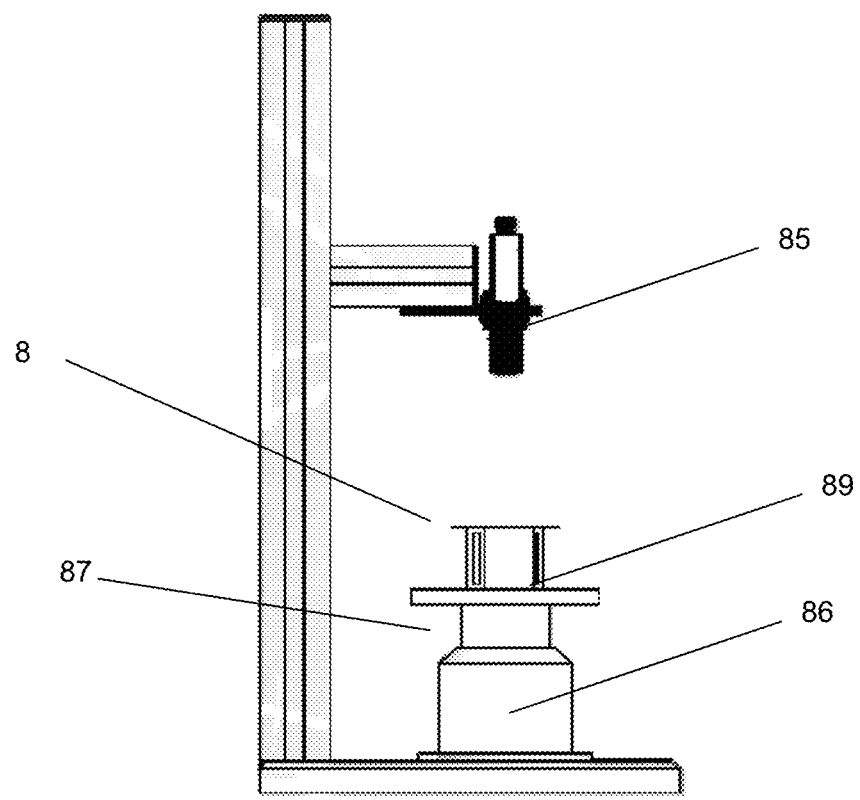
FIG. 14 illustrates the apparatus used to measure Volumetric Absorbency Under Load (VAUL)

The set up is show in FIG. 14 and consists of

An ultrasonic distance sensor (85) type BUS M18K0-XBFX-030-504K (Balluff GmbH, Neuhausen a.d.F.; Germany) is placed above the cell. The sensor receives ultrasound reflected by the metal plate. The sensor is connected to an electronic recorder.

A PTFE cell (86) having a diameter of 75 mm, a height of 73 mm and an internal diameter of 52 mm A cylinder (87) made of metal or plastic having a diameter of 50 mm, a height of 71 mm and a mesh bottom)

A metal reflector (88) having a diameter of 57 mm and a height of 45 mm

Metal ring weights (89) having a diameter of 100 mm and weights calibrated to 278.0 g or 554.0 g It is possible to adjust the pressure applied to the sample by changing the combination of cylinder (86) and metal ring (88) weight as summarized in the following tables:

| Available Equipment | Weight | psi |
| --- | --- | --- |
| Metal reflector | 13.0 g | 0.009 |
| Plastic cylinder | 28.0 g | 0.020 |
| Metal cylinder | 126.0 g | 0.091 |
| Small ring weight | 278.0 g | 0.201 |
| Large ring weight | 554.0 g | 0.401 |

| Possible Combinations | psi |
| --- | --- |
| Metal reflector + plastic cylinder | 0.03 |
| Metal reflector + metal cylinder | 0.10 |
| Metal reflector + metal cylinder + small ring weight | 0.30 |
| Metal reflector + metal cylinder + large ring weight | 0.50 |
| Metal reflector + metal cylinder + small ring weight + large ring weight | 0.70 |

A sample of 2.0 g of water-absorbent polymer particles is placed in the PTFE cell (86). The cylinder (equipped with mesh bottom) and the metal reflector (88) on top of it are placed into the PTFE cell (86). In order to apply higher pressure, metal rings weights (89) can be placed on the cylinder.

60.0 g of aqueous saline solution (0.9% by weight) are added into the PTFE cell (86) with a syringe and the recording is started. During the swelling, the water-absorbent polymer particles push the cylinder (87) up and the changes in the distance between the metal reflector (88) and the sensor (85) are recorded.

After 120 minutes, the experiment is stopped and the recorded data are transferred from the recorder to a PC using a USB stick. The characteristic swelling time is calculated according to the equation $Q(t)=Q_{max} \cdot (1-e^{-t/\tau})$ as described by "Modern Superabsorbent Polymer Technology" (page 155, equation 4.13) wherein Q(t) is the swelling of the superabsorbent which is monitored during the experiment, $Q_{max}$ corresponds to the maximum swelling reached after 120 minutes (end of the experiment) and τ is the characteristic swelling time (τ is the inverse rate constant k).

Using the add-in functionality 'Solver' of Microsoft Excel software, a theoretical curve can be fitted to the measured data and the characteristic time for 0.03 psi is calculated.

The measurements are repeated for different pressures (0.1 psi, 0.3 psi, 0.5 psi and 0.7 psi) using combinations of cylinder and ring weights. The characteristic swelling times for the different pressures can be calculated using the equation $Q(t)=Q_{max} \cdot (1-e^{-t/\tau})$.

Wicking Absorption

Figure 15:
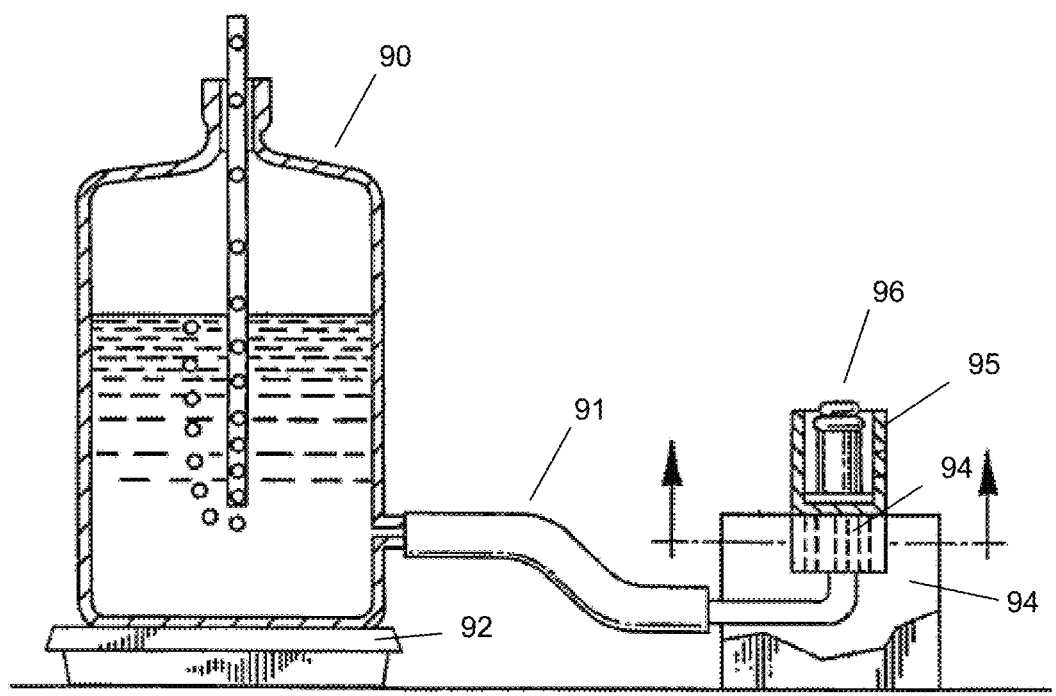
FIG. 15 illustrates the apparatus used to measure Wicking absorption.

The wicking absorption is used in order to measure the total liquid uptake of water-absorbent polymer particles under applied pressure. The set-up is show in FIG. 15.

A 500 ml glass bottle (90) (scale division 100 mL, height 26.5 cm) equipped with an exit tube of Duran® glass, is filled with 500 mL of aqueous saline solution (0.9% by weight). The bottle has an opening at the bottom end which can be connected to the Plexiglas plate through a flexible hose (91).

A balance (92) connected to a computer is placed on Plexiglas block (area 20×26 cm$^2$, height 6 cm). The glass bottle is then placed on the balance.

A Plexiglas plate (93) (area: 11×11 cm$^2$, height: 3.5 cm) is placed on a lifting platform. A porosity P1 glass frit of 7 cm in diameter and 0.45 cm high (94) has been liquid-tightly embedded in the Plexiglas plate, i.e. the fluid exits through the pores of the frit and not via the edge between Plexiglas plate and frit. A Plexiglas tube leads through the outer shell of Plexiglas plate into the center of the Plexiglas plate up to the frit to ensure fluid transportation. The fluid tube is then connected with the flexible hose (35 cm in length, 1.0 cm external diameter, 0.7 cm internal diameter) to the glass bottle (90).

The lifting platform is used to adjust the upper side of the frit to the level of the bottom end of the glass bottle, so that an always atmospheric flux of fluid from the bottle to the measuring apparatus is ensured during measurement. The upper side of the frit is adjusted such that its surface is moist but there is no supernatant film of water on the frit.

The fluid in the glass bottle (90) is made up to 500 ml before every run.

In a Plexiglas cylinder (95) (7 cm in external diameter, 6 cm in internal diameter, 16 cm in height) and equipped with a 400 mesh (36 μm) at the bottom are placed 26 g of water-absorbent polymer particles. The surface of the water-absorbent polymer particles is smoothed. The fill level is about 1.5 cm. Then a weight (96) of 0.3 psi (21.0 g/cm$^2$) is placed on top of the water-absorbent polymer particles.

The Plexiglas cylinder is placed on the (moist) frit and the electronic data recording started. A decrease in the weight of the balance is registered as a function of time. This then indicates how much aqueous saline solution has been absorbed by the swelling gel of water-absorbent polymer particles at a certain time. The data are automatically captured every 10 seconds. The measurement is carried out at 0.3 psi (21.0 g/cm$^2$) for a period of 120 minutes per sample. The total liquid uptake is the total amount of aqueous saline solution absorbed by each 26 g sample.

Rewet Under Load (RUL)

The test determines the amount of fluid a fluid-absorbent article will release after being maintained at a pressure of 0.7 psi (49.2 g/cm$^2$) for 10 min following multiple separate insults. The rewet under load is measured by the amount of fluid the fluid-absorbent article releases under pressure. The rewet under load is measured after each insult.

The fluid-absorbent article is clamped nonwoven side upward onto the inspection table. The insult point is marked accordingly with regard to the type and gender of the diaper to be tested (i.e. in the centre of the core for girl, 2.5 cm towards the front for unisex and 5 cm towards the front for boy). A 3.64 kg circular weight (10 cm diameter) having a central opening (2.3 cm diameter) with perspex tube is placed with on the previously marked insult point.

For the primary insult 100 g of aqueous saline solution (0.9% by weight) is poured into the perspex tube in one shot. Amount of time needed for the fluid to be fully absorbed into the fluid-absorbent article is recorded. After 10 minutes have elapsed, the load is removed and the stack of 10 filter papers (Whatman®) having 9 cm diameter and known dry weight (W1) is placed over the insult point on the fluid-absorbent article. On top of the filter paper, the 2.5 kg weight with 8 cm diameter is added. After 2 minutes have elapsed the weight is removed and filter paper reweighed giving the wet weight value (W2).

The rewet under load is calculated as follows:

$$RUL\ [g]=W2-W1$$

For the rewet under load of the secondary insult the procedure for the primary insult is repeated. 50 g of aqueous saline solution (0.9% by weight) and 20 filter papers are used.

For the rewet under load of the tertiary and following insults the procedure for the primary insult is repeated. For each of the following insults $3^{rd}$, $4^{th}$ and $5^{th}$ 50 g of aqueous saline solution (0.9% by weight) and 30, 40 and 50 filter papers respectively are used.

Rewet Value (RV)

This test consists of multiple insults of aqueous saline solution (0.9% by weight). The rewet value is measured by the amount of fluid the fluid-absorbent article released under pressure. The rewet is measured after each insult.

The fluid-absorbent article is clamped nonwoven side upward onto the inspection table. The insult point is marked accordingly with regard to the type and gender of the diaper to be tested (i.e. in the centre of the core for girl, 2.5 cm towards the front for unisex and 5 cm towards the front for boy). A separatory funnel is positioned above the fluid-absorbent article so that the spout is directly above the marked insult point.

For the primary insult 100 g of aqueous saline solution (0.9% by weight) is poured into the fluid-absorbent article via the funnel in one shot. The liquid is allowed to be absorbed for 10 minutes, and after that time the stack of 10 filter papers (Whatman®) having 9 cm diameter and known dry weight (D1) is placed over the insult point on the fluid-absorbent article. On top of the filter paper, the 2.5 kg weight with 8 cm diameter is added. After 2 minutes have elapsed the weight is removed and filter paper reweighed giving the wet weight value (D2).

The rewet value is calculated as follows:

$$RV\ [g]=D2-D1$$

For the rewet of the secondary insult the procedure for the primary insult is repeated. 50 g of aqueous saline solution (0.9% by weight) and 20 filter papers are used.

For the rewet of the tertiary and following insults the procedure for the primary insult is repeated. For each of the following insults $3^{rd}$, $4^{th}$ and $5^{th}$ 50 g of aqueous saline solution (0.9% by weight) and 30, 40 and 50 filter papers respectively are used.

The EDANA test methods are obtainable, for example, from the EDANA, Avenue Eugène Plasky 157, B-1030 Brussels, Belgium.

EXAMPLES

Preparation of the Base Polymer

Example 1

The process was performed in a concurrent spray drying plant with an integrated fluidized bed (27) and an external fluidized bed (29) as shown in FIG. 1. The cylindrical part of the spray dryer (5) had a height of 22 m and a diameter of 3.4 m. The internal fluidized bed (IFB) had a diameter of 3 m and a weir height of 0.25 m. The external fluidized bed (EFB) had a length of 3.0 m, a width of 0.65 m and a weir height of 0.5 m.

The drying gas was fed via a gas distributor (3) at the top of the spray dryer. The drying gas was partly recycled (drying gas loop) via a baghouse filter (9) and a condenser column (12). The drying gas was nitrogen that comprises from 1% to 4% by volume of residual oxygen: Before start of polymerization the drying gas loop was filled with nitrogen until the residual oxygen was below 4% by volume. The gas velocity of the drying gas in the cylindrical part of the spray dryer (5) was 0.8 m/s. The pressure inside the spray dryer was 4 mbar below ambient pressure.

The spray dryer outlet temperature was measured at three points around the circumference at the end of the cylindrical part as shown in FIG. 3. Three single measurements (47) were used to calculate the average cylindrical spray dryer outlet temperature. The drying gas loop was heated up and the dosage of monomer solution is started up. From this time the spray dryer outlet temperature was controlled to 117° C. by adjusting the gas inlet temperature via the heat exchanger (20).

The product accumulated in the internal fluidized bed (27) until the weir height was reached. Conditioned internal fluidized bed gas having a temperature of 122° C. and a relative humidity of 4% was fed to the internal fluidized bed (27) via line (25). The gas velocity of the internal fluidized bed gas in the internal fluidized bed (27) was 0.80 m/s. The residence time of the product was 120 min.

The spray dryer offgas was filtered in baghouse filter (9) and sent to a condenser column (12) for quenching/cooling. Excess water was pumped out of the condenser column (12) by controlling the (constant) filling level inside the condenser column (12). The water inside the condenser column (12) was cooled by a heat exchanger (13) and pumped counter-current to the gas via quench nozzles (11) so that the temperature inside the condenser column (12) was 45° C. The water inside the condenser column (12) was set to an alkaline pH by dosing sodium hydroxide solution to wash out acrylic acid vapors.

The condenser column offgas was split to the drying gas inlet pipe (1) and the conditioned internal fluidized bed gas (25). The gas temperatures were controlled via heat exchangers (20) and (22). The hot drying gas was fed to the concurrent spray dryer via gas distributor (3). The gas distributor (3) consists of a set of plates providing a pressure drop of 2 to 4 mbar depending on the drying gas amount.

The product was discharged from the internal fluidized bed (27) via rotary valve (28) into external fluidized bed (29). Conditioned external fluidized bed gas having a temperature of 60° C. was fed to the external fluidized bed (29) via line (40). The external fluidized bed gas was air. The gas velocity of the external fluidized bed gas in the external fluidized bed (29) was 0.8 m/s. The residence time of the product was 1 min.

The product was discharged from the external fluidized bed (29) via rotary valve (32) into sieve (32). The sieve (33) was used for sieving off overs/lumps having a particle diameter of more than 800 µm.

The monomer solution was prepared by mixing first acrylic acid with 3-tuply ethoxylated glycerol triacrylate (internal crosslinker) and secondly with 37.3% by weight sodium acrylate solution. The temperature of the resulting monomer solution was controlled to 10° C. by using a heat exchanger and pumping in a loop. A filter unit having a mesh size of 250 µm was used in the loop after the pump. The initiators were metered into the monomer solution upstream of the dropletizer by means of static mixers (41) and (42) via lines (43) and (44) as shown in FIG. 1. Sodium peroxodisulfate solution having a temperature of 20° C. was added via line (43) and [2,2'-azobis[2-(2-imidazolin-2-yl)propane]dihydrochloride solution together with Bruggolite FF7 having a temperature of 5° C. was added via line (44). Each initiator was pumped in a loop and dosed via control valves to each dropletizer unit. A second filter unit having a mesh size of 140 µm was used after the static mixer (42). For dosing the monomer solution into the top of the spray dryer three dropletizer units were used as shown in FIG. 4.

A dropletizer unit consisted of an outer pipe (51) having an opening for the dropletizer cassette (53) as shown in FIG. 5. The dropletizer cassette (53) was connected with an inner pipe (52). The inner pipe (53) having a PTFE block (54) at the end as sealing can be pushed in and out of the outer pipe (51) during operation of the process for maintenance purposes.

The temperature of the dropletizer cassette (61) was controlled to 8° C. by water in flow channels (59) as shown in FIG. 6. The dropletizer cassette (61) had 256 bores having a diameter of 170 µm and a bore separation of 15 mm. The dropletizer cassette (61) consisted of a flow channel (60) having essential no stagnant volume for homogeneous distribution of the premixed monomer and initiator solutions and one droplet plate (57). The droplet plate (57) had an angled configuration with an angle of 3°. The droplet plate (57) was made of stainless steel and had a length of 630 mm, a width of 128 mm and a thickness of 1 mm.

The feed to the spray dryer consisted of 10.45% by weight of acrylic acid, 33.40% by weight of sodium acrylate, 0.018% by weight of 3-tuply ethoxylated glycerol triacrylate, 0.072% by weight of [2,2'-azobis[2-(2-imidazolin-2-yl) propane]dihydrochloride, 0.0029% by weight of Bruggolite FF7 (5% by weight in water), 0.054% by weight of sodiumperoxodisulfate solution (15% by weight in water) and water. The degree of neutralization was 71%. The feed per bore was 1.6 kg/h.

The polymer particles (base polymer A1) exhibit the following features and absorption profile:
CRC of 40.2 g/g
AUNL of 51.8 g/g
AUL of 22.4 g/g
AUHL of 8.2 g/g
Porosity of 22.3%
Extractables of 4.3 wt. %
Residual monomers of 12161 ppm
Moisture content of 6.1 wt. %
Vortex time of 67 s The resulting polymer particles had a bulk density of 68 g/100 ml and an average particle diameter of 407 µm.

Example 2

Example 1 was repeated, except that the resulting polymer particles having a content of the residual monomer of 12161 ppm were demonomerized in a plastic bottle in the lab oven at 90° C. for 60 minutes after spraying 15% by weight of water onto the polymer particles in a laboratory ploughshare mixer. Therefore the content of the residual monomer was decreased to 256 ppm and the moisture content was increased to 17.5% by weight.

The polymer particles (base polymer B1) exhibit the following features and absorption profile:
CRC of 33.1 g/g
AUNL of 42.3 g/g
AUL of 17.0 g/g
AUHL of 8.1 g/g
Porosity of 21.7%
Extractables of 8.2 wt. %
Residual monomers of 256 ppm
Moisture content of 17.5 wt. %
Vortex time of 54 s Example 3

Example 1 was repeated, except that the feed to the spray dryer consisted of 0.036% by weight of [2,2'-azobis[2-(2-imidazolin-2-yl)propane]dihydrochloride and that the conditioned internal fluidized bed gas had a temperature of 122° C. and a relative humidity of 4% and that the residence time of the product in the internal fluidized bed was 120 min.

The polymer particles (base polymer C1) exhibit the following features and absorption profile:
CRC of 39.5 g/g
AUNL of 51.4 g/g
AUHL of 9.0 g/g
Porosity of 23.2%
Residual monomers of 1581 ppm
Moisture content of 10.9 wt. %

Surface-Postcrosslinking of the Base Polymer

Example 4

1200 g of the water-absorbent polymer particles prepared in Example 1 (base polymer A1) having a content of residual monomers of 12161 ppm were put into a laboratory ploughshare mixer (model MR5, manufactured by Gebrüder Lödige Maschinenbau GmbH; Paderborn; Germany). A surface-postcrosslinker solution was prepared by mixing 60 g of surface-postcrosslinker as described in Table 1 and 60 g of deionized water, into a beaker. At a mixer speed of 200 rpm, the aqueous solution was sprayed onto the polymer particles within one minute by means of a spray nozzle. The mixing was continued for additional 5 minutes. The product was removed and transferred into another ploughshare mixer (model MR5, manufactured by Gebrüder Lödige Maschinenbau GmbH; Paderborn; Germany) which was heated to 140° C. before. After mixing for further 80 minutes at 140° C. with sample taking every 10 minutes, the product was removed from the mixer and sifted from 150 to 850 µm. The samples were analyzed. The results are summarized in Table 1.

The resulting polymer particles that were surface-postcrosslinked with ethylene carbonate had a bulk density of 69.0 g/100 ml, an average particle diameter (APD) of 481 µm, a particle diameter distribution (PDD) of 0.28, and a mean sphericity of 0.82.

TABLE 1

Effect of the postcrosslinking agent

| Postcross-linker | Curing Time [min] | Residual Monomers [ppm] | Moisture [wt. %] | CRC [g/g] | AUNL [g/g] | AUL [g/g] | AUHL [g/g] | Porosity [%] | Extractables [wt. %] | Vortex [s] |
|---|---|---|---|---|---|---|---|---|---|---|
| EC | 10 | 533 | 10.1 | 49.2 | 58.1 | 18.8 | 8.2 | 15.3 | 5.3 | 78 |
|  | 20 | 384 | 7.0 | 51.4 | 60.8 | 20.6 | 8.0 | 15.5 | 4.5 | 77 |
|  | 30 | 376 | 5.1 | 51.6 | 61.0 | 28.0 | 9.5 | 15.4 | 4.8 | 76 |
|  | 40 | 386 | 3.6 | 50.5 | 62.1 | 31.9 | 12.9 | 18.7 | 3.8 | 74 |
|  | 50 | 432 | 1.9 | 49.1 | 61.8 | 36.2 | 18.2 | 20.6 | 3.4 | 70 |
|  | 60 | 416 | 1.1 | 47.3 | 61.2 | 37.9 | 22.2 | 22.7 | 3.1 | 75 |
|  | 70 | 417 | 0.6 | 46.7 | 62.5 | 38.6 | 24.3 | 25.3 | 3.1 | 75 |
|  | 80 | 429 | 0.4 | 46.2 | 62.6 | 39.5 | 24.2 | 26.2 | 3.1 | 75 |
| HEONON | 10 | 1538 | 7.6 | 50.2 | 58.4 | 16.6 | 7.7 | 14.0 | 7.0 | 86 |
|  | 20 | 1377 | 5.3 | 51.3 | 59.7 | 16.3 | 7.8 | 14.1 | 6.8 | 85 |
|  | 30 | 1153 | 3.7 | 52.5 | 61.3 | 17.7 | 7.9 | 14.4 | 7.1 | 84 |
|  | 40 | 1061 | 2.8 | 51.5 | 61.4 | 19.8 | 8.0 | 16.1 | 6.6 | 86 |
|  | 50 | 1002 | 2.5 | 50.9 | 60.3 | 25.2 | 8.7 | 15.6 | 6.3 | 85 |
|  | 60 | 997 | 2.4 | 49.1 | 59.9 | 27.7 | 10.3 | 18.0 | 6.0 | 82 |
|  | 70 | 939 | 2.2 | 48.1 | 59.8 | 30.0 | 13.1 | 19.6 | 5.8 | 81 |
|  | 80 | 913 | 2.0 | 47.3 | 59.3 | 32.6 | 16.2 | 20.2 | 5.1 | 81 |
| EGDGE | 10 | 714 | 8.0 | 34.2 | 43.7 | 23.1 | 17.1 | 21.7 | 22.1 | 95 |
|  | 20 | 572 | 5.4 | 35.2 | 44.7 | 23.6 | 17.2 | 21.3 | 23.3 | 93 |
|  | 30 | 554 | 3.9 | 35.9 | 45.0 | 24.2 | 17.8 | 20.2 | 23.8 | 91 |
|  | 40 | 549 | 2.8 | 36.3 | 45.5 | 24.4 | 18.0 | 20.2 | 24.2 | 94 |
|  | 50 | 544 | 2.2 | 36.6 | 46.2 | 24.5 | 18.3 | 20.8 | 23.5 | 96 |
|  | 60 | 550 | 1.9 | 36.6 | 45.9 | 23.8 | 18.4 | 20.3 | 23.8 | 93 |
|  | 70 | 542 | 1.6 | 36.5 | 46.3 | 23.8 | 18.4 | 21.2 | 23.9 | 94 |
|  | 80 | 562 | 1.4 | 37.1 | 46.4 | 24.0 | 18.5 | 20.0 | 24.1 | 92 |

EC: Ethylene carbonate;
HEONON: N-(2-hydroxy ethyl)-2-oxazolidinone;
EGDGE: Ethylene glycol diglycidyl ether Example 5

1200 g of the water-absorbent polymer particles as described in Table 2 having different contents of residual monomers were put into a laboratory ploughshare mixer (model MR5, manufactured by Gebrüder Lödige Maschinenbau GmbH; Paderborn; Germany). A surface-postcrosslinker solution was prepared by mixing 30 g ethylene carbonate and 30 g of deionized water, into a beaker. At a mixer speed of 200 rpm, the aqueous solution was sprayed onto the polymer particles within one minute by means of a spray nozzle. The mixing was continued for additional 5 minutes. The product was removed and transferred into another ploughshare mixer (model MR5, manufactured by Gebrüder Lödige Maschinenbau GmbH; Paderborn; Germany) which was heated to 150° C. before. After mixing for further 80 minutes at 150° C. with sample taking every 10 minutes, the product was removed from the mixer and sifted from 150 to 850 μm. The samples were analyzed. The results are summarized in Table 2.

The resulting polymer particles based on base polymer A1 had a bulk density of 68.0 g/100 ml, an average particle diameter (APD) of 397 μm, a particle diameter distribution (PDD) of 0.38, and a mean sphericity of 0.87.

The resulting polymer particles based on base polymer B1 had a bulk density of 64.7 g/100 ml, an average particle diameter (APD) of 553 μm, a particle diameter distribution (PDD) of 0.25, and a mean sphericity of 0.74.

The resulting polymer particles based on base polymer C1 had a bulk density of 69.8 g/100 ml, an average particle diameter (APD) of 377 μm, a particle diameter distribution (PDD) of 0.42, and a mean sphericity of 0.86.

Example 6

1200 g of the water-absorbent polymer particles as described in Table 3 having different contents of residual monomers were put into a laboratory ploughshare mixer (model MR5, manufactured by Gebrüder Lödige Maschinenbau GmbH; Paderborn; Germany). A surface-postcrosslinker solution was prepared by mixing 30 g ethylene carbonate and 60 g of deionized water, into a beaker. At a mixer speed of 200 rpm, the aqueous solution was sprayed onto the polymer particles within one minute by means of a spray nozzle. The mixing was continued for additional 5 minutes. The product was removed and transferred into another ploughshare mixer (model MR5, manufactured by Gebrüder Lödige Maschinenbau GmbH; Paderborn; Germany) which was heated to 140° C. before. After mixing for further 80 minutes at 140° C. with sample taking every 10 minutes, the product was removed from the mixer and sifted from 150 to 850 μm. The samples were analyzed. The results are summarized in Table 3.

The resulting polymer particles based on base polymer A1 had a bulk density of 65.6 g/100 ml, an average particle diameter (APD) of 450 μm, a particle diameter distribution (PDD) of 0.32, and a mean sphericity of 0.82.

The resulting polymer particles based on base polymer B1 had a bulk density of 64.7 g/100 ml, an average particle diameter (APD) of 564 μm, a particle diameter distribution (PDD) of 0.22, and a mean sphericity of 0.75.

The resulting polymer particles based on base polymer C1 had a bulk density of 70.3 g/100 ml, an average particle diameter (APD) of 399 μm, a particle diameter distribution (PDD) of 0.36, and a mean sphericity of 0.84.

TABLE 2

Effect of the residual monomers

| Base Polymer | Curing Time [min] | Residual Monomers [ppm] | Moisture [wt. %] | CRC [g/g] | AUNL [g/g] | AUL [g/g] | AUHL [g/g] | Porosity [%] | Extractables [wt. %] | Vortex [s] |
|---|---|---|---|---|---|---|---|---|---|---|
| Base Polymer A1 | 10 | 2187 | 5.2 | 57.5 | 61.4 | 11.0 | 7.6 | 6.4 | 8.4 | |
| | 20 | 1646 | 3.0 | 57.7 | 63.8 | 12.6 | 8.2 | 9.6 | 7.2 | |
| | 30 | 1273 | 1.5 | 53.5 | 65.4 | 33.5 | 11.6 | 18.2 | 5.3 | |
| | 40 | 1229 | 0.5 | 51.5 | 63.9 | 38.6 | 18.8 | 19.4 | 4.7 | |
| | 50 | 1225 | 0.5 | 49.7 | 63.5 | 40.6 | 24.5 | 21.7 | 5.0 | |
| | 60 | 1214 | 0.3 | 47.6 | 63.5 | 40.8 | 27.6 | 25.0 | 6.1 | 70 |
| | 70 | 1243 | 0.3 | 48.1 | 62.7 | 40.3 | 30.2 | 23.3 | 6.2 | 69 |
| | 80 | 1225 | 0.1 | 46.4 | 60.1 | 38.2 | 30.7 | 22.8 | 6.3 | 67 |
| Base Polymer B1 | 10 | 133 | 13.7 | 35.8 | | | | | | |
| | 20 | 133 | 8.4 | 36.9 | | | | | | |
| | 30 | 136 | 3.3 | 35.5 | | | | | | 89 |
| | 40 | 157 | 1.9 | 33.2 | | | | | | 7.5 | 93 |
| | 50 | 160 | 1.3 | 30.9 | 43.0 | 27.7 | 18.9 | 28.1 | | 92 |
| | 60 | 166 | 0.9 | 28.8 | 40.9 | 27.3 | 20.3 | 29.6 | | 95 |
| | 70 | 172 | 0.7 | 26.7 | 38.2 | 26.6 | 21.2 | 30.1 | | 94 |
| | 80 | 178 | 0.7 | 25.9 | 36.9 | 26.4 | 21.2 | 29.8 | 3.7 | 94 |
| Base Polymer C1 | 10 | 399 | 8.0 | 42.2 | 53.8 | 28.1 | 10.7 | 21.6 | | 70 |
| | 20 | 398 | 3.8 | 43.3 | 56.6 | 32.1 | 13.6 | 23.5 | | 70 |
| | 30 | 417 | 1.8 | 44.1 | 56.9 | 36.4 | 21.7 | 22.5 | | 71 |
| | 40 | 446 | 1.3 | 43.0 | 55.9 | 38.4 | 25.4 | 23.1 | 3.1 | 73 |
| | 50 | 419 | 1.0 | 39.5 | 54.3 | 36.9 | 29.0 | 27.3 | | 73 |
| | 60 | 413 | 0.8 | 38.7 | 52.1 | 37.0 | 29.5 | 25.7 | | 75 |
| | 70 | 403 | 0.6 | 37.6 | 51.6 | 36.2 | 29.4 | 27.1 | | 76 |
| | 80 | 402 | 0.6 | 36.4 | 51.3 | 35.0 | 29.7 | 29.0 | 3.3 | 76 |

TABLE 3

Effect of the residual monomers

| Base Polymer | Curing Time [min] | Residual Monomers [ppm] | Moisture [wt. %] | CRC [g/g] | AUNL [g/g] | AUL [g/g] | AUHL [g/g] | Porosity [%] | Extractables [wt. %] | Vortex [s] |
|---|---|---|---|---|---|---|---|---|---|---|
| Base Polymer A1 | 10 | 506 | 7.7 | 51.7 | 59.3 | 17.4 | 7.8 | 12.8 | 5.9 | |
| | 20 | 417 | 4.9 | 53.0 | 61.2 | 22.1 | 8.0 | 13.4 | 5.5 | |
| | 30 | 312 | 2.7 | 51.6 | 61.9 | 29.8 | 10.8 | 16.6 | 4.8 | |
| | 40 | 328 | 2.0 | 52.2 | 62.3 | 35.5 | 14.6 | 16.2 | 4.1 | |
| | 50 | 359 | 1.1 | 50.1 | 62.1 | 37.3 | 19.0 | 19.3 | 4.3 | |
| | 60 | 370 | 0.8 | 49.5 | 62.9 | 38.4 | 22.6 | 21.3 | 4.3 | |
| | 70 | 385 | 0.7 | 47.1 | 61.9 | 39.0 | 25.4 | 23.9 | 4.2 | 73 |
| | 80 | 340 | 0.5 | 45.3 | 60.3 | 37.9 | 27.5 | 24.9 | 4.0 | 72 |
| Base Polymer B1 | 10 | | | 33.7 | | | | | | |
| | 20 | | 0.8 | 36.1 | | | 8.1 | | | |
| | 30 | | | 36.1 | | | 8.6 | | | |
| | 40 | 123 | 4.1 | 35.4 | 48.1 | 22.9 | 10.2 | 26.4 | | |
| | 50 | 124 | 2.8 | 33.8 | 46.5 | 25.8 | 11.7 | 27.3 | | 87 |
| | 60 | 125 | 2.3 | 32.6 | 45.0 | 25.4 | 13.1 | 27.6 | | 88 |
| | 70 | 132 | 0.9 | 31.9 | 44.8 | 26.1 | 14.4 | 28.8 | | 92 |
| | 80 | 138 | 0.8 | 31.2 | 43.8 | 26.4 | 13.7 | 28.8 | | 90 |
| Base Polymer C1 | 10 | 373 | 9.6 | 41.1 | 52.9 | 28.8 | 13.1 | 22.0 | | 70 |
| | 20 | 356 | 5.6 | 42.6 | 55.1 | 31.5 | 14.4 | 23.0 | | 71 |
| | 30 | 362 | 3.0 | 42.0 | 55.6 | 34.1 | 19.6 | 24.0 | | 72 |
| | 40 | 378 | 1.3 | 42.2 | 55.8 | 34.8 | 23.2 | 24.0 | 4.2 | 73 |
| | 50 | 381 | 1.1 | 41.4 | 55.2 | 34.7 | 24.9 | 25.0 | | 73 |
| | 60 | 389 | 0.7 | 40.2 | 55.4 | 35.2 | 26.0 | 27.0 | | 72 |
| | 70 | 396 | 0.6 | 40.9 | 53.9 | 34.4 | 26.8 | 24.0 | | 70 |
| | 80 | 395 | 0.4 | 40.6 | 53.5 | 35.2 | 26.6 | 24.0 | 4.2 | 72 |

Example 7

The process was performed in a concurrent spray drying plant with an integrated fluidized bed (27) and an external fluidized bed (29) as shown in FIG. 1. The cylindrical part of the spray dryer (5) had a height of 22 m and a diameter of 3.4 m. The internal fluidized bed (IFB) had a diameter of 3 m and a weir height of 0.25 m.

The drying gas was fed via a gas distributor (3) at the top of the spray dryer. The drying gas was partly recycled (drying gas loop) via a baghouse filter (9) and a condenser column (12). Instead of the baghouse filter (9) any other filter and/or cyclone can be used. The drying gas was nitrogen that comprises from 1% to 4% by volume of residual oxygen: Before start of polymerization the drying gas loop was filled with nitrogen until the residual oxygen was below 4% by volume. The gas velocity of the drying gas in the cylindrical part of the spray dryer (5) was 0.82 m/s. The pressure inside the spray dryer was 4 mbar below ambient pressure.

The spray dryer outlet temperature was measured at three points around the circumference at the end of the cylindrical part as shown in FIG. 3. Three single measurements (47) were used to calculate the average cylindrical spray dryer outlet temperature. The drying gas loop was heated up and the dosage of monomer solution is started up. From this time the spray dryer outlet temperature was controlled to 118° C. by adjusting the gas inlet temperature via the heat exchanger (20). The gas inlet temperature was 167° C. and the steam content of the drying gas was 0.058 kg steam per kg dry gas.

The product accumulated in the internal fluidized bed (27) until the weir height was reached. Conditioned internal fluidized bed gas having a temperature of 104° C. and a steam content of 0.058 or 0.130 kg steam per kg dry gas was fed to the internal fluidized bed (27) via line (25). The gas velocity of the internal fluidized bed gas in the internal fluidized bed (27) was 0.65 m/s. The residence time of the product was 150 min. The temperature of the water-absorbent polymer particles in the internal fluidized bed was 82° C.

The spray dryer offgas was filtered in baghouse filter (9) and sent to a condenser column (12) for quenching/cooling. Excess water was pumped out of the condenser column (12) by controlling the (constant) filling level inside the condenser column (12). The water inside the condenser column (12) was cooled by a heat exchanger (13) and pumped counter-current to the gas via quench nozzles (11) so that the temperature inside the condenser column (12) was 45° C. The water inside the condenser column (12) was set to an alkaline pH by dosing sodium hydroxide solution to wash out acrylic acid vapors.

The condenser column offgas was split to the drying gas inlet pipe (1) and the conditioned internal fluidized bed gas (25). The gas temperatures were controlled via heat exchangers (20) and (22). The hot drying gas was fed to the concurrent spray dryer via gas distributor (3). The gas distributor (3) consists of a set of plates providing a pressure drop of 2 to 4 mbar depending on the drying gas amount.

The product was discharged from the internal fluidized bed (27) via rotary valve (28) into sieve (29). The sieve (29) was used for sieving off overs/lumps having a particle diameter of more than 800 μm.

The monomer solution was prepared by mixing first acrylic acid with 3-tuply ethoxylated glycerol triacrylate (internal crosslinker) and secondly with 37.3% by weight sodium acrylate solution. The temperature of the resulting monomer solution was controlled to 10° C. by using a heat exchanger and pumping in a loop. A filter unit having a mesh size of 250 μm was used in the loop after the pump. The initiators were metered into the monomer solution upstream of the dropletizer by means of static mixers (41) and (42) via lines (43) and (44) as shown in FIG. 1. Sodium peroxodisulfate solution having a temperature of 20° C. was added via line (43) and [2,2'-azobis[2-(2-imidazolin-2-yl)propane]dihydrochloride solution together with Bruggolite FF7 having a temperature of 5° C. was added via line (44). Each initiator was pumped in a loop and dosed via control valves to each dropletizer unit A second filter unit having a mesh size of 140 μm was used after the static mixer (42). For dosing the monomer solution into the top of the spray dryer three dropletizer units were used as shown in FIG. 4.

A dropletizer unit consisted of an outer pipe (51) having an opening for the dropletizer cassette (53) as shown in FIG. 5. The dropletizer cassette (53) was connected with an inner pipe (52). The inner pipe (53) having a PTFE block (54) at the end as sealing can be pushed in and out of the outer pipe (51) during operation of the process for maintenance purposes.

The temperature of the dropletizer cassette (61) was controlled to 8° C. by water in flow channels (59) as shown in FIG. 6. The dropletizer cassette (61) had 256 bores having a diameter of 170 μm and a bore separation of 15 mm. The dropletizer cassette (61) consisted of a flow channel (60) having essential no stagnant volume for homogeneous distribution of the premixed monomer and initiator solutions and one droplet plate (57). The droplet plate (57) had an angled configuration with an angle of 3°. The droplet plate (57) was made of stainless steel and had a length of 630 mm, a width of 128 mm and a thickness of 1 mm.

The feed to the spray dryer consisted of 10.45% by weight of acrylic acid, 33.40% by weight of sodium acrylate, 0.018% by weight of 3-tuply ethoxylated glycerol triacrylate, 0.036% by weight of [2,2'-azobis[2-(2-imidazolin-2-yl)propane]dihydrochloride, 0.0029% by weight of Bruggolite FF7, 0.054% by weight of sodium peroxodisulfate and water. The degree of neutralization was 71%. The feed per bore was 1.4 kg/h.

The resulting water-absorbent polymer particles were analyzed. The results are summarized in Table 4.

TABLE 4

Base polymers, used for the surface-postcrosslinking reactions

| Example | Steam Content [kg/kg] | Bulk Density [g/cm$^3$] | CRC [g/g] | Residual Monomers [ppm] | Extractables [wt. %] | Moisture [wt. %] | FSR [g/gs] |
|---|---|---|---|---|---|---|---|
| 7a | 0.058 | 0.74 | 47.2 | 9300 | 4.5 | 5.7 | 0.20 |
| 7b | 0.130 | 0.71 | 49.1 | 4000 | 5.4 | 7.5 | 0.07 |

Examples 8 to 26

Figure 13:
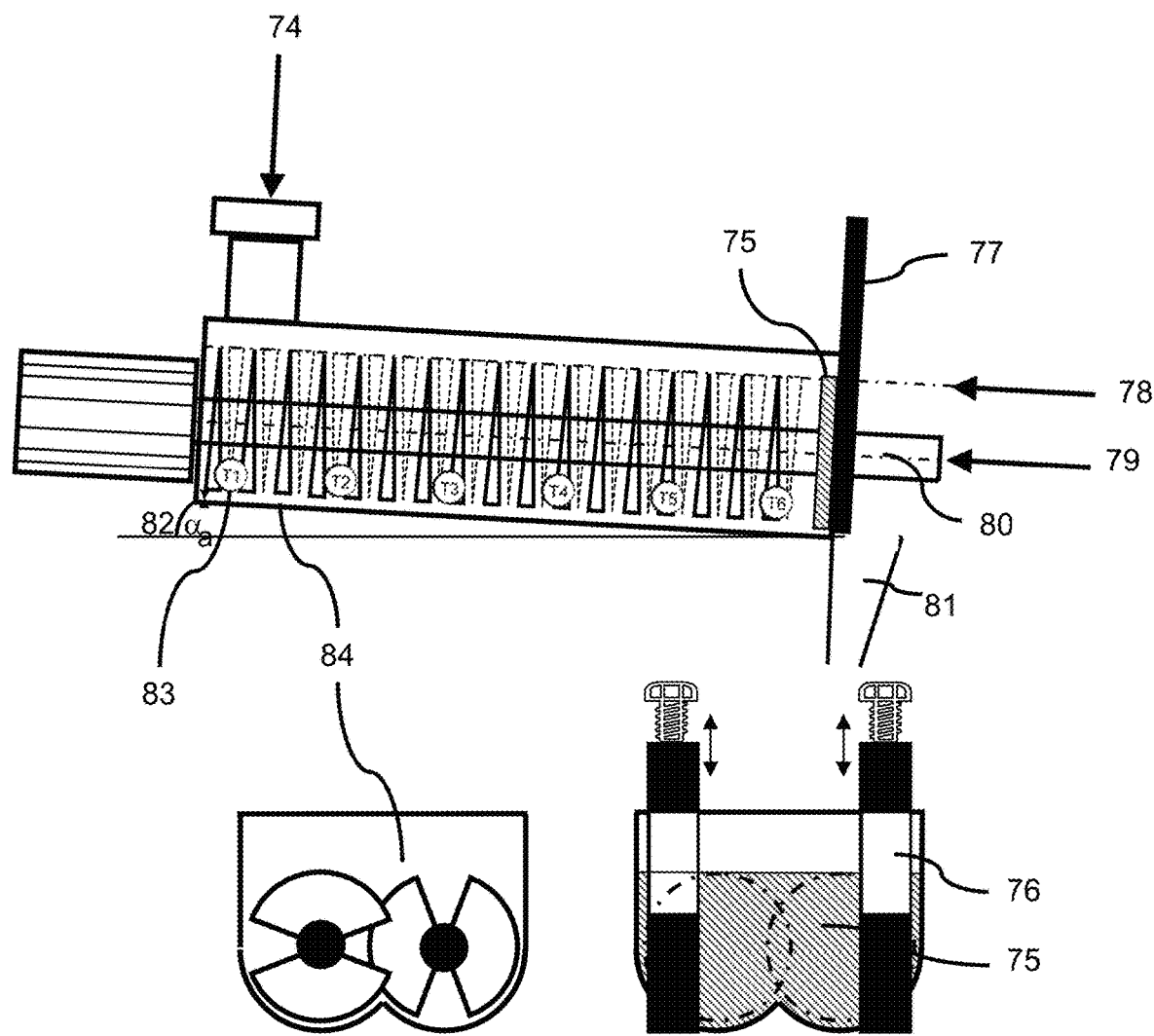
FIG. 13 illustrates a contact dryer for surface-postcrosslinking.

In a Schugi Flexomix® (model Flexomix-160, manufactured by Hosokawa Micron B.V., Doetinchem, the Netherlands) with a speed of 2000 rpm, the base polymer 7a or 7b was coated with a surface-postcrosslinker solution by using 2 or 3 round spray nozzle systems (model Gravity-Fed Spray Set-ups, External Mix Typ SU4, Fluid Cap 60100 and Air Cap SS-120, manufactured by Spraying Systems Co, Wheaton, Ill., USA) and then filled via inlet (74) and dried in a NARA heater (model NPD SW-18, manufactured by GMF Gouda, Waddinxveen, the Netherlands) with a speed of the shaft (80) of 6 rpm. The NARA heater has two paddles with a shaft offset of 90° (84) and a fixed discharge zone (75) with two flexible weir plates (77). Each weir has a weir opening with a minimal weir height at 50% (79) and a maximal weir opening at 100% (78) as shown in FIG. 13.

The inclination angle α (82) between the floor plate and the NARA paddle dryer is approx. 3°. The weir height of the NARA heater is between 50 to 100% corresponding to a residence time of approx. 40 to 150 min, by a product density of approx. 700 to 750 kg/m$^3$. The product temperature in the NARA heater is in a range of 120 to 165° C. After drying, the surface-postcrosslinked base polymer was transported over discharge cone (81) in the NARA cooler (GMF Gouda, Waddinxveen, the Netherlands), to cool down the surface postcrosslinked base polymer to approx. 60° C. with a speed of 11 rpm and a weir height of 145 mm. After cooling, the material was sieved with a minimum cut size of 150 μm and a maximum size cut of 710 μm.

Ethylene carbonate, water, Plantacare® UP 818 (BASF SE, Ludwigshafen, Germany) and aqueous aluminum lactate (26% by weight) was premixed and spray coated as summarized in Tab 6. Aqueous aluminum sulfate (26% by weight) was separate spray coated (position of the nozzle=180°). As aluminum lactate, Lothragon® Al 220 (manufactured by Dr. Paul Lohmann GmbH, Emmerthal, Germany) was used.

The metered amounts and conditions of the coating into the Schugi Flexomix®, the conditions, the formulation and values of the drying and cooling step are summarized in Table 5 to 6:

All physical properties of the resulting polymers are summarized in Table 7 and 8:

TABLE 5

Process parameters of the thermal treatment in the heater

| Example | Product Temp. Set Value ° C. | Steam Pressure valve bar | Steam Pressure Jacket bar | Heater T1 ° C. | Heater T2 ° C. | Heater T3 ° C. | Heater T4 ° C. | Heater T5 ° C. | Heater T6 ° C. | Through-put kg/h | Heater Weir % | No. of Nozzles | Pos. of Nozzles |
|---|---|---|---|---|---|---|---|---|---|---|---|---|---|
| Polymer particles without aluminum salt |
| 8 | 140 | 4.6 | 4.3 | 84 | 81 | 111 | 123 | 130 | 140 | 400 | 56 | 2 | 90/270° |
| 9 | 150 | 6.2 | 6.2 | 90 | 86 | 115 | 129 | 137 | 150 | 400 | 56 | 2 | 90/270° |
| 10 | 150 | 7.4 | 7.4 | 79 | 81 | 110 | 121 | 133 | 159 | 500 | 67 | 3 | 90/180/270° |
| Polymer particles with aluminum lactate |
| 11 | 120 | 2.5 | 2.3 | 69 | 72 | 103 | 111 | 114 | 120 | 500 | 57 | 3 | 90/180/270° |
| 12 | 130 | 2.3 | 3.5 | 75 | 84 | 110 | 117 | 121 | 130 | 500 | 57 | 3 | 90/180/270° |
| 13 | 140 | 6.7 | 6.6 | 82 | 93 | 118 | 127 | 135 | 150 | 500 | 67 | 3 | 90/180/270° |
| 14 | 150 | 5.5 | 5.0 | 84 | 107 | 117 | 131 | 138 | 150 | 400 | 56 | 2 | 90/270° |
| 15 | 150 | 5.2 | 6.2 | 71 | 100 | 118 | 132 | 140 | 150 | 400 | 56 | 2 | 90/270° |
| 16 | 150 | 5.9 | 5.9 | 91 | 109 | 120 | 131 | 140 | 150 | 500 | 68 | 3 | 90/180/270° |
| 17 | 150 | 6.1 | 6.1 | 83 | 110 | 120 | 131 | 139 | 150 | 500 | 68 | 3 | 90/180/270° |
| 18 | 160 | 6.5 | 6.5 | 89 | 114 | 123 | 138 | 151 | 160 | 400 | 82 | 3 | 90/270° |
| 19 | 170 | 8.1 | 8.1 | 91 | 113 | 129 | 151 | 163 | 170 | 400 | 82 | 2 | 90/270° |
| Polymer particles with aluminum sulfate |
| 20 | 150 | 5.6 | 5.5 | 66 | 99 | 119 | 137 | 145 | 150 | 500 | 87 | 3 | 90/180/270° |
| 21 | 150 | 5.0 | 5.0 | 95 | 96 | 121 | 135 | 144 | 150 | 400 | 75 | 3 | 90/180/270° |
| 22 | 150 | 5.6 | 5.6 | 74 | 104 | 117 | 127 | 136 | 150 | 500 | 87 | 3 | 90/180/270° |
| 23 | 155 | 6.1 | 6.0 | 79 | 100 | 119 | 130 | 142 | 155 | 500 | 87 | 3 | 90/180/270° |
| 24 | 160 | 6.6 | 6.6 | 109 | 115 | 124 | 143 | 154 | 160 | 400 | 75 | 3 | 90/180/270° |
| 25 | 160 | 6.5 | 6.5 | 96 | 105 | 125 | 144 | 154 | 160 | 400 | 75 | 3 | 90/180/270° |
| 26 | 165 | 7.8 | 7.8 | 79 | 109 | 122 | 138 | 152 | 165 | 500 | 87 | 3 | 90/180/270° |

TABLE 6

Surface-postcrosslinker formulation of the thermal treatment in the heater

| Example | Base polymer | EC bop % | Water bop % | Plantacare 818 UP bop ppm | Al-lactate (dry) bop % | Al-sulfate (dry) bop % |
|---|---|---|---|---|---|---|
| Polymer particles without aluminum salt |
| 8 | 7b | 2.5 | 5.0 | 50 | | |
| 9 | 7b | 2.5 | 5.0 | 50 | | |
| 10 | 7b | 2.5 | 5.0 | 25 | | |
| Polymer particles with aluminum lactate |
| 11 | 7b | 2.5 | 5.0 | 25 | 0.5 | |
| 12 | 7b | 2.5 | 5.0 | 25 | 0.5 | |
| 13 | 7b | 1.5 | 5.0 | 50 | 0.5 | |
| 14 | 7a | 2.5 | 5.0 | | 0.5 | |
| 15 | 7a | 2.5 | 5.0 | 50 | 0.5 | |
| 16 | 7a | 2.5 | 5.0 | 25 | 0.5 | |
| 17 | 7b | 2.5 | 5.0 | 25 | 0.5 | |
| 18 | 7b | 2.5 | 5.0 | 25 | 0.5 | |
| 19 | 7a | 2.5 | 5.0 | 25 | 0.5 | |
| Polymer particles with aluminum sulfate |
| 20 | 7b | 2.5 | 5.0 | 25 | | 0.50 |
| 21 | 7a | 2.5 | 5.0 | 25 | | 0.36 |
| 22 | 7b | 2.5 | 5.0 | 25 | | 0.75 |
| 23 | 7b | 2.5 | 5.0 | 25 | | 0.50 |
| 24 | 7b | 2.5 | 5.0 | 50 | | 0.36 |

TABLE 6-continued

Surface-postcrosslinker formulation of the thermal treatment in the heater

| Example | Base polymer | EC bop % | Water bop % | Plantacare 818 UP bop ppm | Al-lactate (dry) bop % | Al-sulfate (dry) bop % |
|---|---|---|---|---|---|---|
| 25 | 7a | 2.5 | 5.0 | 25 | | 0.36 |
| 26 | 7b | 2.5 | 5.0 | 25 | | 0.50 |

EC: Ethylene carbonate;
bop: based on polymer

TABLE 7

Physical properties of the polymer particles after surface-postcrosslinking

| Example | CRC g/g | AUNL g/g | AUL g/g | AUHL g/g | SFC $10^{-7}$ cm³·s/g | GBP Da | Vortex s | FSR g/g·s | Moisture % | Residual Monomers ppm | Extractables % | Bulk Density g/100 ml | FR g/s | Fines <150 μm % | Overs >710 μm % |
|---|---|---|---|---|---|---|---|---|---|---|---|---|---|---|---|
| Polymer particles without aluminum salt | | | | | | | | | | | | | | | |
| 8 | 47 | 61 | 37 | 21 | 0 | 1 | 73 | 0.29 | 1.7 | 373 | 5 | 78 | 15 | 0.0 | 2.0 |
| 9 | 42 | 55 | 36 | 26 | 3 | 2 | 69 | 0.27 | 1.2 | 557 | 6 | 74 | 15 | 0.0 | 2.4 |
| 10 | 37 | 48 | 33 | 26 | 6 | 5 | 91 | 0.22 | 1.2 | 170 | 3 | 80 | 14 | 0.1 | 0.5 |
| Polymer particles with aluminum lactate | | | | | | | | | | | | | | | |
| 11 | 41 | 54 | 33 | 21 | 1 | 5 | 60 | 0.39 | 5.1 | 282 | 4 | 77 | 14 | 0.2 | 0.9 |
| 12 | 39 | 53 | 34 | 25 | 1 | 6 | 65 | 0.31 | 2.6 | 367 | 4 | 79 | 14 | 0.5 | 1.1 |
| 13 | 36 | 51 | 33 | 25 | 6 | 9 | 74 | 0.19 | 1.0 | 351 | 4 | 77 | 14 | 0.1 | 0.6 |
| 14 | 46 | 60 | 37 | 20 | 0 | 1 | 73 | 0.30 | 1.2 | 510 | 6 | 75 | 13 | 0.3 | 0.5 |
| 15 | 45 | 60 | 36 | 22 | 9 | 1 | 65 | 0.32 | 1.1 | 515 | 8 | 73 | 13 | 1.0 | 2.5 |
| 16 | 42 | 55 | 36 | 26 | 3 | 2 | 69 | 0.27 | 1.2 | 557 | 6 | 72 | 12 | 0.3 | 0.2 |
| 17 | 39 | 54 | 35 | 27 | 8 | 5 | 68 | 0.32 | 1.2 | 510 | 5 | 77 | 14 | 0.3 | 1.0 |
| 18 | 28 | 41 | 28 | 24 | 125 | 32 | 86 | 0.22 | 0.8 | 565 | 3 | 75 | 14 | 0.4 | 0.9 |
| 19 | 25 | 36 | 26 | 23 | 153 | 31 | 111 | 0.20 | 0.6 | 629 | 5 | 74 | 13 | 1.0 | 2.0 |
| Polymer particles with aluminum sulfate | | | | | | | | | | | | | | | |
| 20 | 32 | 49 | 29 | 22 | 41 | 36 | 70 | 0.30 | 1.2 | 421 | 4 | 79 | 14 | 0.4 | 0.5 |
| 21 | 37 | 53 | 33 | 25 | 23 | 17 | 74 | 0.31 | 1.1 | 373 | 6 | 78 | 13 | 1.0 | 2.6 |
| 22 | 28 | 43 | 25 | 20 | 93 | 78 | 75 | 0.25 | 1.2 | 296 | 3 | 80 | 15 | 0.3 | 0.7 |
| 23 | 28 | 43 | 27 | 22 | 106 | 59 | 89 | 0.22 | 0.9 | 375 | 3 | 81 | 14 | 0.1 | 0.0 |
| 24 | 32 | 48 | 30 | 24 | 65 | 35 | 80 | 0.29 | 0.6 | 594 | 5 | 75 | 13 | 0.3 | 1.0 |
| 25 | 35 | 52 | 32 | 23 | 24 | 25 | 66 | 0.30 | 0.7 | 684 | 7 | 75 | 13 | 1.1 | 2.0 |
| 26 | 24 | 36 | 24 | 20 | 275 | 100 | 100 | 0.21 | 0.6 | 360 | 3 | 80 | 15 | 0.2 | 0.1 |

TABLE 8

Physical properties of the polymer particles after surface-postcrosslinking

| Example | CRC g/g | τ 0.03 psi s | τ 0.1 psi s | τ 0.3 psi s | τ 0.5 psi s | τ 0.7 psi s | Total liquid uptake g |
|---|---|---|---|---|---|---|---|
| Polymer particles with aluminum salt | | | | | | | |
| 8 | 47.1 | 464 | 525 | 659 | 832 | 924 | 61.5 |
| 9 | 41.7 | 418 | 501 | 546 | 678 | 716 | 108.9 |
| 10 | 36.5 | 324 | 387 | 437 | 571 | 568 | 149.5 |
| Polymer particles with aluminum lactate | | | | | | | |
| 11 | 40.8 | 490 | 611 | 493 | 439 | 383 | 73.5 |
| 12 | 38.7 | 463 | 563 | 538 | 489 | 465 | 86.2 |
| 13 | | | | | | | 136.0 |
| 14 | 46.4 | 467 | 551 | 598 | 599 | 596 | 54.7 |
| 15 | 46.3 | 466 | 551 | 535 | 535 | 497 | 62.9 |
| 16 | 42.6 | | | | | | 93.3 |
| 17 | 26.9 | | | | | | 261.1 |
| 18 | 27.6 | 235 | 281 | 407 | 393 | 391 | 261.0 |
| 19 | 25.3 | | | | | | 324.6 |
| Polymer particles with aluminum sulfate | | | | | | | |
| 20 | 31.7 | | | | | | 134.0 |
| 21 | 37.7 | | | | | | 105.8 |
| 22 | 27.5 | | | | | | 171.3 |
| 23 | 28.2 | 272 | 323 | 382 | 436 | 494 | 167.8 |
| 24 | 32.4 | 295 | 358 | 418 | 404 | 363 | 158.3 |
| 25 | 35.0 | 309 | 376 | 401 | 389 | 385 | 125.8 |
| 26 | 23.6 | 210 | 258 | 278 | 358 | 338 | 218.3 |

Example 27

1200 g of the water-absorbent polymer particles prepared in Example 7b (base polymer) having a content of residual monomers of 4000 ppm were put into a laboratory ploughshare mixer (model MR5, manufactured by Gebrüder Lödige Maschinenbau GmbH, Paderborn, Germany). A surface-postcrosslinker solution was prepared by mixing 12 g of 3-methyl-2-oxazolidinone as described in Table 1 and 60 g of deionized water, into a beaker. At a mixer speed of 200 rpm, the aqueous solution was sprayed onto the polymer particles within one minute by means of a spray nozzle. The mixing was continued for additional 5 minutes. The product was removed and transferred into another ploughshare mixer (model MR5, manufactured by Gebrüder Lödige Maschinenbau GmbH; Paderborn; Germany) which was heated to 150° C. before. After mixing for further 80 minutes at 150° C. with sample taking every 10 minutes, the product was removed from the mixer and sifted from 150 to 850 µm. The samples were analyzed. The results are summarized in Table 10.

The resulting polymer particles that were surface-postcrosslinked with 3-methyl-1,3-oxazolidin-2-one had a bulk density of 70.4 g/100 ml and a flow rate of 11.5 g/s.

Example 28

1200 g of the water-absorbent polymer particles prepared in Example 7b (base polymer) having a content of residual monomers of 4000 ppm were put into a laboratory ploughshare mixer (model MR5, manufactured by Gebrüder Lödige Maschinenbau GmbH; Paderborn; Germany). A surface-postcrosslinker solution was prepared by mixing 6 g of 3-Methyl-3-oxethanmethanol as described in Table 9 and 60 g of deionized water, into a beaker. At a mixer speed of 200 rpm, the aqueous solution was sprayed onto the polymer particles within one minute by means of a spray nozzle. The mixing was continued for additional 5 minutes. The product was removed and transferred into another ploughshare mixer (model MR5, manufactured by Gebrüder Lödige Maschinenbau GmbH, Paderborn, Germany) which was heated to 150° C. before. After mixing for further 80 minutes at 150° C. with sample taking every 10 minutes, the product was removed from the mixer and sifted from 150 to 850 µm. The samples were analyzed. The results are summarized in Table 10.

The resulting polymer particles that were surface-postcrosslinked with 3-methyl-3-oxethanmethanol had a bulk density of 72.2/100 ml and a flow rate of 12.0 g/s.

Example 29

1200 g of the water-absorbent polymer particles prepared in Example 7b (base polymer) having a content of residual monomers of 4000 ppm were put into a laboratory ploughshare mixer (model MR5, manufactured by Gebrüder Lödige Maschinenbau GmbH, Paderborn, Germany). A surface-postcrosslinker solution was prepared by mixing 6 g of 2-oxazolidinone as described in Table 9 and 60 g of deionized water, into a beaker. At a mixer speed of 200 rpm, the aqueous solution was sprayed onto the polymer particles within one minute by means of a spray nozzle. The mixing was continued for additional 5 minutes. The product was removed and transferred into another ploughshare mixer (model MR5, manufactured by Gebrüder Lödige Maschinenbau GmbH, Paderborn, Germany) which was heated to 150° C. before. After mixing for further 80 minutes at 150° C. with sample taking every 10 minutes, the product was removed from the mixer and sifted from 150 to 850 µm. The samples were analyzed. The results are summarized in Table 10.

The resulting polymer particles that were surface-postcrosslinked with 1,3-oxazolidin-2-one had a bulk density of 69.7 g/100 ml and a flow rate of 10.8 g/s.

Example 30

1200 g of the water-absorbent polymer particles prepared in Example 7b (base polymer) having a content of residual monomers of 4000 ppm were put into a laboratory ploughshare mixer (model MR5, manufactured by Gebrüder Lödige Maschinenbau GmbH, Paderborn, Germany). A surface-postcrosslinker solution was prepared by mixing 6 g of Solution of 3-(2-hydroxyethyl)-2-oxazolidinon and 6 g propandiol as described in Table 9 and 60 g of deionized water, into a beaker. At a mixer speed of 200 rpm, the aqueous solution was sprayed onto the polymer particles within one minute by means of a spray nozzle. The mixing was continued for additional 5 minutes. The product was removed and transferred into another ploughshare mixer (model MR5, manufactured by Gebrüder Lödige Maschinenbau GmbH, Paderborn, Germany) which was heated to 165° C. before. After mixing for further 80 minutes at 165° C. with sample taking every 10 minutes, the product was removed from the mixer and sifted from 150 to 850 µm. The samples were analyzed. The results are summarized in Table 10.

The resulting polymer particles that were surface-postcrosslinked with of 3-(2-hydroxyethyl)-1,3-oxazolidin-2-one and 6 g propandiol had a bulk density of 67.4 g/100 ml and a flow rate of 10.1 g/s.

Example 31

1200 g of the water-absorbent polymer particles prepared in Example 7b (base polymer) having a content of residual monomers of 4000 ppm were put into a laboratory ploughshare mixer (model MR5, manufactured by Gebrüder Lödige Maschinenbau GmbH, Paderborn, Germany). A surface-postcrosslinker solution was prepared by mixing 3 g of N,N,N',N'-Tetrakis(2-hydroxyethyl)adipamide (Primid® XL 552, manufactured by Ems Chemie AG; Domat; Switzerland) as described in Table 9 and 60 g of deionized water, into a beaker. At a mixer speed of 200 rpm, the aqueous solution was sprayed onto the polymer particles within one minute by means of a spray nozzle. The mixing was continued for additional 5 minutes. The product was removed and transferred into another ploughshare mixer (model MR5, manufactured by Gebrüder Lödige Maschinenbau GmbH, Paderborn, Germany) which was heated to 160° C. before. After mixing for further 80 minutes at 160° C. with sample taking every 10 minutes, the product was removed from the mixer and sifted from 150 to 850 µm. The samples were analyzed. The results are summarized in Table 10.

The resulting polymer particles that were surface-postcrosslinked with N,N,N',N'-Tetrakis(2-hydroxyethyl)adipamide had a bulk density of 65.8 g/100 ml and a flow rate of 10.2 g/s.

Example 32

1200 g of the water-absorbent polymer particles prepared in Example 7b (base polymer) having a content of residual monomers of 4000 ppm were put into a laboratory ploughshare mixer (model MR5, manufactured by Gebrüder Lödige Maschinenbau GmbH, Paderborn, Germany). A surface-postcrosslinker solution was prepared by mixing 24 g of 1.3-Dioxan-2-on as described in Table 9 and 60 g of deionized water, into a beaker. At a mixer speed of 200 rpm, the aqueous solution was sprayed onto the polymer particles within one minute by means of a spray nozzle. The mixing was continued for additional 5 minutes. The product was removed and transferred into another ploughshare mixer (model MR5, manufactured by Gebrüder Lödige Maschinenbau GmbH, Paderborn, Germany) which was heated to 160° C. before. After mixing for further 80 minutes at 160° C. with sample taking every 10 minutes, the product was removed from the mixer and sifted from 150 to 850 µm. The samples were analyzed. The results are summarized in Table 10.

The resulting polymer particles that were surface-postcrosslinked with 1.3-Dioxan-2-on had a bulk density of 68.4 g/100 ml and a flow rate of 10.5 g/s.

TABLE 9

Formulation of the polymer particles after surface-postcrosslinking by using different surface-postcrosslinkers

| Example | Surface-postcrosslinker - Typ | Surface-postcrosslinker bop % | Water bop % | Temperature ° C. | Time min | Base polymer |
|---|---|---|---|---|---|---|
| 27 | 3-Methyl-2-oxazolidinone | 1.00 | 5.0 | 150 | 80 | 7b |
| 28 | 3-Methyl-3-oxethanmethanol | 0.50 | 5.0 | 150 | 80 | 7b |
| 29 | 2-oxazolidinone | 0.50 | 5.0 | 150 | 80 | 7b |
| 30 | 50 wt % solution of 3-(2-hydroxyethyl)-2-oxazolidinone in 1,3-propandiol | 0.50 | 5.0 | 165 | 80 | 7b |
| 31 | N,N,N',N'-Tetrakis(2-hydroxyethyl)adipamide | 0.25 | 5.0 | 160 | 80 | 7b |
| 32 | 1,3-Dioxan-2-on | 2.0 | 5.0 | 160 | 80 | 7b |

Bop: based on polymer

TABLE 10

Physical properties of the polymer particles after surface-postcrosslinking by using different surface-postcrosslinkers

| Example | CRC g/g | AUNL g/g | AUL g/g | AUHL g/g | SFC $10^{-7}$ cm$^3 \cdot$ s/g | GBP Da | Vortex s | Total liquid uptake g |
|---|---|---|---|---|---|---|---|---|
| 27 | 41.9 | 56.4 | 36.1 | 24.8 | 0 | 2 | 83 | 114.8 |
| 28 | 41.3 | 55.0 | 33.9 | 22.8 | 0 | 0 | 61.5 | 92.5 |
| 29 | 39.3 | 53.1 | 33.0 | 22.1 | 9 | 13 | 54.5 | 102.2 |
| 30 | 30.9 | 43.1 | 29.2 | 23.6 | 0 | 2 | 83 | 208.5 |
| 31 | 34.3 | 46.3 | 30.5 | 24.1 | 6 | 8 | 104 | 91.9 |
| 32 | 39.2 | 53.6 | 36.6 | 30.1 | 12 | 25 | 87 | 110.5 |

Comparative Examples

AQUA KEEP® SA60SII, AQUA KEEP® SA55XSII, AQUA KEEP® SA60SXII are water-absorbent polymer particles from SUMITOMO SEIKA CHEMICALS CO., LTD, produced by a suspension polymerization process.

ASAP® 535, Hysorb® 87075, Hysorb® T9700, Hysorb® B7055, Hysorb® T8760, Hysorb® M7055N, Hysorb® B7015, Hysorb® M7015N, Hysorb® M7015 and Hysorb® 7400 are water-absorbent polymer particles from BASF SE, produced by a kneader polymerization process.

CE1 and CE2 correspond to water-absorbent polymer particles that are prepared in accordance to Example 7 and Example 26 of WO 2012/045705 A1.

CE3 corresponds to water-absorbent polymer particles that are prepared in accordance to Example 25 of WO 2013/007819 A1.

Figure 16:
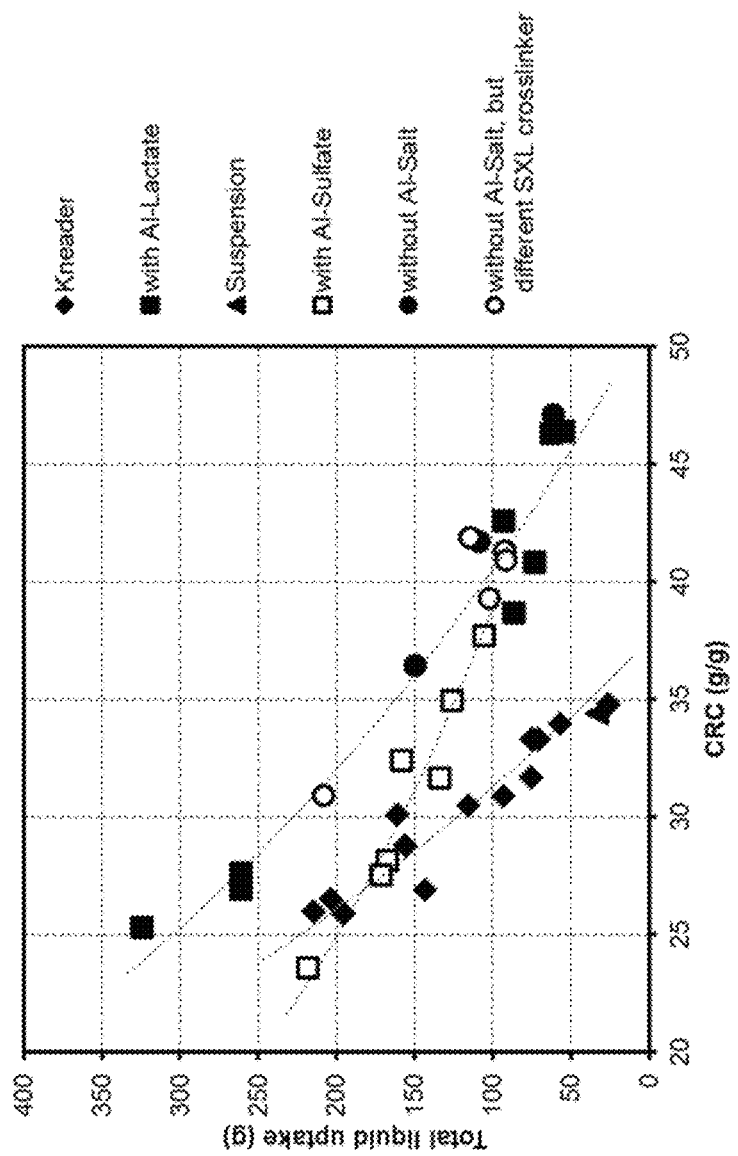
FIG. 16 is a graph of CRC (g/g) vs. Total liquid uptake (g) for water-absorbent polymer particles.

FIG. 16 is a diagram that shows that the water-absorbent polymer particles according to the present invention have an improved total quid uptake compared to conventional water-absorbent polymer particles having the same centrifuge retention capacity (CRC).

TABLE 11

Physical Properties of Comparison Example

| Comparison Example | CRC g/g | AUNL g/g | AUL g/g | AUHL g/g | SFC $10^{-7}$ cm$^3 \cdot$ s/g | GBP Da | Vortex s | Extractables % | FSR g/g · s | $\tau$ 0.03 psi s | $\tau$ 0.1 psi s | $\tau$ 0.3 psi s | $\tau$ 0.5 psi s | $\tau$ 0.7 psi s | Total liquid uptake g |
|---|---|---|---|---|---|---|---|---|---|---|---|---|---|---|---|
| Comparison Polymer Particles - Suspension Polymerization | | | | | | | | | | | | | | | |
| AQUA KEEP ® SA60SII | 34.4 | 56 | 27 | 14 | 0 | 2 | 38 | 3.1 | | 108 | 134 | 1033 | 1667 | 1534 | 32.9 |
| AQUA KEEP ® SA55XSII | 28.9 | | | 22 | 7 | 6 | 42 | 4.4 | 0.50 | 82 | 98 | 190 | 549 | 892 | |
| AQUA KEEP ® SA60SXII | 33.2 | | | 15 | 0 | 2 | 38 | 4.2 | 0.37 | 74 | 138 | 1215 | 2103 | 2154 | |
| Comparison Polymer Particles - Kneader Polymerization | | | | | | | | | | | | | | | |
| CE1 | 25.9 | 37.0 | 27.1 | 22.7 | 67 | 34 | 142 | 12.9 | 0.20 | | | | | | 195.1 |
| CE2 | 26.9 | 42.0 | 27.4 | 22.2 | 138 | 90 | 103 | 11.9 | 0.16 | 295 | 357 | 425 | 437 | | 143.0 |
| CE3 | 27.6 | 34.9 | 26.7 | 22.8 | 98 | 15 | 120 | 12.7 | 0.38 | 275 | 218 | 271 | 248 | | 214.2 |

TABLE 11-continued

| | | | | | | | | | | | | | | | |
|---|---|---|---|---|---|---|---|---|---|---|---|---|---|---|---|
| Hysorb ® B7075 | 28.8 | 40.9 | 29.4 | 24.3 | 45 | 7 | 92 | 8.2 | 0.25 | 319 | 389 | 467 | 442 | 372 | 155.6 |
| ASAP ® 535 | 30.1 | 45.6 | 29.7 | 23.5 | 50 | 18 | | 13.0 | 0.18 | 317 | 395 | 425 | 456 | 432 | 161.0 |
| Hysorb ® T9700 | 30.5 | 46.9 | 26.5 | 19.4 | 33 | 55 | | 11.5 | 0.26 | 376 | 406 | 400 | 374 | 372 | 115.1 |
| Hysorb ® B7055 | 29.4 | 43.3 | 29.8 | 22.3 | 9 | 4 | 93 | 10.0 | 0.19 | 291 | 363 | 353 | 462 | | 106.4 |
| Hysorb ® T8760 | 30.9 | 49.2 | 28.8 | 19.3 | 18 | 33 | 69 | 13.7 | 0.26 | 300 | 333 | 367 | 483 | 451 | 93.1 |
| Hysorb ® M7055N | 32.0 | 40.9 | 29.1 | 24.5 | 9 | 4 | 97 | 12.2 | 0.23 | 429 | 469 | 538 | 566 | 702 | 70.6 |
| Hysorb ® B7015 | 33.5 | 45.2 | 30.3 | 22.2 | 4 | 1 | 84 | 9.5 | 0.21 | 343 | 391 | 365 | 409 | 509 | 75.5 |
| Hysorb ® M7015N | 34.0 | 46.3 | 30.2 | 22.0 | 3 | 2 | 81 | 11.9 | 0.23 | 260 | 379 | 427 | 434 | 1184 | 57.0 |
| Hysorb ® M7015 | 34.0 | 47.2 | 29.5 | 21.7 | 2 | 7 | 59 | 12.5 | 0.29 | 227 | 229 | 356 | 500 | | 74.9 |
| Hysorb ® 7400 | 34.8 | 50.0 | 28.8 | 13.2 | 0 | 3 | 35 | 16.7 | 0.33 | 238 | 276 | 374 | 738 | 841 | 26.0 |

Example 33

A fluid-absorbent article—the baby diaper of size L—consisting 53% by weight of surface-postcrosslinked polymer of Example 12, was manufactured in a standard diaper production process:

The fluid-absorbent article comprises (A) an upper liquid-pervious layer comprising a spunbond nonwoven (three piece cover-stock) having a basis weight of 12 gsm (B) a lower liquid-impervious layer comprising a composite of breathable polyethylene film and spunbond nonwoven;

(C) an absorbent core between (A) and (B) comprising
  1) lower fluff layer of hydrophilic fibrous matrix of wood pulp fibers (cellulose fibers) acting as a dusting layer;
  2) a homogenous mixture of wood pulp fibers (cellulose fibers) and surface-postcrosslinked polymer. The fluid-absorbent core holds 53% by weight distributed surface-postcrosslinked polymer, the quantity of surface-postcrosslinked polymer within the fluid-absorbent core is 14.5 g. Dimensions of the fluid-absorbent core: length: 42 cm; front width: 12.8 cm; crotch width: 8.4 cm; rear width: 11.8 cm. The density of the fluid-absorbent core is for the font overall average 0.23 g/cm$^3$, for the insult zone 0.29 g/cm$^3$, for the back overall average 0.19 g/cm$^3$. The average thickness of fluid-absorbent core is 0.36 cm. The fluid-absorbent core is wrapped with a spunbond-meltblown-spunbond (SMS) nonwoven material having a basis weight of 10 gsm. The basis weight of fluid-absorbent core is for the font overall average 990 g/cm$^3$, for the insult zone 1130 g/cm$^3$, for the back overall average 585 g/cm$^3$.

(D) an air through bonded acquisition-distribution layer between (A) and (C) having a basis weight of 60 g/m$^2$; the acquisition-distribution layer is rectangular shaped and smaller than the fluid-absorbent core having a size of about 212 cm$^2$.

Dimension of the fluid-absorbent article: length: 51 cm; front width: 31.8 cm; crotch width: 22.4 cm; rear width: 31.8 cm. The fluid-absorbent article has average weight of 38.1 g.

The fluid-absorbent article further comprises:
  a. flat rubber elastics; elastics from spandex type fibers: 2 leg elastics and 1 cuff elastic
  b. leg cuffs from synthetic fibers, nonwoven material showing the layer combination SMS and having a basis weight of between 13 to 15 g/m$^2$ and a height of 3.0 cm
  c. mechanical closure system with landing zone of dimension 16.9 cm×3.4 cm and flexiband closure tapes of 3.1 cm×5.4 cm; attached to hook fastening tape of 1.9 cm×2.7 cm The rewet under load and rewet value of the fluid-absorbent article were determined. The results are summarized in Table 12 and 13.

Example 34

A fluid-absorbent article—the baby diaper of size L—consisting 49% by weight of surface-postcrosslinked polymer of Example 12 was manufactured in a standard diaper production process:

The fluid-absorbent article comprises the same components (A), (B) and (D) as in Example 33.

The absorbent core (C) between (A) and (B) comprises
  1) lower fluff layer of hydrophilic fibrous matrix of wood pulp fibers (cellulose fibers) acting as a dusting layer;
  2) a homogenous mixture of wood pulp fibers (cellulose fibers) and surface-postcrosslinked polymer. The fluid-absorbent core holds 49% by weight distributed surface-postcrosslinked polymer, the quantity of surface-postcrosslinked polymer within the fluid-absorbent core is 12.5 g. Dimensions of the fluid-absorbent core are the same as in Example 32. The density of the fluid-absorbent core is for the font overall average 0.26 g/cm$^3$, for the insult zone 0.27 g/cm$^3$, for the back overall average 0.19 g/cm$^3$. The average thickness of fluid-absorbent core is 0.31 cm. The fluid-absorbent core is wrapped with a spunbond—meltblown—spunbond (SMS) nonwoven material having a basis weight of 10 gsm. The basis weight of fluid-absorbent core is for the font overall average 971 g/cm$^3$, for the insult zone 979 g/cm$^3$, for the back overall average 515 g/cm$^3$.

Dimensions of the fluid-absorbent article are the same as in Example 33. The fluid-absorbent article has average weight of 35.7 g.

The fluid-absorbent article further comprises:
  a. flat rubber elastics as in Example 33
  b. leg cuffs, as in Example 33
  c. mechanical closure system, as in Example 33

The rewet under load and rewet value of the fluid-absorbent article were determined. The results are summarized in Table 12 and 13.

Example 35

A fluid-absorbent article—the baby diaper of size L—consisting 47.5% by weight of surface-postcrosslinked polymer of Example 12 was manufactured in a standard diaper production process:

The fluid-absorbent article comprises the same components (A), (B) and (D) as in Example 33.

The absorbent core (C) between (A) and (B) comprises
1) lower fluff layer of hydrophilic fibrous matrix of wood pulp fibers (cellulose fibers) acting as a dusting layer;
2) a homogenous mixture of wood pulp fibers (cellulose fibers) and surface-postcrosslinked base polymer. The fluid-absorbent core holds 47.7% by weight distributed surface-postcrosslinked polymer, the quantity of surface-postcrosslinked polymer within the fluid-absorbent core is 11.5 g. Dimensions of the fluid-absorbent core are the same as in Example 32. The density of the fluid-absorbent core is for the font overall average 0.24 g/cm$^3$, for the insult zone 0.26 g/cm$^3$, for the back overall average 0.18 g/cm$^3$. The average thickness of fluid-absorbent core is 0.32 cm. The fluid-absorbent core is wrapped with a spunbond—meltblown—spunbond (SMS) nonwoven material having a basis weight of 10 gsm. The basis weight of fluid-absorbent core is for the font overall average 928 g/cm$^3$, for the insult zone 967 g/cm$^3$, for the back overall average 495 g/cm$^3$.

Dimensions of the fluid-absorbent article are the same as in Example 33. The fluid-absorbent article has average weight of 34.8 g.

The fluid-absorbent article further comprises:
a. flat rubber elastics as in Example 33
b. leg cuffs, as in Example 33
c. mechanical closure system, as in Example 33

The rewet under load and rewet value of the fluid-absorbent article were determined. The results are summarized in Table 12 and 13.

Comparative Example

A fluid-absorbent article—the baby diaper of size L—consisting 52% by weight of surface-postcrosslinked polymer HySorb®B7075 (BASF SE, Ludwigshafen, Germany) was manufactured in a standard diaper production process:

The fluid-absorbent article comprises the same components (A), (B) and (D) as in Example 33.

The absorbent core (C) between (A) and (B) comprises
1) lower fluff layer of hydrophilic fibrous matrix of wood pulp fibers (cellulose fibers) acting as a dusting layer;
2) a homogenous mixture of wood pulp fibers (cellulose fibers) and surface-postcrosslinked base polymer (HySorb®B7075). The fluid-absorbent core holds 52% by weight distributed surface-postcrosslinked polymer, the quantity of surface-postcrosslinked polymer within the fluid-absorbent core is 14.5 g. Dimensions of the fluid-absorbent core are the same as in Example 32. The density of the fluid-absorbent core is for the font overall average 0.24 g/cm$^3$, for the insult zone 0.25 g/cm$^3$, for the back overall average 0.19 g/cm$^3$. The average thickness of fluid-absorbent core is 0.34 cm. The fluid-absorbent core is wrapped with a spunbond—meltblown—spunbond (SMS) nonwoven material having a basis weight of 10 gsm. The basis weight of fluid-absorbent core is for the font overall average 1013 g/cm$^3$, for the insult zone 971 g/cm$^3$, for the back overall average 548 g/cm$^3$.

Dimensions of the fluid-absorbent article are the same as in Example 33. The fluid-absorbent article has average weight of 38 g.

The fluid-absorbent article further comprises:
a. flat rubber elastics as in Example 33
b. leg cuffs, as in Example 33
c. mechanical closure system, as in Example 33

The rewet under load and rewet value of the fluid-absorbent article were determined. The results are summarized in Table 12 and 13.

TABLE 12

Rewet Under Load

| Example | Rewet Under Load | | | | |
|---|---|---|---|---|---|
| | 1st insult | 2nd insult | 3rd insult | 4th insult | 5th insult |
| 33 | 0.10 g | 0.12 g | 0.10 g | 0.09 g | 0.16 g |
| 34 | 0.10 g | 0.08 g | 0.07 g | 0.10 g | 0.27 g |
| 35 | 0.10 g | 0.06 g | 0.07 g | 0.14 g | 0.30 g |
| Comparative Example | 0.08 g | 0.08 g | 0.08 g | 0.29 g | 0.52 g |

TABLE 13

Rewet value

| Example | Rewet value | | | | |
|---|---|---|---|---|---|
| | 1st insult | 2nd insult | 3rd insult | 4th insult | 5th insult |
| 33 | 0.14 g | 0.10 g | 0.09 g | 0.10 g | 0.75 g |
| 34 | 0.15 g | 0.11 g | 0.11 g | 0.40 g | 1.61 g |
| 35 | 0.14 g | 0.10 g | 0.09 g | 0.87 g | 3.84 g |
| Comparative Example | 0.12 g | 0.22 g | 0.11 g | 0.82 g | 4.30 g |

The examples demonstrate that the fluid-absorbent article comprising spherical shaped surface-postcrosslinked polymer particles shows better rewet performance, even when the loading of spherical shaped surface-postcrosslinked polymer particles in the absorbent core is reduced up to 20%, in comparison to the fluid-absorbent article containing irregular shaped surface-postcrosslinked polymer particles.

The invention claimed is:

1. Surface-postcrosslinked water-absorbent polymer particles having a centrifuge retention capacity from 40 to 55 g/g, an absorption under high load from 25 to 35 g/g, a level of extractable constituents of less than 10% by weight, and a porosity from 20 to 40%.

2. Polymer particles according to claim 1, wherein polymer particles have a porosity from 25 to 30%.

3. Surface-postcrosslinked water-absorbent polymer particles having a total liquid uptake of $$Y > -485 \times \ln(X) + 1865$$

wherein Y (g) is the total liquid uptake and X (g/g) is the centrifuge retention capacity, wherein the centrifuge retention capacity is at least 25 g/g and the liquid uptake is at least 30 g.

4. Polymer particles according to claim 3, wherein the polymer particles have a centrifuge retention capacity of at least 40 g/g.

5. Polymer particles according to claim 3, wherein the polymer particles have a total liquid uptake of at least 45 g.

6. Surface-postcrosslinked water-absorbent polymer particles having a change of characteristic swelling time of less than 0.6 and a centrifuge retention capacity of at least 35 g/g, wherein the change of characteristic swelling time is $$Z=(\tau_{0.5}-\tau_{0.1})/\tau_{0.5}$$

wherein Z is the change of characteristic swelling time, $\tau_{0.1}$ is the characteristic swelling time under a pressure of 0.1 psi (6.9 g/cm$^2$) and $\tau_{0.5}$ is the characteristic swelling time under a pressure of 0.5 psi (35.0 g/cm$^2$).

7. Polymer particles according to claim 6, wherein the polymer particles have a change of characteristic swelling time of less than 0.4.

8. Polymer particles according to claim 6, wherein the polymer particles have a centrifuge retention capacity of at least 40 g/g.

9. Polymer particles according to claim 1, wherein the polymer particles have a mean sphericity from 0.80 to 0.95.

10. Polymer particles according to claim 1, wherein the polymer particles have a bulk density from 0.6 to 1 g/cm$^3$.

11. Polymer particles according to claim 1, wherein the polymer particles have an average particle diameter from 200 to 550 µm.

12. A fluid-absorbent article, comprising water-absorbent polymer particles according to claim 1 and less than 15% by weight fibrous material and/or adhesives in an absorbent core.

* * * * *